US007054758B2

(12) United States Patent
Gill-Garrison et al.

(10) Patent No.: US 7,054,758 B2
(45) Date of Patent: May 30, 2006

(54) COMPUTER-ASSISTED MEANS FOR ASSESSING LIFESTYLE RISK FACTORS

(75) Inventors: Rosalynn D. Gill-Garrison, Ryde (GB); Christopher J. Martin, Ryde (GB); Manuel V. Sanchez-Felix, Ryde (GB)

(73) Assignee: Sciona Limited, Ryde (GB)

( * ) Notice: Subject to any disclaimer, the term of this patent is extended or adjusted under 35 U.S.C. 154(b) by 687 days.

(21) Appl. No.: 09/771,933

(22) Filed: Jan. 30, 2001

(65) Prior Publication Data

US 2003/0023387 A1    Jan. 30, 2003

(51) Int. Cl.
G06F 19/00 (2006.01)
G06F 7/06 (2006.01)
G06N 3/12 (2006.01)
(52) U.S. Cl. .............................. 702/20; 702/19; 705/2
(58) Field of Classification Search ................. 702/19, 702/20; 128/920, 923
See application file for complete search history.

(56) References Cited

U.S. PATENT DOCUMENTS

| | | | |
|---|---|---|---|
| 4,358,535 A | 11/1982 | Falkow et al. |
| 4,683,195 A | 7/1987 | Mullis et al. |
| 4,683,202 A | 7/1987 | Mullis et al. |
| 4,757,063 A | 7/1988 | Parnham |
| 5,307,263 A | 4/1994 | Brown |
| 5,310,653 A | 5/1994 | Hanausek-Walaszek |
| 5,376,526 A | 12/1994 | Brown |
| 5,508,199 A | 4/1996 | Gonzalez et al. |
| 5,545,527 A | 8/1996 | Stevens et al. |
| 5,550,021 A | 8/1996 | Blum et al. |
| 5,569,212 A | 10/1996 | Brown |
| 5,585,232 A | 12/1996 | Farr |
| 5,601,435 A | 2/1997 | Quy |
| 5,678,571 A | 10/1997 | Brown |
| 5,686,246 A | 11/1997 | Kornman et al. |
| 5,773,215 A | 6/1998 | Hanausek-Walaszek |
| 5,782,814 A | 7/1998 | Brown et al. |
| 5,794,219 A | 8/1998 | Brown |
| 5,828,943 A | 10/1998 | Brown |
| 5,832,448 A | 11/1998 | Brown |
| 5,834,044 A | 11/1998 | Schmitz et al. |
| 5,837,832 A | 11/1998 | Chee et al. |
| 5,844,108 A | 12/1998 | Meyer |
| 5,849,989 A | 12/1998 | Edlund |
| 5,858,659 A | 1/1999 | Sapolsky et al. |
| 5,879,163 A | 3/1999 | Brown et al. |
| 5,891,622 A | 4/1999 | Morrow et al. |
| 5,897,493 A | 4/1999 | Brown |
| 5,899,855 A | 5/1999 | Brown |
| 5,913,310 A | 6/1999 | Brown |
| 5,918,603 A | 7/1999 | Brown |
| 5,920,871 A | 7/1999 | Macri et al. |
| 5,933,136 A | 8/1999 | Brown |
| 5,935,810 A | 8/1999 | Friedman |
| 5,936,810 A | 8/1999 | Nakamoto et al. |
| 5,940,801 A | 8/1999 | Brown |
| 5,950,634 A | 9/1999 | Ochi et al. |
| 5,951,300 A | 9/1999 | Brown |
| 5,955,111 A | 9/1999 | Perdrizet et al. |
| 5,956,501 A | 9/1999 | Brown |
| 5,985,559 A | 11/1999 | Brown |
| 5,997,476 A | 12/1999 | Brown |
| 6,001,968 A | 12/1999 | Friedman |
| 6,004,744 A | 12/1999 | Goelet et al. |
| 6,013,431 A | 1/2000 | Soderlund et al. |
| 6,023,686 A | 2/2000 | Brown |
| 6,040,155 A | 3/2000 | Kay |
| 6,045,996 A | 4/2000 | Cronin et al. |
| 6,046,317 A | 4/2000 | Koulu et al. |
| 6,048,689 A | 4/2000 | Murphy et al. |
| 6,048,837 A | 4/2000 | Friedman |
| 6,068,615 A | 5/2000 | Brown et al. |
| 6,074,821 A | 6/2000 | Rozen et al. |
| 6,124,439 A | 9/2000 | Friedman |
| 6,124,448 A | 9/2000 | Friedman |
| 6,130,211 A | 10/2000 | Chasalow |
| 6,133,039 A | 10/2000 | Heinecke |
| 6,144,837 A | 11/2000 | Quy |
| 6,167,386 A | 12/2000 | Brown |
| 6,168,563 B1 | 1/2001 | Brown |
| 6,177,461 B1 | 1/2001 | Chasalow |
| 6,186,145 B1 | 2/2001 | Brown |

(Continued)

FOREIGN PATENT DOCUMENTS

EP    0 382 261    8/1990

(Continued)

OTHER PUBLICATIONS

Abravaya, K., Carrino, J. J., Muldoon, S., and Lee, H. H. 1995. Detection of point mutation with a modified ligase chain reaction (Gap-LCR). Nucleic Acids Research. 23:675-682.

Agarwal, K., Jones, D. E., Daly, A. K., James, O. F., Vaidya, B., Pearce, S. & Bassendine, M. F., 2000, CTLA-4 gene polymorphism confers susceptibility to primary biliary cirrhosis, J Hepatol, 32, 4, p. 538-541.

(Continued)

Primary Examiner—Marjorie A. Moran
Assistant Examiner—Lori A. Clow
(74) Attorney, Agent, or Firm—Nixon & Vanderhye P.C.

(57) ABSTRACT

The present invention relates to methods of assessing disease susceptibility associated with dietary and lifestyle risk factors. The invention provides for analysis of alleles at loci of genes associated with lifestyle risk factors, and the disease susceptibility profile of an individual is determined by reference to datasets which further match the risk factor with lifestyle recommendations in order to produce a personalized lifestyle advice plan.

26 Claims, 2 Drawing Sheets

U.S. PATENT DOCUMENTS

| | | |
|---|---|---|
| 6,197,945 B1 | 3/2001 | Edlund |
| 6,210,272 B1 | 4/2001 | Brown |
| 6,233,539 B1 | 5/2001 | Brown |
| 6,240,393 B1 | 5/2001 | Brown |
| 6,274,310 B1 | 8/2001 | Habener |
| 6,284,219 B1 | 9/2001 | Ajami |
| 6,309,853 B1 | 10/2001 | Friedman |
| 6,330,426 B1 | 12/2001 | Brown et al. |
| 6,334,778 B1 | 1/2002 | Brown |
| 6,350,730 B1 | 2/2002 | Friedman |
| 6,368,273 B1 | 4/2002 | Brown |
| 6,376,242 B1 | 4/2002 | Hanson |
| 6,410,508 B1 | 6/2002 | Isales |
| 6,429,290 B1 | 8/2002 | Friedman |
| 6,471,956 B1 | 10/2002 | Friedman |
| 6,475,736 B1 | 11/2002 | Stanton, Jr. |
| 6,524,814 B1 | 2/2003 | Kay |
| 6,537,759 B1 | 3/2003 | Stanton, Jr. |
| 6,646,013 B1 | 11/2003 | Barker |
| 6,664,062 B1 | 12/2003 | Stanton, Jr. |
| 6,703,493 B1 | 3/2004 | Friedman |
| 6,734,160 B1 | 5/2004 | Friedman |
| 2002/0039990 A1 | 4/2002 | Stanton |
| 2002/0048763 A1 | 4/2002 | Penn |
| 2002/0052761 A1 | 5/2002 | Fey |
| 2002/0082410 A1 | 6/2002 | Edlund |
| 2002/0102581 A1 | 8/2002 | Hageman |
| 2002/0107211 A1 | 8/2002 | Friedman |
| 2002/0116731 A1 | 8/2002 | Allen |
| 2002/0119144 A1 | 8/2002 | Hanson |
| 2002/0123061 A1 | 9/2002 | Cleveland |
| 2002/0129396 A1 | 9/2002 | Allen |
| 2002/0132255 A1 | 9/2002 | Salceda |
| 2002/0137203 A1 | 9/2002 | Wiles |
| 2002/0144300 A1 | 10/2002 | Allen |
| 2002/0146698 A1 | 10/2002 | DePhillipo et al. |
| 2002/0155464 A1 | 10/2002 | Salceda |
| 2002/0155467 A1 | 10/2002 | Escary |
| 2002/0160443 A1 | 10/2002 | Tsipouras |
| 2002/0164344 A1 | 11/2002 | Macina |
| 2002/0172948 A1 | 11/2002 | Perlin |
| 2002/0177583 A1 | 11/2002 | Kiss |
| 2002/0177696 A1 | 11/2002 | Sun |
| 2002/0192220 A1 | 12/2002 | Sun |
| 2002/0192310 A1 | 12/2002 | Bland |
| 2002/0192666 A1 | 12/2002 | Sun |
| 2003/0022188 A1 | 1/2003 | Macina |
| 2003/0023387 A1 | 1/2003 | Gill-Garrison |
| 2003/0027161 A1 | 2/2003 | Bejanin |
| 2003/0027248 A1 | 2/2003 | Bejanin |
| 2003/0036632 A1 | 2/2003 | Soreq |
| 2003/0040002 A1 | 2/2003 | Ledley |
| 2003/0040039 A1 | 2/2003 | Friedman |
| 2003/0044815 A1 | 3/2003 | Salceda |
| 2003/0046110 A1 | 3/2003 | Gogolak |
| 2003/0059436 A1 | 3/2003 | Chishti |
| 2003/0060487 A1 | 3/2003 | Bamdad |
| 2003/0064419 A1 | 4/2003 | Chandrasiri Herath |
| 2003/0068616 A1 | 4/2003 | Polansky |
| 2003/0069199 A1 | 4/2003 | Polansky |
| 2003/0073133 A1 | 4/2003 | Leyland-Jones |
| 2003/0073612 A1 | 4/2003 | DePhillipo et al. |
| 2003/0077222 A1 | 4/2003 | Leyland-Jones |
| 2003/0077604 A1 | 4/2003 | Sun |
| 2003/0087244 A1 | 5/2003 | McCarthy |
| 2003/0092013 A1 | 5/2003 | McCarthy |
| 2003/0092095 A1 | 5/2003 | Huang |
| 2003/0092620 A1 | 5/2003 | Lucas |
| 2003/0092898 A1 | 5/2003 | Salceda |
| 2003/0096247 A1 | 5/2003 | Bejanin |
| 2003/0096248 A1 | 5/2003 | McCarthy |
| 2003/0099662 A1 | 5/2003 | Boyd |
| 2003/0099957 A1 | 5/2003 | McCarthy |
| 2003/0099958 A1 | 5/2003 | McCarthy |
| 2003/0104358 A1 | 6/2003 | Polansky |
| 2003/0113727 A1 | 6/2003 | Girn |
| 2003/0115617 A1 | 6/2003 | Allen |
| 2003/0121067 A1 | 6/2003 | Brennan |
| 2003/0124533 A1 | 7/2003 | Ross |
| 2003/0124535 A1 | 7/2003 | McCarthy |
| 2003/0124536 A1 | 7/2003 | McCarthy |
| 2003/0131367 A1 | 7/2003 | Guenther |
| 2003/0131368 A1 | 7/2003 | Allen |
| 2003/0138925 A1 | 7/2003 | Keith |
| 2003/0143544 A1 | 7/2003 | McCarthy |
| 2003/0152935 A1 | 8/2003 | Chandrasiri Herath |
| 2003/0152947 A1 | 8/2003 | Crossman |
| 2003/0157485 A1 | 8/2003 | Bejanin |
| 2003/0157554 A1 | 8/2003 | Giot |
| 2003/0158083 A1 | 8/2003 | Peters |
| 2003/0162186 A1 | 8/2003 | Bejanin |
| 2003/0165928 A1 | 9/2003 | Uitterlinden |
| 2003/0170628 A1 | 9/2003 | Bejanin |
| 2003/0170630 A1 | 9/2003 | Alsobrook, II |
| 2003/0175715 A1 | 9/2003 | Sun |
| 2003/0175736 A1 | 9/2003 | Chinnaiyan |
| 2003/0176672 A1 | 9/2003 | Salceda |
| 2003/0186442 A1 | 10/2003 | Sandal |
| 2003/0186871 A1 | 10/2003 | Waters |
| 2003/0187335 A1 | 10/2003 | McCarthy |
| 2003/0190381 A1 | 10/2003 | Bland |
| 2003/0198954 A1 | 10/2003 | Bejanin |
| 2003/0202976 A1 | 10/2003 | Johnson |
| 2003/0204418 A1 | 10/2003 | Ledley |
| 2003/0215819 A1 | 11/2003 | Frudakis |
| 2003/0217037 A1 | 11/2003 | Bicker |
| 2003/0219769 A1 | 11/2003 | Olson |
| 2003/0219802 A1 | 11/2003 | Dhaini |
| 2003/0224385 A1 | 12/2003 | Pihan |
| 2003/0232975 A1 | 12/2003 | Rosen |
| 2004/0002114 A1 | 1/2004 | Gregoire |
| 2004/0014097 A1 | 1/2004 | McGlennen |
| 2004/0023225 A1 | 2/2004 | McCarthy |
| 2004/0043389 A1 | 3/2004 | McCarthy |
| 2004/0063120 A1 | 4/2004 | Beer |
| 2004/0072216 A1 | 4/2004 | Johnson |
| 2004/0082613 A1 | 4/2004 | Schneider |
| 2004/0087035 A1 | 5/2004 | Hanson |
| 2004/0093331 A1 | 5/2004 | Garner |
| 2004/0106647 A1 | 6/2004 | Schneider |
| 2004/0110241 A1 | 6/2004 | Segal |
| 2004/0115701 A1 | 6/2004 | Comings |
| 2004/0115708 A1 | 6/2004 | Ardies |
| 2004/0121344 A1 | 6/2004 | Takarada |

FOREIGN PATENT DOCUMENTS

| | | |
|---|---|---|
| WO | WO 95/11995 | 5/1995 |
| WO | WO 97/18009 | 5/1997 |
| WO | WO 99/44062 | 9/1999 |
| WO | WO 99/64626 | 12/1999 |

OTHER PUBLICATIONS

Alexandrie, A.-K., Warholm, M., Carstensen, U., Axmon, A., Hagmar, L., Levin, J.O., Ostman, C., and Rannug, A. CYP1A1 polymorphisms affect urinary 1-hydroyprene levels after PAH exposure. Carcinogenesis 21(4)669-676, 2000.

Ambrosone, C.B., Freudenheim, J.L., Thompson, P.A., Bowman, E., Vena, J.E., Marshall, J.R., Graham, S., Laughlin, R., Nemoto, T., and Shields P.G. Manganese Superoxide Dismutase (MnSOD) Genetic Polymorphisms, Dietary Antioxidants, and Risk of Breast Cancer. Cancer Research 59: 602-606, 1999.

Ames, B. N. Cancer prevention and diet: Help from single nucleotide polymorphisms. Proceedings of the National Academy of Science USA 96(22): 12216-12218, 1999.

Aron, Y., Swierczewski, E., Lockhart, A., 1994. A simple and rapid micromethod for genomic DNA extraction from jugal epithelial cells. Application to human lymphocyte antigen typing in one large family of atopic/asthmatic probands. Allergy 49 (9): 788-90.

Barany, F. 1991. Genetic disease detection and DNA amplification and DNA amplification using cloned thermostable ligase. Proceedings of the National Academy of Science. USA 88:189-193.

Bell, D.A, Stephens, E., Castranio, T., Umback, D.M., Watson, M., Deakin, M., Elder, J., Duncan, H., Hendrickse, C., Strange, R.C. Polyadenylation polymorphism in the N-acetyltransferase gene 1 (NAT1) increases risk of colorectal cancer. Cancer Research 55: 3537-3542, 1995.

Bosron, W.F. and Li, T.K. Genetic polymorphism of human liver alcohol and aldehyde dehydrogenases and their relationship to alcohol metabolism and alcoholism. Hepatology 6: 502-510, 1986.

Brand, E., Ringel, J. & Sharma, A. M., 2000, Role of the angiotensinogen gene for essential hypertension, Herz, 25, 1, p. 15-25. Original in German, abstract in English provided.

Breslauer, et al., "Predicting DNA duplex stability from base sequence", Proc. Nat'l Acad. Sci. USA, 83: 3746-3750 (1986).

Brockton, N., Little, J., Sharp, L, and Cotton, S.C. N-Acetyltransferase Polymorphisms and Colorectal Cancer: A HuGE Review. American Journal of Epidemiology 151(9): 846-861, 2000.

Bryant, M.S., Skipper, P.L., Tannenbaum, S.R., and Niure, M. Haemoglobin adducts of 4-aminobiphenyl in smokers and non-smokers. Cancer Research 47: 612-618, 1987.

Buervenich, S., Sydow, O., Carmine, A., Zhang, Z., Anvret, M. & Olson, L., 2000, Alcohol dehydrogenase alleles in Parkinson's disease, Mov Disord, 15, 5, p. 813-818.

Bullido, M. J. & Valdivieso, F., 2000, Apolipoprotein E gene promoter polymorphisms in Alzheimer's disease, Microsc Res Tech, 50, 4, p. 261-267.

Cheung, V. G., et. al., 1999, Nature, Genetics, vol. 21, 15-19.

Corbo, R. M. & Scacchi, R., 1999, Apolipoprotein E(APOE) allele distribution in the world. Is APOE*4 a 'thrifty' allele?, Ann Hum Genet, 63, PT4, p. 301-310.

Costa, L. G., 2000, The emerging field of ecogenetics, Neurotoxicology, 21, 1-2, p. 86-89.

Cotton, S.C., Sharp, L., Little, J., and Brockton, N. Glutathione S-Transferase Polymorphisms and Colorectal Cancer (A HuGE review). American Journal of Epidemiology 151(1)7-32, 2000.

Cramer, D. W., Greenberg, E. R., Titus-Ernstoff, L., Liberman, R. F., Welch, W. R., Li, E. & Ng, W. G., 2000, A case-control study of galactose consumption and metabolism in relation to ovarian cancer, Cancer Epidemiol Biomarkers Prev, 9, 1, p. 95-101.

De Padua Mansur, A.; Annicchino-Bizzacchi, J.; Favarato, D.; Avakian, S. D.; Machado Cesar, L. A.; Franchini Ramires, J. A., 2000. Angiotensin-converting enzyme and apolipoprotein B polymorphisms in coronary artery disease. Am J Cardiol 85 (9): 1089-93.

Di Castelnuovo, A., D'Orazio, A., Amore, C., Falanga, A., Donati, M. B. & Iacoviello, L., 2000, The decanucleotide insertion/deletion polymorphism in the promoter region of the coagulation factor VII gene and the risk of familial myocardial infarction, Thromb Res, 98, 1, p. 9-17.

Dickey, C., Snatella, R., Hattis, D., Tang, D., Hsu, Y., Cooper, T., Young, T. and Perera F., Variability in PAH-DNA adduct measurements in peripheral mononuclear cells: implications for quantitative cancer risk assessment. Risk Analysis 17: 649-655, 1997.

Dietz, A.C., Zheng, W., Leff, M.A., Gross, M., Xiao, G.-F., Doll, M.A., Wen, W.-Q., Folsom, A.R., Hein, D.W. N-acetyltransferase-2 (NAT2) acetylation polymorphism, well-done meat intake and breast cancer risk among postmenopausal women. Proceedings of the American Association for Cancer Research, 40: 148, 1999.

Doll, M.A., Jiang, W., Deitz, A.C., Rustan, T.D., and Hein, D.W. Identification of a novel allele at the human NAT1 acetyltransferase locus. Biochem. Bulophys. Res. Commun. 233: 584-591, 1997.

Donati, M. B., Zito, F., Castelnuovo, A. D. & Iacoviello, L., 2000, Genes, coagulation and cardiovascular risk, J Hum Hypertens, 14, 6, p. 369-372.

Donis-Keller H., Green P, Helms C., et. al. (1987), A genetic map of the human genome. Cell, 51, 319-337.

Eberhart, M.V., Lee, C.Y., Liu, R.H. Antioxidant activity of fresh apples. Nature 405: 903-904, 2000.

Fernandez-Real, J. M., Vendrell, J., Ricart, W., Broch, M., Gutierrez, C., Casamitjana, R., Oriola, J. & Richart, C., 2000, Polymorphism of the tumor necrosis factor-alpha receptor 2 gene is associated with obesity, leptin levels, and insulin resistance in young subjects and diet-treated type 2 diabetic patients, Diabetes Care, 23, 6, p. 831-837.

Garte, S. The role of ethnicity in cancer susceptibility gene polymorphisms: the example of CYP1A1. Carcinogenesis 19(8) 1329-1332, 1998.

Gelder, C. M., Hart, K. W., Williams, O. M., Lyons, E., Welsh, K. I., Campbell, I. A., Marshall, S. E., 2000, Vitamin D receptor gene polymorphisms and susceptibility to Mycobacterium malmoense pulmonary disease, J Infect Dis, 181, 6, p. 2099-2102.

Gibbs, R. A., Nguyen, P. N., and Caskey, C. T. 1989. Detection of single DNA base differences by competitive oligonucleotides priming. Nucleic Acids Research. 17:2437-2448.

Gil, J.P., Lechner, M.C. Increased frequency of wild type arylamine-N-actyltransferase allel NAT2*4 homozygotes in Portuguese patients with colorectal cancer. Carcinogenesis 19(1) 37-41, 1998.

Giovannucci, E. Nutritional factors in humas cancers. Advances in Experimental Medicine and Biology 472:29-42, 1999.

Grossman, P. D., Bloch, W., Brinson, E., Chang, C. C., Eggerding, F. A., Fung, S., Iovannisci, D. A., Woo, S., and Winn-Deen, E. S. 1994. High-density multiplex detection of nucleic acid sequences: oligonucleotides ligation assay and sequence-coded separation. Nucleic Acid Research. 22:4527-4534.

Harries, L.W., Stubbins, M.J., Forman, D., Howard, G.c.W, Wolf R. Identification of genetic polymorphisms at the glutathione S-transferase pi locus and association with susceptibility to bladder, testicular, and prostate cancer. Carcinogenesis 18:641-644, 1997.

Heilbronn, L. K., Noakes, M., Morris, A. M., Kind, K. L., Clifton, P. M., 2000, 360His polymorphism of the apolipoproteinA-IV gene and plasma lipid response to energy restricted diets in overweight subjects, Atherosclerosis, 150, 1, p. 187-192.

Hein, D., Doll, M.A., Fretland, A.J., Leff, M.A., Webb, S.J., Xiao, U.-S.D., Nangju, N., Feng, Y., Molecular Genetics and Epidemiology of the NAT1 and NAT2 Acetylation Polymorphisms. Cancer Epidemiology, Biomarkers & Prevention 9: 29-42, 2000 (a).

Hein, D., N-Acetyltransferase genetics and their role in predisposition to aromatic and heterocyclic amine-induced carcinogenesis. Toxicology Letters 112-113: 349-356, 2000 (b).

Hennig, B. J., Parkhill, J. M., Chapple, I. L., Heasman, P. A. & Taylor, J. J., 1999, Association of a vitamin D receptor gene polymorphism with localized early-onset periodontal diseases, J Periodontol, 70, 9, p. 1032-1038.

Hirvonen, A. Polymorphisms of Xeno-biotic-Metaboilzing Enzymes and Susceptibility to Cancer. Environ Health Perspect 107 Supplement 1: 37-47, 1999.

Ikuta, S., Takagi K., Wallace, R. B., and Itakura, K. 1987. Dissociation Kinetics of 19 base paired oligonucleotides-DNA Duplexes containing different single mismatched base pairs. Nucleic Acids Research. 15:797-811.

Ilett, K.F., David, B.M., Dethon, P., Castlden, W.M, and Kwa, R. Acetylation pehotype in colorectoal carcinoma. Cancer Research 47: 1466-1469, 1987.

International Agency for Research on Cancer (IARC). Alcohol Drinking. IARC monographs on the evaluation of the carcinogenic risks to humans, IARC, Lyon. 44: 153-246, 1998.

Kato, S., Bowman, E.D., Harrington, A.M., et al Human lung carcinogen DNA adduct levels mediated by genetic polymorphisms in vivo. Journal of the National Cancer Institute 87:902-907, 1995.

Kawajiri, K., Eguchi, H., Nakachi, K., Sekiya., T., Yamamoto, M. Association of CYP1A1 germ line polymorphisms with mutations of the p53 gene in lung cancer. Cancer Research 56:72-76, 1996.

Landegren, U., Kaiser, R., Sanders, J., and Hood, L, 1988. A ligand-mediated gene detection technique. Science. 241:1077-1080.

Laplaud, P. M., Dantoine, T. & Chapman, M. J., 1998, Paraoxonase as a risk marker for cardiovascular disease: facts and hypotheses, Clin Chem Lab Med, 36, 7, p. 431-441.

Layton, D.W., Bogen, K.T., Knize, M.G., Hatch, F.T., Johnson, V.M., and Felton, J.S. Cancer risk of heterocyclic amines in cooked foods: an analysis and implications for research. Carcinogenesis 16: 39-52, 1995.

Maciag, P. C., Schlecht, N. F., Souza, P. S., Franco, E. L., Villa, L. L. & Petzl-Erler, M. L., 2000, Major histocompatibility complex class II polymorphisms and risk of cervical cancer and human papillomavirus infection in Brazilian women, Cancer Epidemiol Biomarkers Prev, 9, 11, p. 1183-1191.

MacKness, B., Mackness, M. I., Durrington, P. N., Arrol, S., Evans, A. E., McMaster, D., Ferrieres, J., Ruidavets, J. B., Williams, N. R. & Howard, A. N., 2000, Paraoxonase activity in two healthy populations with differing rates of coronary heart disease, Eur J Clin Invest, 30, 1, p. 4-10.

MacLeod, S., Sinha, R., Kadlubar, F.F., Lang, N.P. Polymorphisms of CYP1A1 and GSTM1 influence the in vivo function of CYP1A2. Mutation Research 376(1-2): 135-142, 1997.

Marchand, L. L., Wilkinson, G. R. & Wilkens, L. R., 1999, Genetic and dietary predictors of CYP2E1 activity: a phenotyping study in Hawaii Japanese using chlorzoxazone, Cancer Epidemiol Biomarkers Prev, 8, 6, p. 495-500.

Matthias, C., Bockmuhl, U., Jahnke, V., Harries, L., Wolf, C.R., Jones, P.W., Alldersea, J. Worrall, S.F., Hand, P., Fryer, A.A. et al, The glutathione -S-transferase GSTP1 polymorphism: effects on susceptibility to oral/phryngeal and laryngeal carcinomas. Pharmacogenetics 8: 1-6, 1997.

Miki, M. & Satoh, K., 1999, Genetic risk factors for chronic obstructive pulmonary disease (COPD), Nippon Rinsho, 57, 9, p. 1954-1958. Original in Japanese, abstract in English provided.

Mooney, L.A., Perera, F.P. Application of molecular epidemiology to lung cancer chemoprevention. Journal of Cellular Biochemistry Supplement 25:63-8, 1996.

Mooney, L.A., Santella, R.M., Covey, L., Jeffrey, A.M., Bigbee, W., Randall, M.C., Cooper, T.B., Ottman, R., Tsai, W.-Y., Wazneh, L. et al. Decline in DNA damage and other biomarkers in peripheral blood following smoking cessation. Cancer Epidemiological Biomarkers Prevention 4: 627-634, 1995.

Newton, C. R., Graham, A., Heptinstall, L. E., Powell, S. J., Summers, C., Kalsheker, N., Smith, J. C., and Markham, A. F. 1989. Analysis of any point mutation in DNA. The amplification refractory mutation system (ARMS). Nucleic Acids Research. 17:2503-2516.

Nickerson, D. A., Kaiser, R., Lappin, S., Stewart, J., Hood, L., and Landegren, U. 1990. Automated DNA diagnostics using an ELISA-based oligonucleotides ligation assay. Proceedings of the National Academy of Science. USA 87:8923-8927.

Oliveira, J. R. & Zatz, M., 1999, The study of genetic polymorphisms related to serotonin in Alzheimer's disease: a new perspective in a heterogenic disorder, Braz J Med Biol Res, 32, 4, p. 463-467..

Ordovas, J. M., Cupples, L. A., Corella, D., Otvos, J. D., Osgood, D., Martinez, A., Lahoz, C., Coltell, O., Wilson, P. W., Schaefer, E. J., 2000, Association of cholesteryl ester transfer protein-TaqlB polymorphism with variations in lipoprotein subclasses and coronary heart disease risk: the Framingham study, Arterioscler Thromb Vasc Biol, 20, 5, p. 1323-1329.

Ota, N., Hunt, S. C., Nakajima, T., Suzuki, T., Hosoi, T., Orimo, H., Shirai, Y. & Emi, M., 1999, Linkage of interleukin 6 locus to human osteopenia by sibling pair analysis, Hum Genet, 105, 3, p. 253-257.

Perera, F. P. Molecular epidemiology and prevention of cancer. Environmental Health Perspectives 103 Suppl 8: 233-6, 1995.

Perera, F.P. Environment and cancer: Who are susceptible? Science 278: 1068-1073, 1997.

Perera, F.P. and Weinstein I.B. Molecular epidemiology: recent advances and future directions. Carcinogenesis 21 (3): 517-524, 2000.

Pfutzer, R. H., Barmada, M. M., Brunskill, A. P., Finch, R., Hart, P. S., Neoptolemos, J., Furey, W. F. & Whitcomb, D. C., 2000, SPINK1/PSTI polymorphisms act as disease modifiers in familial and idiopathic chronic pancreatitis, Gastroenterology, 119, 3, p. 615-623.

PicoGreen dsDNA Quantitation Reagent and Kit Instruction, (1996) Molecular Probew, Eugene, Or.

68. Pluth, J. M., Nelson, D. O., Ramsey, M. J. & Tucker, J. D., 2000, The relationship between genotype and chromosome aberration frequencies in a normal adult population, Pharmacogenetics, 10, 4, p. 311-319.

69. Potter, J. D. Colorectal cancer: Molecules and Populations. Journal of the National Cancer Institute 91(11): 916-932, 1999.

Raknes, G., Fernandes Filho, J. A., Pandey, J. P., Myhr, K. M., Ulvestad, E., Nyland, H., Vedeler, C. A., 2000, IgG allotypes and subclasses in Norwegian patients with multiple sclerosis, J Neurol Sci, 175, 2, p. 111-115.

Rojas, M., Cascorbi, I., Alexandrov, K., Kried, E., Auburtin, G., Mayer, L., Kopp-Schnieder, A., Roots, I., and Bartsch, H. Modulation of benzo[a]pyrene diolepoxide-DNA adduct levels in human white blood cells by CYP1A1 GSTM1 and GSTT1 polymorphism, Carcinogenesis 21(1): 35-41, 2000.

Rosa-Rosa, L. Zimmermann, N., Bernstein, J. A., Rothenberg, M. E. & Khurana Hershey, G. K., 1999, The R576 IL-4 receptor alpha allele correlates with asthma severity, J Allergy Clin Immunol, 104, 5, p. 1008-1014.

Ryberg, D., Skaug, V., Hewer, A., Phillips, D.H., Harries, L.W., Wolf, C.R., Ogreid, D., Ulvik, A., Vu, P. Haugen, A. Genotypes of glutathione transferase M1 and P1 and their significance for lung DNA adduct levels and cancer risk. Carcinogenesis 18:1285-1289, 1997.

Rychlik, W., "Selection of Primers for Polymerase Chain Reaction", Methods in Molecular Biology, vol. 15: PCR Protocols: Current Methods and Applications, pp. 31-40 (1993) Humana Press.

Saiki, R. K., Walsh, P. S., Levenson, C. H., and Erlich, H. A. 1989. Genetic analysis of amplified DNA with immobilized sequence-specific oligonucleotides probes. Proceedings of the National Academy of Science. USA 86:6230-6234.

Salas, J., Jansen, S., Lopez-Miranda, J., Ordovas, J. M., Castro, P., Marin, C., Ostos, M. A., Bravo, M. D., Jimenez-Pereperez, J., Blanco, A., Lopez-Segura, F., Perez-Jimenez, F., 1998, The Sstl polymorphism of the apolipoprotein C-III gene determines the insulin response to an oral-glucose-tolerance test after consumption of a diet rich in saturated fats, Am J Clin Nutr, 68, 2, p. 396-401.

Schabath, M. B., Spitz, M. R., Zhang, X., Delclos, G. L., & Wu, X., 2000, Genetic variants of myeloperoxidase and lung cancer risk, Carcinogenesis, 21, 6, p. 1163-1166.

Shields, P. G., Harris, C.C. Cancer Risk and low-Penetrance Susceptibility Genes in Gene-Environment Interactions. Journal of Clinical Oncology 18(11) 2309-2315, 2000.

Sinha, R. & Caporaso, N., 1997, Heterocyclic amines, cytochrome P4501A2, and N-acetyltransferase: Issues involved in incorporating putative genetic susceptibility markers into epidemiological studies, Ann Epidemiol, 7, 5, p. 350-356.

Sinha, R., Chow, W.H., Kulldorff, M., Denobile, J., Butler, J., Garcia-Closas, M., Weil, R., Hoover, R.N., and Rothman, N. Well-done, Grilled Red Meat Increases the Risk of Colorectal Adenomas. Cancer Research 59: 4320-4324, 1999.

Smith, G., Stanley, L.A., Sim, E., Strange, R., and Wolf, C.R. Metabolic Polymorphisms and Cancer Susceptibility. Cancer Surveys 25: 27-65, 1995.

Syvanen, A. C., Sayantile, A., and Lukka, M. 1993. Identification of individuals by analysis of biallelic DNA markers, Using PCR and solid-phase minisequencing. American Journal of Human Genetics. 52:46-59.

Taningher, M., Malacame, D., Izzotti, A., Ugolini, D. Parodi, S. Drug metabolism polymorphisms as modulators of cancer susceptibility. Mutation Research 436: 227-261, 1999.

Togo, A. V., Suspitsin, E. N., Grigoriev, M. Y., Ilyushik, E. S., Karpova, M. B., Hanson, K. P. & Imyanitov, E. N., 2000, L-myc polymorphism in cancer patients, healthy blood donors and elderly, tumor-free individuals in Russia, Int J Cancer, 85, 6, p. 747-750.

Tsai, M. Y., Welge, B. G., Hanson, N. Q., Bignell, M. K., Vessey, J., Schwichtenberg, K., Yang, F., Bullemer, F. E., Rasmussen, R. & Graham, K. J., 1999, Genetic causes of mild hyperhomocysteinemia in patients with premature occlusive coronary artery diseases, Atherosclerosis, 143, 1, p. 163-170.

Ulrich, C.M., Kampman, F., Bigler, J., Schwartz, S.M., Chen, C., Bostick, R., Fosdick, L., Bereford, S.A.A., Yasui, Y., and Potter, J.D. Colorectal adenomas and the C677T MTHFR polymorphism: evidence for gene-environment interaction? Cancer Epidemiological Biomarkers Prevention 8: 659-668, 1999.

Verlaan-de Vries, M., Bogaard, M. E., van den Elst, H., van Boom, J. H., van der Eb, A. J., and Bos, J. L. 1986. A dot-blot screening procedure for mutated ras oncogenes using synthetic oligodeoxynucleotides. Gene. 50:313-320.

Vicente, V., Gonzalez-Conejero, R., Rivera, J. & Corral, J., 1999, the prothrombin gene variant 20210A in venous and arterial thromboembolism, Haematologica, 84, 4, p. 356-362.

Vineis, P. Molecular Epidemiology: Low-dose Carcinogens and genetic susceptibility. International Journal of Cancer 71: 1-3, 1997.

Wallace, A. J., Humphries, S. E., Fisher, R. M., Mann, J. I., Chisholm, A., Sutherland, W. H., 2000, Genetic factors associated with response of LDL subfractions to change in the nature of dietary fat, Atherosclerosis, 149, 2, p. 387-394.

Wallace, R. B., Johnson, M. J., Hirose, T., Miyake, T., Kawashima, E. H. and Itakura, K., 1981. The use of synthetic oligonucleotides as hybridisation probes. II. Hybridization of oligonucleotides of mixed sequence to rabbit beta-globin DNA. Nucleic Acids Research. 9:879-894.

Warrington, J. A., Dee, S. and Trulson, M., 2000, Large-Scale Genomic Analysis Using Affymetrix GeneChip® Probe Arrays. Microarray Biochip Technology, edited by M. Schena.

Wilkinson, R. J., Llewelyn, M., Toosi, Z., Patel, P., Pasvol, G., Lalvani, A., Wright, D., Latif, M. & Davidson, R. N., 2000, Influence of vitamin D deficiency and vitamin D receptor polymorphisms on tuberculosis among Gujarati Asians in west London: a case-control study, Lancet, 355, 9204, p. 618-621.

World Cancer Research Fund (WCRF) Panel. (Potter, J.D. Chair) Diet, nutrition, and the prevention of cancer: a global perspective. Washington, D.C.: WCRF/American Institute of Cancer Research, 1997.

Wu, D. Y., and Wallace, R. B. 1989. The ligation amplification reaction (LAR)-amplification of specific DNA sequences using sequential rounds of template-dependent ligation. Genomics. 4:560-569.

Yamada, N., Yamaya, M., Okinaga, S., Nakayama, K., Sekizawa, K., Shibahara, S. & Sasaki, H., 2000, Microsatellite polymorphism in the heme oxygenase-1 gene promoter is associated with susceptibility to emphysema, Am J Hum Genet, 66, 1, p. 187-195.

Yershov, G., Barsky, V., et al., 1996, Proc. Natl. Acad. Sci. USA, Genetics, vol. 93, 4913-4918.

Yokota, M., Ichihara, S., Lin, T. L., Nakashima, N. & Yamada, Y., 2000, Association of a T29—>C polymorphism of the transforming growth factor- beta1 gene with genetic susceptibility to myocardial infarction in Japanese, Circulation, 101, 24, p. 2783-2787.

Yokoyama, A., Muramatsu, T., Ohmori, T., Yokoyama, T., Okuyama, K., Takahashi, H., Hasegawa, Y., Higuchi, S., Maruyama, K., Shirakura, K., Ishii, H. Alcohol-related cancers and aldehyde dehydrogenase-2 in Japanese alcoholics. Carcinogenesis 19(8)1383-1387, 1998.

Zhang, Y., Coyne, M. Y., Will, S. G., Levenson, C. H., and Kawasaki, E. S. 1991. Single-base mutational analysis of cancer and genetic disease using membrane bound modified oligonucleotides. Nucleic Acids Research. 19: 3929-3933.

Zheng, W., Deitz, A.C., Campbell, D.R., Wen, W-Q., Cerhan, J.R., Sellers, T.A., Folsom, A.R., and Hein, D.W. N-acetyltransferase I genetic polymorphism, cigarette smoking, well-done meat intake, and breast cancer risk. Cancer Epidemiological Biomarkers Prevention 8: 233-239, 1999.

Zychma, M. J., Gumprecht, J., Zukowska-Szczechowska, E. & Grzeszczak, W., 1999, Polymorphisms in the genes encoding for human kinin receptors and the risk of end-stage renal failure: results of transmission/disequillibrium test. The End-Stage Renal Disease Study Group, J Am Soc Nephrol, 10, 10, p. 2120-2124.

Ban, Y. & Taniyama, M., 2000, Vitamin D Receptor Gene Polymorphism Is Associated with Graves' Disease in the Japanese Population, J Clin Endocrinol Metab, 85, 12, p. 4639-4643.

Humphries, S. E., Henry, J. A. & Montgomery, H. E., 1999, Gene-environment interaction in the determination of levels of haemostatic variables involved in thrombosis and fibrinolysis, Blood Coagul Fibrinolysis, 10 Suppl 1, p. S17-S21.

Lee, E., Huang, Y., Zhao, B. et al Genetic polymorphism of conjugating enzymes and cancer risk: GSTM1, GSTT1, NAT1 and NAT2. Journal of the Toxicological Society 23: 140-142, 1998.

Nakajima, T. & Aoyama, T., 2000, Polymorphism of drug-metabolizing enzymes in relation to individual susceptibility to industrial chemicals, Ind Health, 38, 2, p. 143-152.

Poolsup, N., Li Wan Po, A. & Knight, T. L., 2000, Pharmacogenetics and psychopharmacotherapy, J Clin Pharm Ther, 25, 3, p. 197-220.

Heller et al, "Gene Chips and Microarrays: Applications in disease Profiles, Drug Target Discovery, Drug Action and Toxicity", DNA Microarrays A Practical Approach, Edited by M. Schena, pp. 187-203; The Practical Approach Series, Series Editor: B.D. Hames; Jun. 24, 1999.

Clarke et al, "DNA Array Technology in the Molecular Pharmacology of Colorectal Cancer", Proc. Am. Assoc. Cancer Res. Annual Mtg. No. 41 2000, p. 721.

Burczak et al, "Impact of Genomics on Diagnostic Medicine", Drug Development Res. vol. 41 1997, pp. 193-204.

XP-002249016; Signals Magazine; Patient, Diagnose Thyself; pp. 1-6; Jan. 2, 2001; retrieved from internet site "signalsmag.com" Jul. 24, 2003.

XP-002249015; Home Based DNA Test Kit Press Release 'Online! Mar. 24, 1999; pp. 1-2, retrieved Jul. 24, 2003 from web site "D-FWMall.com".

XP-002249014; HealthScreenAmerica.com Press Release 'Online! Dec. 22, 1999; retrieved Jul. 24, 2003 from internet site "HealthScreenAmerica.com" "Bricks and Mortar"; pp. 1-2.

Christensen, "Making sense of centenarians—genes and lifestyle help people live through a century," Science News, 159; 156-157 (2001).

Kimura et al., "Genetic Association of manganese superoxide dismutase with exudative age-related muscular degeneration," Am. J. Opthal., 130(6): 769-773 (2000).

Forsberg et al (Arch Biochem Biophys (2001) May 1:389(1); 84-93).

Wong, K., Business 2.0, Nov. 2003 "The Wise Man Knows His Genetic Destiny".

Chapman, J., Daily Mail, Sep. 14, 2002 "Black Box That Reads Genes Will Change the Face of Health Care".

D'Angelo, J., Fox News Channel, Jan. 3, 2003 "Diet by Design: Using DNA to Personalize Health".

Firn, D., FT.com (Financial Times), Feb. 23, 2004 "Eat Your Way to Good Health".

Grimaldi, K., et al., Integrative Medicine, Aug./Sep. 2003 (vol. 2 No. 4, 34-46).

Pugh, R., Manchester Evening News, Oct. 1, 2002 "Measure Medicine".

Deutsch, C., NYT, Jul. 13, 2003 "Scientific Solutions to Save Your Skin".

Pollack, A., NYT, Oct. 1, 2002 "New Era of Consumer Genetics Raises Hope and Concerns".

Stuttaford, T., Times Online, Feb. 3, 2003 "Patients have a right to know".

Shape Magazine, "The DNA Diet" Aug. 2003, p. 115.

Powell, J., Star Tribune, Jul. 2003 "Determining genetic makeup could drive new nutritional products".

Van, J., The San Diego Union-Tribune, "Genetic Makeup may work against healthy eating habits" Monday, Sep. 3, 2001.

Hutton, D., Red Magazine, Apr. 2003 "Still Want to Know Your Future?".

Grierson, B., NYT, May 4, 2003 "What Your Genes Want You to Eat".

Sydney Morning Herald, Mar. 6, 2002 "The gene genie".

Jackman, C., et al., The Daily Telegraph, Jun. 25, 2001 "DNA map and diet could halt cancer".

Glover, J., The News, Jul. 26, 2002 "Gene genies pioneer the secret to a healthier life".

The Portsmouth News, Jul. 4, 2001 DNA profiling wins Havant firm international admirers.

Baxter, S., et al, The Sunday Times, Oct. 13, 2002 "This man has seen his future by decoding his on DNA. Soon everyone will be doing it . . . ".

Petersen, A., Wall Street Journal, Jul. 2003, "Born to be a Couch Potato: It Could Be in Your Genes".

Cellf—The Science of You—sample personal report in bound and unbound forms (2004) Sciona Ltd.

Cellf—The Science of You—Personal Nutri-genetic analysis brochure (2004) Sciona Ltd.

Cellf—The Science of You—Instructions and Lifestyle Questionnaire (6 pages) (2004) Sciona Ltd.

Cellf Nutirtion Panel Technology White Paper, Version 1.24, Jan. 16, 2004, Sciona Ltd.

Hutton, D., Vogue (2004) pp. 150-152 "Future Perfect".

Chasalow, Fred I., Abstract of WO 9745126 Dec. 4, 1997.

Takarada, Yutaka WO 2001JP5792 Jul. 5, 2001 (Abstract).

Hanson, Stephen R U.S. Appl. No. 10/117,837, filed Apr. 8, 2002 (Abstract).

U.S. Appl. No. 09/666,224, filed Sep. 21, 2000.

Kay; John PCT WO 9808863 Mar. 5, 1998 (Abstract).

FIGURE 1

SEQUENCE LISTING

```
<160> NUMBER OF SEQ ID NOS: 205

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 1
atcggtgaga ccattgcccg ctggg                                          25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 2
cccagcgggc aatggtctca ccgat                                          25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3
atcggtgaga ccgttgcccg ctggg                                          25

<210> SEQ ID NO 4
```

```
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
cccagcgggc aacggtctca ccgat                                         25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
acctccacct cctgggctca cacga                                         25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6
tcgtgtgagc ccaggaggtg gaggt                                         25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7
acctccacct cccgggctca cacga                                         25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
tcgtgtgagc ccgggaggtg gaggt                                         25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
caggtgcctt gtgtcttccg tttga                                         25

<210> SEQ ID NO 10
<211> LENGTH: 25
```

```
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
tcaaacggaa gacacaaggc acctg                                       25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 11
caggtgcctt gtatcttccg tttga                                       25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12
tcaaacggaa gatacaaggc acctg                                       25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 13
cttccgtttg acggaagaga atgga                                       25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 14
tccattctct tccgtcaaac ggaag                                       25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 15
cttccgtttg acagaagaga atgga                                       25

<210> SEQ ID NO 16
<211> LENGTH: 25
<212> TYPE: DNA
```

```
<213> ORGANISM: Artificial Sequence
<220> FEATURE:
<223> OTHER INFORMATION: Description of Artificial Sequence:
      Oligonucleotide

<400> SEQUENCE: 16
tccattctct tctgtcaaac ggaag                                   25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 17
acagcaaata ccgaaaaatc tactc                                   25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 18
gagtagattt ttcggtattt gctgt                                   25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 19
acagcaaata ccaaaaaatc tactc                                   25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 20
gagtagattt tttcctattt gctgt                                   25

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 21
taataataat aataaatgtc tttta                                   25

<210> SEQ ID NO 22
<211> LENGTH: 25
<212> TYPE: DNA
<213> ORGANISM: Artificial Sequence
```

```
<220> FEATURE:
<223> OTHER INFORMATION: Description of Artificial Sequence:
      Oligonucleotide

<400> SEQUENCE: 22
taaaagacat ttattattat tatta                                         25

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 23
taataataat aataaatgta tttta                                         25

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 24
taaaatacat ttattattt aatta                                          25

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 25
taataataat aaaaaatgtc tttta                                         25

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 26
taaaagacat tttttatttt aatta                                         25

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 27
taaaatacat tttttatttt aatta                                         25

<210> SEQ ID NO 28
<211> LENGTH: 25
<212> TYPE: DNA
<213> ORGANISM: Artificial Sequence
<220> FEATURE:
```

<223> OTHER INFORMATION: Description of Artificial Sequence:
      Oligonucleotide

<400> SEQUENCE: 28
aataataaat gtcttttaaa gatgg                                              25

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 29
ccatctttaa aagacattta ttatt                                              25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 30
aataaaaaat gtcttttaaa gatgg                                              25

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 31
ccatctttaa aagacatttt ttatt                                              25

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 32
aataataaat gtattttaaa gatgg                                              25

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 33
ccatctttaa aatacattta ttatt                                              25

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence:

-continued

Oligonucleotide

<400> SEQUENCE: 34
aataaaaaat gtattttaaa gatgg 25

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 35
ccatctttaa aatacatttt ttatt 25

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 36
agggtatttt tacatccctc cagtt 25

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 37
aactggaggg atgtaaaaat accct 25

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 38
agggtatttt tatatccctc cagtt 25

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 39
aactggaggg atataaaaat accct 25

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 40
ggaatctggt acctggacca aatca                                          25

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 41
tgatttggtc caggtaccag attcc                                          25

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 42
ggaatctggt acttggacca aatca                                          25

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 43
tgatttggtc caagtaccag attcc                                          25

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 44
cgcttgaacc tcgaacaatt gaaga                                          25

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 45
tcttcaattg ttcgaggttc aagcg                                          25

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

```
<400> SEQUENCE: 46
cgcttgaacc tcaaacaatt gaaga                                    25

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 47
tcttcaattg tttgaggttc aagcg                                    25

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 48
aacctggtga tggatccctt actat                                    25

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 49
atagtaaggg atccatcacc aggtt                                    25

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 50
aacctggtga tgaatccctt actat                                    25

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 51
atagtaaggg attcatcacc aggtt                                    25

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 52
```
gctacattgc ccgcaagcac aacct						25

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 53
aggttgtgct tgcgggcaat gtagc						25

<210> SEQ ID NO 54
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 54
cgctgcaaat acatctccct catct						25

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 55
agatgaggga gatgtatttg cagcg						25

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 56
cgctgcaaat acgtctccct catct						25

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 57
agatgaggga gacgtatttg cagcg						25

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 58

```
tctggcagga ggcgggcaag gatga                                              25
```

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 59

```
tcatccttgc ccgcctcctg ccaga                                              25
```

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 60

```
tctggcagga ggtgggcaag gatga                                              25
```

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 61

```
tcatccttgc ccacctcctg ccaga                                              25
```

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 62

```
accataaagc agaagctgat gccct                                              25
```

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 63

```
agggcatcag cttctgcttt atggt                                              25
```

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 64

```
agctggctcc ggtttggggg tatct                                              25
```

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 65
agatacccca aaaccggagc cagct                                          25

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 66
agctggctcc ggctttgggg tatct                                          25

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 67
agatacccca aagccggagc cagct                                          25

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 68
ttacagccca gatagctctt cagcc                                          25

<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 69
ggctgaagag ctatctgggc tgtaa                                          25

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 70
ttacagccca gacagctctt cagcc                                          25

<210> SEQ ID NO 71
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 71
ggctgaagag ctgtctgggc tgtaa                                   25

<210> SEQ ID NO 72
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 72
tgtctgcggg agccgatttc atcat                                   25

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 73
atgatgaaat cggctcccgc agaca                                   25

<210> SEQ ID NO 74
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 74
tgtctgcggg agtcgatttc atcat                                   25

<210> SEQ ID NO 75
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 75
atgatgaaat cgactcccgc agaca                                   25

<210> SEQ ID NO 76
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 76
tgaccagtga agaaagtgtc tttga                                   25

```
<210> SEQ ID NO 77
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 77
tcaaagacac tttcttcact ggtca                                         25

<210> SEQ ID NO 78
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 78
tgaccagtga agcaagtgtc tttga                                         25

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 79
tcaaagacac ttgcttcact ggtca                                         25

<210> SEQ ID NO 80
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 80
caggcataca ctgaagtgaa aactg                                         25

<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 81
cagttttcac ttcagtgtat gcctg                                         25

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 82
caggcataca ctaaagtgaa aactg                                         25

<210> SEQ ID NO 83
```

```
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 83
cagttttcac tttagtgtat gcctg                                          25

<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 84
tgcatctctg ccttacagat catgt                                          25

<210> SEQ ID NO 85
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 85
agatgatctg taaggcagag atgca                                          25

<210> SEQ ID NO 86
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 86
gggtttggac gctcatacc                                                 19

<210> SEQ ID NO 87
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 87
aatgtactgt tcccttctga tttgg                                          25

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 88
tccgtttgac ggaagagaat                                                20

<210> SEQ ID NO 89
<211> LENGTH: 20
<212> TYPE: DNA
<213> ORGANISM: Artificial Sequence
<220> FEATURE:
```

<223> OTHER INFORMATION: Description of Artificial Sequence: Primer

<400> SEQUENCE: 89
gggtctgcaa ggaacaaaat                                              20

<210> SEQ ID NO 90
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 90
gaaacataac cacaaacc                                                18

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 91
caacaataaa ccaacattaa aagc                                         24

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 92
acttctgtac tgggctctga cc                                           22

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 93
gcatcgacaa tgtaattcct gc                                           22

<210> SEQ ID NO 94
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 94
aatacagcac tggcatgg                                                18

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 95
caaggaacaa aatgatgtgg                                              20

```
<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 96
gtgggcttca tcctcaccta                                           20

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 97
gggtgataca tacacaaggg ttt                                       23

<210> SEQ ID NO 98
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 98
cagcccacac attcttgg                                             18

<210> SEQ ID NO 99
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 99
aagcgggaga tgaagtcc                                             18

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 100
aggttacccc aaaggccacc                                           20

<210> SEQ ID NO 101
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 101
gcaagtgatg cccatgtcg                                            19

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Primer
```

```
<210> SEQ ID NO 102
```

```
<400> SEQUENCE: 102
tcttctacct gaagagcaag tcc                                              23

<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 103
caagtcactt tgtgaccatt cc                                               22

<210> SEQ ID NO 104
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 104
cctgaactgc cacttcagc                                                   19

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 105
ccaggaagag aaagacctcc                                                  20

<210> SEQ ID NO 106
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 106
cccattctgt gtttgggttt tt                                               22

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 107
agaggctgag gtgggagaat                                                  20

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 108
gaggtcattc tgaaggccaa gg                                               22

<210> SEQ ID NO 109
<211> LENGTH: 20
```

<212> TYPE: DNA
<213> ORGANISM: Artificial Sequence
<220> FEATURE:
<223> OTHER INFORMATION: Description of Artificial Sequence: Primer

<400> SEQUENCE: 109
tttgtggact gctgaggacg                                                    20

<210> SEQ ID NO 110
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 110
tcctcagatc attgctcc                                                      18

<210> SEQ ID NO 111
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 111
taacgcaact aagtcatagt cc                                                 22

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 112
ggctgtgctt tctcgtcttc                                                    20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 113
ggtgacgttc aggttgttca                                                    20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 114
acagtggttg aaaaagtagg                                                    20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 115
caaaatgtag ataagggtgc                                                  20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 116
ttggtggcta caagatgtcg                                                  20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 117
aggtcctgaa cttccagcag                                                  20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 118
gctctatggg aaggaccagc                                                  20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 119
aagccacctg agggtaagg                                                   20

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 120
cagcagggtc tcaaaagg                                                    18

<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 121
gatggacagg cagaatgg                                                    18

<210> SEQ ID NO 122
<211> LENGTH: 18
<212> TYPE: DNA
<213> ORGANISM: Artificial Sequence

```
<220> FEATURE:
<223> OTHER INFORMATION: Description of Artificial Sequence: Primer

<400> SEQUENCE: 122
catgggcaag cggaagtg                                                    18

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 123
caggatagcc aggaagagaa agac                                             24

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 124
agacagggtc cccaggtcat                                                  20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 125
cagaggctga ggtgggagaa                                                  20

<210> SEQ ID NO 126
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 126
ggagttaatt tctgggaagg atcag                                            25

<210> SEQ ID NO 127
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 127
tggtctagat accagaatcc attctctt                                         28

<210> SEQ ID NO 128
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 128
ggcagcctct ggagttaatt tct                                              23
```

<210> SEQ ID NO 129
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 129
ttcccttctg atttggtcta gatacc                                    26

<210> SEQ ID NO 130
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 130
gggaacagta cattccaaat gaaga                                     25

<210> SEQ ID NO 131
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 131
tgttcgaggc ttaagagtaa aggagt                                    26

<210> SEQ ID NO 132
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 132
aacaattgaa gattttgagt ctatgaatac a                              31

<210> SEQ ID NO 133
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 133
tctgcaagga acaaaatgat ttactagt                                  28

<210> SEQ ID NO 134
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 134
gaaacataac cacaaacctt ttcaaa                                    26

<210> SEQ ID NO 135
<211> LENGTH: 25
<212> TYPE: DNA
<213> ORGANISM: Artificial Sequence
<220> FEATURE:
<223> OTHER INFORMATION: Description of Artificial Sequence: Primer

```
<400> SEQUENCE: 135
aaatcaccaa tttccaagat aacca                                            25

<210> SEQ ID NO 136
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 136
aaacataacc acaaaccttt tcaaataat                                        29

<210> SEQ ID NO 137
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 137
aaatcaccaa tttccaagat aacca                                            25

<210> SEQ ID NO 138
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 138
aatcaacttc tgtactgggc tctga                                            25

<210> SEQ ID NO 139
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 139
ccatgccagt gctgtatttg tt                                               22

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 140
tgcattttct gcttgacaga aga                                              23

<210> SEQ ID NO 141
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 141
tttgtttgta atatactgct ctctcctgat                                       30

<210> SEQ ID NO 142
```

```
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 142
gccaaagaag aaacaccaaa aaat                                          24

<210> SEQ ID NO 143
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 143
aaatgatgtg gttataaatg aagatgttg                                     29

<210> SEQ ID NO 144
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 144
aagaggttga agaagtgctg aaaaatat                                      28

<210> SEQ ID NO 145
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 145
atacatacac aagggtttat tttgttcct                                     29

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 146
gttccagccc acacattctt g                                             21

<210> SEQ ID NO 147
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 147
cgggagatga agtccttcag att                                           23

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 148
```

```
cctggtggac atggtgaatg                                              20

<210> SEQ ID NO 149
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 149
gcagatgctc acatagttgg tgtag                                        25

<210> SEQ ID NO 150
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 150
gggatgagag taggatgata catggt                                       26

<210> SEQ ID NO 151
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 151
gggtctcaaa aggcttcagt tg                                           22

<210> SEQ ID NO 152
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 152
tcattctgaa ggccaaggac tt                                           22

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 153
cagggcatca gcttctgctt                                              20

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 154
ggctgtgctt tctcgtcttc a                                            21

<210> SEQ ID NO 155
<211> LENGTH: 19
<212> TYPE: DNA
```

```
<213> ORGANISM: Artificial Sequence
<220> FEATURE:
<223> OTHER INFORMATION: Description of Artificial Sequence: Primer

<400> SEQUENCE: 155
ttctgcctgg agcccagat                                                19

<210> SEQ ID NO 156
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 156
gtgttgcatt tacttcagga gatgtt                                        26

<210> SEQ ID NO 157
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 157
tccagaaaat gctatgattg atatgac                                       27

<210> SEQ ID NO 158
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 158
gacctgaagc acttgaagga gaa                                           23

<210> SEQ ID NO 159
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 159
tcaaagaaaa gctgcgtgat ga                                            22

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 160
aagagcaagt cccccaagga                                               20

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 161
ctttgtgacc attccggttt g                                             21
```

<210> SEQ ID NO 162
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 162 cccctttggtg gctacaagat gt					22

<210> SEQ ID NO 163
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 163
agaccctcaa gccccaaca					19

<210> SEQ ID NO 164
<211> LENGTH: 14
<212> TYPE: DNA
<213> ORGANISM: Artificial Sequence
<220> FEATURE:
<223> OTHER INFORMATION: Description of Artificial Sequence: Probe

<400> SEQUENCE: 164
cggtgagacc attg					14

<210> SEQ ID NO 165
<211> LENGTH: 14
<212> TYPE: DNA
<213> ORGANISM: Artificial Sequence
<220> FEATURE:
<223> OTHER INFORMATION: Description of Artificial Sequence: Probe

<400> SEQUENCE: 165
cggtgagacc gttg					14

<210> SEQ ID NO 166
<211> LENGTH: 14
<212> TYPE: DNA
<213> ORGANISM: Artificial Sequence
<220> FEATURE:
<223> OTHER INFORMATION: Description of Artificial Sequence: Probe

<400> SEQUENCE: 166
ctccacctcc tggg					14

<210> SEQ ID NO 167
<211> LENGTH: 14
<212> TYPE: DNA
<213> ORGANISM: Artificial Sequence
<220> FEATURE:
<223> OTHER INFORMATION: Description of Artificial Sequence: Probe

<400> SEQUENCE: 167
ctccacctcc cggg					14

<210> SEQ ID NO 168
<211> LENGTH: 13
<212> TYPE: DNA
<213> ORGANISM: Artificial Sequence
<220> FEATURE:

<223> OTHER INFORMATION: Description of Artificial Sequence: Probe

<400> SEQUENCE: 168
gccttgtgtc ttc 13

<210> SEQ ID NO 169
<211> LENGTH: 14
<212> TYPE: DNA
<213> ORGANISM: Artificial Sequence
<220> FEATURE:
<223> OTHER INFORMATION: Description of Artificial Sequence: Probe

<400> SEQUENCE: 169
tgccttgtat cttc 14

<210> SEQ ID NO 170
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 170
cgtttgacgg aagag 15

<210> SEQ ID NO 171
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 171
cgtttgacag aagag 15

<210> SEQ ID NO 172
<211> LENGTH: 14
<212> TYPE: DNA
<213> ORGANISM: Artificial Sequence
<220> FEATURE:
<223> OTHER INFORMATION: Description of Artificial Sequence: Probe

<400> SEQUENCE: 172
aataccgaaa aatc 14

<210> SEQ ID NO 173
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 173
caaataccaa aaaat 15

<210> SEQ ID NO 174
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 174
catctccatc atctg 15

<210> SEQ ID NO 175
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 175
acatctccag catct                                                    15

<210> SEQ ID NO 176
<211> LENGTH: 18
<212> TYPE: DNA
<213> ORGANISM: Artificial Sequence
<220> FEATURE:
<223> OTHER INFORMATION: Description of Artificial Sequence: Probe

<400> SEQUENCE: 176
gccatcttta aaagacat                                                 18

<210> SEQ ID NO 177
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 177
gccatcttta aaatacatt                                                19

<210> SEQ ID NO 178
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 178
agggtatttt tacatccct                                                19

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Probe

<400> SEQUENCE: 179
agggtatttt tatatccctc                                               20

<210> SEQ ID NO 180
<211> LENGTH: 17
<212> TYPE: DNA
<213> ORGANISM: Artificial Sequence
<220> FEATURE:
<223> OTHER INFORMATION: Description of Artificial Sequence: Probe

<400> SEQUENCE: 180
tctggtacct ggaccaa                                                  17

<210> SEQ ID NO 181
<211> LENGTH: 19
<212> TYPE: DNA
<213> ORGANISM: Artificial Sequence
<220> FEATURE:
<223> OTHER INFORMATION: Description of Artificial Sequence: Probe

```
<400> SEQUENCE: 181
aatctggtac ttggaccaa                                              19

<210> SEQ ID NO 182
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 182
tgaacctcga acaat                                                  15

<210> SEQ ID NO 183
<211> LENGTH: 17
<212> TYPE: DNA
<213> ORGANISM: Artificial Sequence
<220> FEATURE:
<223> OTHER INFORMATION: Description of Artificial Sequence: Probe

<400> SEQUENCE: 183
ttgaacctca aacaatt                                                17

<210> SEQ ID NO 184
<211> LENGTH: 14
<212> TYPE: DNA
<213> ORGANISM: Artificial Sequence
<220> FEATURE:
<223> OTHER INFORMATION: Description of Artificial Sequence: Probe

<400> SEQUENCE: 184
ctggtgatgg atcc                                                   14

<210> SEQ ID NO 185
<211> LENGTH: 14
<212> TYPE: DNA
<213> ORGANISM: Artificial Sequence
<220> FEATURE:
<223> OTHER INFORMATION: Description of Artificial Sequence: Probe

<400> SEQUENCE: 185
ctggtgatga atcc                                                   14

<210> SEQ ID NO 186
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 186
caagcagttg ggc                                                    13

<210> SEQ ID NO 187
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 187
caagcacttg ggc                                                    13

<210> SEQ ID NO 188
<211> LENGTH: 16
```

```
<212> TYPE: DNA
<213> ORGANISM: Artificial Sequence
<220> FEATURE:
<223> OTHER INFORMATION: Description of Artificial Sequence: Probe

<400> SEQUENCE: 188
gcaaatacat ctccct                                                      16

<210> SEQ ID NO 189
<211> LENGTH: 16
<212> TYPE: DNA
<213> ORGANISM: Artificial Sequence
<220> FEATURE:
<223> OTHER INFORMATION: Description of Artificial Sequence: Probe

<400> SEQUENCE: 189
gcaaatacgt ctccct                                                      16

<210> SEQ ID NO 190
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 190
ccttgcccgc ctc                                                         13

<210> SEQ ID NO 191
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 191
cttgcccacc tcc                                                         13

<210> SEQ ID NO 192
<211> LENGTH: 12
<212> TYPE: DNA
<213> ORGANISM: Artificial Sequence
<220> FEATURE:
<223> OTHER INFORMATION: Description of Artificial Sequence: Probe

<400> SEQUENCE: 192
cctgcagacc cc                                                          12

<210> SEQ ID NO 193
<211> LENGTH: 14
<212> TYPE: DNA
<213> ORGANISM: Artificial Sequence
<220> FEATURE:
<223> OTHER INFORMATION: Description of Artificial Sequence: Probe

<400> SEQUENCE: 193
accccaaaac cgga                                                        14

<210> SEQ ID NO 194
<211> LENGTH: 14
<212> TYPE: DNA
<213> ORGANISM: Artificial Sequence
<220> FEATURE:
<223> OTHER INFORMATION: Description of Artificial Sequence: Probe

<400> SEQUENCE: 194
```

```
accccaaagc cgga                                                    14
```

<210> SEQ ID NO 195
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 195

```
agcccagata gct                                                     13
```

<210> SEQ ID NO 196
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 196

```
agcccagaca gct                                                     13
```

<210> SEQ ID NO 197
<211> LENGTH: 14
<212> TYPE: DNA
<213> ORGANISM: Artificial Sequence
<220> FEATURE:
<223> OTHER INFORMATION: Description of Artificial Sequence: Probe

<400> SEQUENCE: 197

```
aaatcggctc ccgc                                                    14
```

<210> SEQ ID NO 198
<211> LENGTH: 17
<212> TYPE: DNA
<213> ORGANISM: Artificial Sequence
<220> FEATURE:
<223> OTHER INFORMATION: Description of Artificial Sequence: Probe

<400> SEQUENCE: 198

```
aaatcgactc ccgcaga                                                 17
```

<210> SEQ ID NO 199
<211> LENGTH: 16
<212> TYPE: DNA
<213> ORGANISM: Artificial Sequence
<220> FEATURE:
<223> OTHER INFORMATION: Description of Artificial Sequence: Probe

<400> SEQUENCE: 199

```
cagtgaagaa agtgtc                                                  16
```

<210> SEQ ID NO 200
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 200

```
agtgaagcaa gtgtc                                                   15
```

<210> SEQ ID NO 201
<211> LENGTH: 21
<212> TYPE: DNA
<213> ORGANISM: Artificial Sequence

```
-continued

<220> FEATURE:
<223> OTHER INFORMATION: Description of Artificial Sequence: Probe

<400> SEQUENCE: 201
tcacagtttt cacttcagtg t                                              21

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Probe

<400> SEQUENCE: 202
tcacagtttt cactttagtg t                                              21

<210> SEQ ID NO 203
<211> LENGTH: 23
<212> TYPE: DNA
<213> ORGANISM: Artificial Sequence
<220> FEATURE:
<223> OTHER INFORMATION: Description of Artificial Sequence: Probe

<400> SEQUENCE: 203
ccatctttaa aatacattta tta                                            23

<210> SEQ ID NO 204
<211> LENGTH: 22
<212> TYPE: DNA
<213> ORGANISM: Artificial Sequence
<220> FEATURE:
<223> OTHER INFORMATION: Description of Artificial Sequence: Probe

<400> SEQUENCE: 204
catctttaaa atacattttt ta                                             22

<210> SEQ ID NO 205
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 205
taataataat aaaaaatgta tttta                                          25
```

COMPUTER-ASSISTED MEANS FOR ASSESSING LIFESTYLE RISK FACTORS

FIELD OF THE INVENTION

The present invention relates to methods of assessing disease susceptibility. In particular, it relates to methods of assessing disease susceptibility associated with dietary and lifestyle risk factors.

BACKGROUND OF THE INVENTION

Cancer is a disease influenced primarily by external factors. Up to 80% of human cancers arise from exposure to environmental agents. The majority of cancer is believed to be preventable because exposure to these external factors should be manageable (Giovannucci, 1999; Perera, 2000).

Human tumours result from a series of mutational events, leading to the loss of the regulatory mechanisms that govern normal cell behaviour and ultimately resulting in the formation of a tumour with full metastatic (or invasive) potential (Smith, 1995). All higher organisms have developed a complex variety of mechanisms to protect themselves from environmental insult, for example from ingested plant toxins. One of the most important protection measures involves the metabolism of toxins (or xenobiotics) leading to detoxification and ultimately excretion of the toxin (Smith, 1995). Unfortunately, the metabolic pathways do not always lead to detoxification of the toxin. Indeed many chemical carcinogens are activated by these same metabolic pathways to react with cellular macromolecules.

Improvements in genetic analysis and the availability of human genetic sequence information arising from the Human Genome Project has added another facet to the analysis of cancer susceptibility, that of inter-individual variation at the genome level. Molecular epidemiology has already begun to clarify some of the gene-environment interactions that may lead to disease. The ultimate goal of molecular epidemiology is to develop risk assessment models for individuals, and already the field has provided insight into inter-individual variation in human cancer risk (Shields, 2000). Molecular epidemiology focuses on three major determinants of human cancer risk: inherited host susceptibility factors, molecular dosimetry of carcinogen exposure, and biomarkers of early effects of carcinogenic exposure. The variability in metabolic activity, detoxification and DNA repair of the US population could be as high as 85–500-fold with correspondingly high variability in cancer risk (Hattis, 1986). Considering the latency of cancer, the importance of correlating individual risk with biomarkers at an early stage becomes apparent. These biomarkers can help to identify populations or individuals at risk of cancer resulting from specific environment-gene interactions.

Defining the factors that contribute to inter-individual variations in cancer susceptibility has been a major focus of research for many years. Given the suggested role of environmental factors in carcinogenesis, some of the candidate genes are those that encode the xenobiotic-metabolising enzymes that activate or inactivate carcinogens. Variable levels of expression of these enzymes could result in increased or decreased carcinogen activation. Other genetic factors that could contribute to cancer susceptibility include genes involved in DNA repair, proto-oncogenes, tumour suppressor genes, cell-cycle genes, as well as genes involved in aspects of nutrition, hormonal status, and immunological responses. Emerging data from the Human Genome Project has led to studies that show combinations of metabolic polymorphisms are increasingly being linked to a greater risk of cancer (Perera, 1997). Studies which have measured the formation of DNA adducts as a marker of enzyme activity have found that the levels of DNA damage or protein adducts vary considerably between persons with apparently similar exposure (Bryant, 1987; Perera, 1992; Mooney, 1995). The observed variability reflects a combination of true biologic factors, unaccounted for by differences in exposure or laboratory variation (Dickey, 1997). In fact, lower exposures to carcinogens can result in proportionately higher adduct levels because of a person's genetic predisposition for increased carcinogen metabolic activation (Kato, 1995; Vineis, 1997).

The existence of multiple alleles at loci that encode xenobiotic-metabolising enzymes can result in differential susceptibilities of individuals to the carcinogenic effects of various chemicals. Metabolism in humans occurs in two distinct phases: Phase I Metabolism involves the addition of an oxygen atom or a nitrogen atom to lipophilic (fat soluble) compounds such as steroids, fatty acids, xenobiotics (from external sources like diet, smoke, etc.) so that they can be conjugated to glutathione or N-acetylated by the Phase II enzymes (thus made water-soluble) and excreted from the body. There are superfamilies of xenobiotic-metabolising enzymes: cytochrome P450's (Phase I), GSTs (Phase II) and NATs (Phase I and II) which are thought to have evolved as an adaptive response to environmental insult. Alterations in the activity of these enzymes are predicted to result in an altered susceptibility to cancer (Hirvonen, 1999).

Enzymatic activation of xenobiotics is not, however, the only route to cancer development. Epidemiological studies suggest that nutritional factors may also play a causative role in more than 30% of human cancers. However, defining the precise roles of specific dietary factors in the development of cancer is difficult due to the multitude of variables involved (Perera, 2000). Specific dietary factors are not easily measured as a single quantifiable variable, such as number of cigarettes smoked per day. Further complications arise due to differences in methodology, control populations, types of carcinogens, and amounts of exposure to carcinogens.

Priorities for studies relating to the interrelationship of dietary factors and cancer susceptibility include identification of genetic factors that contribute to individual cancer risk, identification of cancer-preventative chemicals in fruits and vegetables, better understanding of carcinogenic role of polycyclic aromatic hydrocarbons and heterocyclic amines generated by cooking meats at high temperature, and better understanding of the role of increased caloric intake with increased cancer risk (Perera, 2000).

Increased consumption of vegetables and fruits is correlated with a decreased risk of cancer, and studies of this aspect of nutritional effects on cancer has led to the identification of other enzymes and micronutrients involved in the maintenance of a normal cellular phenotype (Giovannuci, 1999).

One quarter of the US population with low intake of fruits and vegetables has roughly twice the cancer rate for most types of cancer (lung, larynx, oral cavity, oesophagus, stomach, colon and rectum, bladder, pancreas, cervix, and ovary) when compared with the quarter with the highest intake (Ames, 1999). Fruit and vegetables are high in folate and antioxidants. Low intake can lead to micronutrient deficiency, which has been shown to cause DNA damage in a way that mimics radiation damage by causing single and double-stranded breaks, oxidative lesions or both. The micronutrients correlated with DNA-damaging activity include folate (or folic acid), iron, zinc, and vitamins B12, B6, C and E (Ames, 1999).

Of the cancers that are correlated with nutritional effects, colon cancer (colorectal neoplasia) has among the strongest links to diet. In the US, colon cancer is the fourth most common incident cancer and second most common cause of cancer death in the US, with 130,000 new cases and 55,000 deaths per year (Potter, 1999). According to the WHO, colorectal cancers are the second most common cause of cancer death in Britain (WHO, 1997). Worldwide colon cancer represents 8.5% of new cancer cases reported, with the highest rates seen in the developed world and the lowest rates in India. Colon cancer occurs with approximately equal frequency in men and women, and the occurrence appears to be highly sensitive to changes in the environment. Immigrant populations assume the incidence rates of the host country very rapidly, often within the generation of the initial immigrant (Potter, 1999).

Risk factors for colon cancer include a positive family history, meat consumption, smoking and alcohol consumption (Giovannuci, 1999). There is an inverse relationship, i.e. lower risk, associated with consumption of vegetables, high folate intakes, use of non-steroidal anti-inflammatory drugs, hormone replacement therapy and physical activity. Meat and tobacco smoke are sources of carcinogens, while vegetables are a source of folate, antioxidants, and have Phase II (detoxifying) enzyme-inducing ability (Taningher, 1999).

Diets rich in raw vegetables, green vegetables, and cruciferous vegetables have a decreased risk of colon cancer. Diets high in fibre, from vegetables and cereals, have been associated with a greater than two-fold decrease in risk of colorectal adenomas in men. The data on fruit in the diet is not as consistent to date (WCRF, 1997), but a recent report (Eberhart, 2000) measured potent anti-oxidant activity of phytochemicals in apple skins with the ability to inhibit growth of tumour cell lines in vitro, so it is possible that more clearly defined links will emerge in the future. Lower risk of colon cancer is associated with high folate intakes, but actual consumption of vegetables, rather than specific micronutrient preparations or vitamin supplements, has the most consistent low risk (Potter, 1999).

Other cancers that have been correlated with nutrition include prostate and breast. These malignancies are largely influenced by a combination of factors related to diet and nutrition. Prostate cancer is associated with high consumption of milk, dairy products and meats. These products decrease levels of 1,25(OH)2 vitamin D, which is a cell differentiator. Low levels of 1,25(OH)2 vitamin D may enhance prostate carcinogenesis by preventing cells from undergoing terminal differentiation and continuing to proliferate (Giovannucci, 1999). Breast, colon, and prostate cancers are relatively rare in less economically developed countries, where malignancies of the upper gastrointestinal tract are quite common. The cancers of the upper gastrointestinal tract have been related to various food practices or preservation methods other than refrigeration. For example, cancer of the mouth and pharynx is the sixth most common cancer world-wide and has been linked to alcohol consumption, tobacco, salt-preserved meat and fish, smoked foods and charcoal-grilled meat, as well as ingestion of beverages drunk very hot. Thus, diet can be a direct supply of genotoxic compounds or may cause chronic irritation or inflammation (Giovannucci, 1999).

In recent years, many genes involved in the processes described above and other areas of metabolism have been found to exist in allelic form. Therefore, certain populations, subpopulations, races etc have greater or lesser susceptibility to particular diseases linked with variation in alleles of some genes. For many decades, health advice, for example relating to diet, exercise, smoking, sunbathing has been issued by Governments, charities and health advisory bodies, such advice has been directed only at the population as a whole, or, at best, to groups such as the elderly, children and pregnant women. Such advice can therefore only be very general and cannot, by its very nature, take account of the particular genotype of an individual. Moreover, in recent years, there has been much media publicity of research findings on links between particular foods, drugs etc and medical conditions, often causing health scares. As the factors that contribute to disease susceptibility, for example cancer, or cardiovascular disease susceptibility vary between populations and between individuals of populations, it is often impossible for an individual to derive useful advice appropriate to his or her particular circumstances from such reports.

SUMMARY OF THE INVENTION

In order to enable individuals to protect and manage their own health, there is a need for individuals to have personally-tailored information about risk factors which may be important to that individual's well-being and personally-tailored advice on reducing the risk of disease.

Accordingly, the invention provides a computer assisted method of providing a personalized lifestyle advice plan for a human subject comprising:

(i) providing a first dataset on a data processing means, said first dataset comprising information correlating the presence of individual alleles at genetic loci with a lifestyle risk factor, wherein at least one allele of each genetic locus is known to be associated with increased or decreased disease susceptibility;

(ii) providing a second dataset on a data processing means, said second dataset comprising information matching each said risk factor with at least one lifestyle recommendation;

(iii) inputting a third dataset identifying alleles at one or more of the genetic loci of said first dataset of said human subject;

(iv) determining the risk factors associated with said alleles of said human subject using said first dataset;

(v) determining at least one appropriate lifestyle recommendation based on each identified risk factor from step (iv) using said second dataset; and (vi) generating a personalized lifestyle advice plan based on said lifestyle recommendations.

By lifestyle risk factors, it is meant risk factors associated with dietary factors, exposure to environmental factors, such as smoking, environmental chemicals or sunlight. Similarly lifestyle recommendations should be interpreted as relating to recommendations relating to dietary factors and exposure to environmental factors, such as smoking, environmental chemicals or sunlight. Disease susceptibility should be interpreted to include susceptibility to conditions such as allergies.

Thus, the method allows individualised advice to be generated based on the unique genetic profile of an individual and the susceptibility to disease associated with the profile. By individually assessing the genetic make-up of the client, specific risk factors can be identified and dietary and other health advice tailored to the individual's needs. In a preferred embodiment, the lifestyle advice will include recommended minimum or maximum amounts of food-types. (Note that an amount may be 0).

Information concerning the sex and health of the individual and/or of the individual's family may also provide indications that a particular polymorphism or group of polymorphisms associated with a particular condition should be investigated. Such information may therefore be used in selection of polymorphisms to be screened for in the method of the invention.

Such factors may also be used in the determination of appropriate lifestyle recommendations in step (v) of the method. For example, recommendations relating to reducing susceptibility to prostate cancer would not be given to women and recommendations relating to susceptibility to ovarian cancer would not be given to men. Other factors, such as information regarding the age, alcohol consumption, and existing diet of the client may be incorporated into the determination of appropriate lifestyle recommendations in step (v).

The report comprising the personalised dietary advice may be delivered to the client by any suitable means, for example by letter, facsimile or electronic means, such as e-mail. Alternatively, the report may be posted on a secure Web-page of the service provider with access limited to the client by the use of a unique identifier notified to the client either by conventional or electronic mail. The report can therefore comprise one or more hyperlinks to other documents of the report provider's Web-site or to other Web-sites giving relevant information on the particular polymorphisms identified, disease prevention and/or dietary advice.

As such sites would be able to be updated and new hyperlinks added to the report after the report is initially delivered to the client, the information and advice would be able to be updated at any time, thereby allowing the client to access up-to-date yet personalised health and dietary advice over a prolonged period, without the need for requesting another report.

Preferably, the method will involve assessing a variety of loci in order to give a broad view of susceptibility and possible means of minimising disease risk. Although individual polymorphisms may be considered biomarkers for individual cancer risk, the different biomarkers, when considered together, may also reveal a significant cancer risk. For example, the correlation between CYP1A1 activity and cancer susceptibility varies, dependent on the presence of specific types of CYP1A1 polymorphism as well as the presence of GSTM1 polymorphisms. An individual with an extremely active CYP1A1 gene, leading to high Phase I P450 activity in combination with a null GSTM1 genotype that lacks the detoxifying Phase II activities has a very high risk of developing cancer (Taningher, 1999).

The presence of a particular polymorphism may be indicative of increased susceptibilty to one disease while being indicative of decreased susceptibility to another disease. For example, one allele of the gene encoding epoxide hydrolase, which catalyses the conversion of toxic PAH metabolites formed by CYP1A1 and CYP1A2 into less toxic and more water-soluble trans-dihydrodiols, has recently been found to be associated with increased risk of aflatoxin-induced liver cancer, but also with decreased risk of ovarian cancer (Pluth, 200; Taningher, 1999).

Therefore, it will be important to assess the risk factors associated with other polymorphisms to give meaningful advice on maintaining optimal health.

Preferred genes for which polymorphisms are identified include genes that encode Phase I metabolism enzymes responsible for detoxification of xenobiotics, genes that encode Phase II metabolism enzymes responsible for further detoxification and excretion of xenobiotics, genes that encode enzymes that combat oxidative stress, genes associated with micronutrient deficiency (for example, deficiency of folate, B12 or B6), genes that encode enzymes responsible for metabolism of alcohol, genes that encode enzymes involved in lipid and/or cholesterol metabolism, genes that encode enzymes involved in clotting, genes that encode trypsin inhibitors, genes that encode enzymes related to susceptibility to metal toxicity, genes which encode proteins required for normal cellular metabolism and growth and genes which encoded HLA Class 2 molecules.

The method of the invention may include the step of determining the presence of individual alleles at one or more genetic loci of the DNA in a DNA sample of the subject, and constructing the dataset used in step (iii) using results of that determination.

Techniques for determining the presence or absence of individual alleles are known to the skilled person. They may include techniques such as hybridization with allele-specific oligonucleotides (ASO) (Wallace, 1981; Ikuta, 1987; Nickerson, 1990, Varlaan-de Vries, 1986, Saiki, 1989 and Zhang, 1991) allele specific PCR (Newton 1989, Gibbs, 1989), solid-phase minisequencing (Syvanen, 1993), oligonucleotide ligation assay (OLA) (Wu, 1989, Barany, 1991; Abravaya, 1995), 5' fluorogenic nuclease assay (Holland, 1991 & 1992, Lee, 1998) U.S. Pat. Nos. 4,683,202, 4,683,195, 5,723,591 and 5,801,155, or Restriction fragment length polymorphism (RFLP) (Donis-Keller, 1987).

In a preferred embodiment, the genetic loci are assessed via a specialised type of PCR used to detect polymorphisms, commonly referred to as the Taqman® assay, in which hybridisation of a probe comprising a fluorescent reporter molecule, a fluorescent quencher molecule and a minor groove binding chemical to a region of interest is detected by removal of quenching of the fluorescent molecule and detection of resultant fluorescence. Details are given below.

In another embodiment, the genetic loci are assessed via hybridisation with allele-specific oligonucleotides, the allele specific oligonucleotides being preferably arranged as an array of oligonucleotide spots stably associated with the surface of a solid support.

The arrays suitable for use in the method of the invention form a further aspect of the present invention.

In order to assay the sample for the alleles to be identified the fragments of DNA comprising the gene(s) of interest may be amplified to produce a sufficient amount of material to be tested.

The present inventors have designed a number of specific primer sets for amplification of gene regions of interest. Such primers may be used in pairs to isolate a particular region of interest in isolation. Therefore in a further aspect of the invention, there is provided a primer having a sequence selected from SEQ ID NO: 86–99, 104–163. In another aspect, there is provided a primer pair comprising primers having SEQ ID NO:n, where n is an even number from 86–98 or 104–162 in conjunction with a primer having SEQ ID NO: (n+1).

Preferably, however, the primer sets will be used together with other primer sets to provide multiplexed amplification of a number of regions to allow determination of a number of polymorphisms from the same sample. Therefore in a further aspect of the invention, there is provided a primer set comprising at least 5, more preferably 10, 15 primer pairs selected from SEQ ID NO: 86–121.

BRIEF DESCRIPTION OF THE DRAWINGS

FIG. 1 shows examples of databases 1 and 2 which may be used in an embodiment of the present invention.

DETAILED DESCRIPTION OF THE INVENTION

Selection of Genetic Polymorphisms for Datasets

Figure 2:
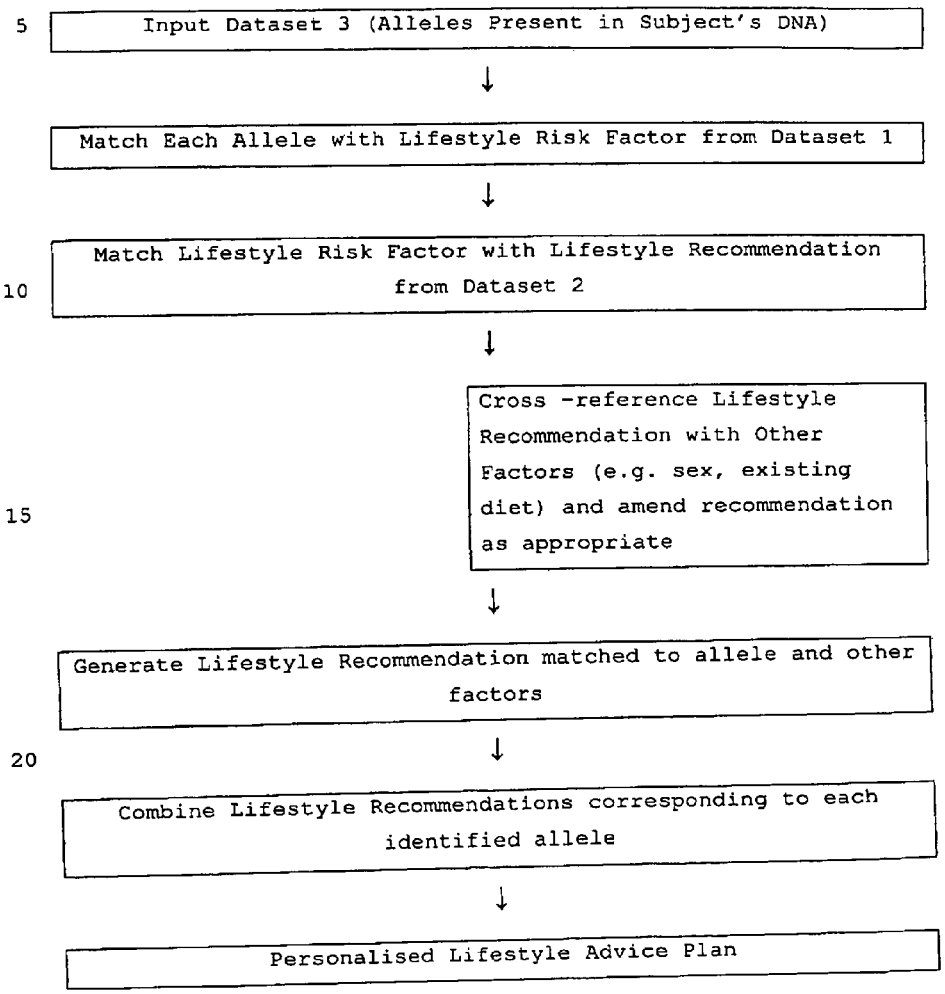
FIG. 2 is a flow chart illustrating an embodiment of the invention.

The correct selection of genetic polymorphisms is important to the provision of accurate and meaningful advice. Although not limited to such classes of polymorphisms, in a preferred embodiment of the present invention, markers for polymorphisms of one or more of the following classes of genes are used:

The first dataset of the method of the invention may comprise information relating to two or more alleles of one or more genetic loci of genes selected from the group comprising:

(a) genes that encode enzymes responsible for detoxification of xenobiotics in Phase I metabolism;
(b) genes that encode enzymes responsible for conjugation reactions in Phase II metabolism;
(c) genes that encode enzymes that help cells to combat oxidative stress;
(d) genes associated with micronutrient deficiency;
(e) genes that encode enzymes responsible for metabolism of alcohol.
(f) genes that encode enzymes involved in lipid and/or cholesterol metabolism;
(g) genes that encode enzymes involved in clotting;
(h) genes that encode trypsin inhibitors;
(i) genes that encode enzymes related to susceptibility to metal toxicity;
(j) genes which encode proteins required for normal cellular metabolism and growth;
(k) genes which encoded HLA Class 2 molecules.

The dataset will preferably comprise information relating to two or more alleles of at least two genetic loci of genes selected from the group comprising categories a–k as described above, for example, a+b, a+c, a+d, a+e, a+f, a+g, a+h, a+i, a+j, a+k, b+c, b+d, b+e etc., c+d, c+e etc, d+e, d+f etc, e+f, e+g etc, f+g, f+h etc., g+h, g+i, g+k, h+i, h+k. Where the dataset comprises information relating to two or more alleles of at least two genetic loci, it is preferred that at least one of the genetic loci is of category d, due to the central role of micronutrients in the maintenance of proper cellular growth and DNA repair, and due to the association of micronutrient metabolism or utilisation disorders with several different types of diseases (Ames 1999; Perera, 2000; Potter, 2000). More preferably, the dataset will preferably comprise information relating to two or more alleles of at least three genetic loci selected from the group comprising categories a–k as described above. Where the dataset comprises information relating to alleles of at least three genetic loci, it is preferred that at least two of the genetic loci are of categories d and e. Information relating to polymorphisms present in both of these categories is particularly useful due to the effects of alcohol consumption and metabolism on the efficiency of enzymes related to micronutrient metabolism and utilisation (Ulrich, 1999). In a further preferred embodiment, where the dataset comprises information relating to alleles of at least three genetic loci, it is preferred that at least two of the genetic loci are of categories a and b due to the close interaction of Phase I and Phase II enzymes in the metabolism of xenobiotics. Even more preferably, the dataset will comprise information relating to two or more alleles of at least four genetic loci of genes selected from the group comprising categories a–k as defined above, for example, a+b+c+d, a+b+c+e, a+b+d+e, a+c+d+e, b+c+d+e etc. Where the dataset comprises information relating to alleles of at least four genetic loci, it is preferred that at least three of the genetic loci are of categories d and e and f Information relating to polymorphisms present in these three categories is particularly useful due to the strong correlation of polymorphisms of these alleles with coronary artery disease due to the combined effects of altered micronutrient utilisation, affected adversely by alcohol metabolism, together with imbalances in fat and cholesterol metabolism. Further, where the dataset comprises information relating to alleles of at least five genetic loci, it is preferred that at least four of the genetic loci are of categories a, b, d and e. Information relating to polymorphisms present in these four categories is particularly useful due to the combined effects of micronutrients utilisation, alcohol metabolism, Phase 1 metabolism of xenobiotics and Phase II metabolism on the further metabolism and excretion of potentially harmful metabolites produced in the body (Taningher, 1999; Ulrich, 1999). Similarly, the dataset may comprise information relating to two or more alleles of at least five, for example a, b, d, e and f, six, seven, eight, nine or ten genetic loci of genes selected from the group comprising categories a–k as defined above.

Preferably, the dataset will comprise information relating to two or more alleles of one or more genetic loci of genes selected from each member of the group comprising categories a–k as described above. In a preferred embodiment, the first dataset comprises information relating to two or more alleles of the genetic loci of genes encoding each of the cytochrome P450 monooxygenase, N-acetyltransferase 1, N-acetyltransferase 2, glutathione-S-transferase, manganese superoxide dismutase, 5,10-methylenetetrahydrofolatereductase and alcohol dehydrogenase 2 enzymes. In a more preferred embodiment the first dataset further comprises information relating to two or more alleles of the genetic loci of genes encoding one or more, preferably each of epoxide hydrolase (EH), NADPH-quinone reductase (NQ01), paraxonaoase (PON1), myeloperoxidase (MPO), alcohol dehydrogenase 1, alcohol dehydrogenase 3, cholesteryl ester transfer protein, apolipoprotein A IV, apolipoprotein E, apolipoprotein C III, angiotensin, factor VII, prothrombin 20210, β-fibrinogen, heme-oxygenase-1, α-antitrypsin, SPINK1, Δ-aminolevulinacid dehydratase, interleukin 1, interleukin 1, vitamin D receptor, B1 kinin receptor, cystathionine-beta-synthase, methionine synthase (B12 MS), 5-HT transporter, transforming growth factor beta 1 (TGFβ1), L-myc, HLA Class 2 molecules, T-lymphocyte associated antigen 4 (CTLA-4), interleukin 4, interleukin 3, interleukin 6, IgA, and/or galactose metabolism gene GALT.

Genes that Encode Enzymes Responsible for (a) Detoxification of Xenobiotics in Phase I Metabolism; and (b) Conjugation Reactions in Phase II Metabolism.

Xenobiotics are potentially toxic compounds found in, for example, char-grilled red meat. Meat consumption is associated with increased risk of cancer, especially well-done meat cooked at high temperatures (Sinha, 1999). Cooking meat in this fashion leads to the production of heterocyclic amines (HCA), nitrosamines (NA), and polycyclic aromatic hydrocarbons (PAH), which have known carcinogenic activity in animals (Hirvonen, 1999; Layton, 1995).

Detoxification of xenobiotics occurs in 2 phases in humans: Phase I metabolism involves the addition of an oxygen atom or a nitrogen atom to lipophilic (fat soluble) compounds, such as steroids, fatty acids, xenobiotics (from external sources like diet, smoke, etc.) so that they can be conjugated by the Phase II enzymes (thus made water-soluble) and excreted from the body (Hirvonen, 1999). Individuals with genetic polymorphisms correlated with cancer risk in these genes should avoid consumption of char-grilled foods, smoked fish, well-done red meat whether grilled or pan-fried (Sinha, 1999). They should also increase consumption of food products known to increase Phase II metabolism so the products of Phase I metabolism may be cleared more efficiently.

Specific examples of genes of category a for which information relating to polymorphisms may be used in the present invention include genes encoding cytochrome P450 monooxygenase (CYP) e.g. CYP1A1, CYA1A2, CYP2C, CYP2D6, CYP2E1, CYP3A4, CYP11B2, genes encoding N-acetyltransferase 1 e.g. NAT1, genes encoding N-acetyltransferase 2 e.g. NAT2, genes encoding epoxide hydrolase (EH), genes encoding NADPH-quinone reductase (NQ01), genes encoding paraxonaoase (PON1), genes encoding myeloperoxidase (MPO).

CYP is also referred to as cytochromome P450 monooxygenase (gene is called CYP, enzyme is called P450). P450 enzymes belong to a super-family with wide substrate activity that catalyses the insertion of an oxygen atom into a substrate. The reaction can convert a molecule (procarcinogen) into a DNA-reactive electrophilic carcinogen (Hirvonen, 1999; Smith, 1995). Polymorphisms in genes encoding cytochrome P450 (CYP family of genes) are associated with altered susceptibility to cancer, CAD and altered metabolisim of various pharmaceutical agents (Poolsup, 2000; Miki, 1999; Cramer,2000; Marchand, 1999; Sinha, 1997).

CYP1A1 codes for a P450 enzyme that metabolises polycyclic aromatic hydrocarbons (PAH). The CYP1A1 gene is polymorphic and is inducible by PAH, which means that expression of the enzyme is increased upon exposure to PAH (MacLeod, 1997). CYP1A1 is located on chromosome 15q22–q24 (Smith, 1995). This gene has been linked to colorectal, urinary bladder, breast, oral cavity, stomach, and lung cancers (Perera, 2000; Garte, 1998). The gene product, the P450 enzyme, is inducible by exposure to the agents that it metabolises, so the consumption of high levels of a potential source of carcinogens, such as well-done red meat, would increase the production of the enzyme and thus the creation of carcinogenic substances (Mooney, 1996; Perera, 2000; Alexandrie, A. K., 2000). Studies of polymorphisms of the CYP1A1 gene have revealed considerable differences in enzyme activity, with corresponding differences in cancer risk after exposure to known substrates of the enzyme (Alexandrie, 2000; Rojas, 2000; Garte, 2000). Both the Ile-Val polymorphism I, which comprises an A4889G substitution (i.e. the adenine residue at position 4889 of the 5'-3' strand is substituted by a guanine residue) and the CYP1A1*C polymorphism, which comprises an T6235C substitution, are induced to a greater extent than the wild type gene after exposure to PAH, and have been associated with a significant increase in cancer risk (Taningher, 1999; Garte, 1998; Kawajiri, 1996; MacLeod, S., 1997; Smith, 1995). Approximately 10 percent of the Caucasian population carries polymorphisms linked to cancer risk, according to a recent American review paper (Shields, 2000). Polymorphisms in genes encoding CYP1A2, CYP2C, CYP2D6, CYP2E1, CYP3A4, CYP11B2 are associated with altered susceptibility to cancer and drug sensitivity. (Poolsup, 2000; Miki, 1999; Cramer,2000; Marchand, 1999; Sinha, 1997).

NAT1 (N-acetyltransferase 1) and NAT2 (N-acetyltransferase 2) also activate PAH and heterocyclic amines (HAA). The enzymes catalyse N-acetylation, O-acetylation, and N,O-acetylation. The O-acetylation reaction is considered the most risky, with the potential for forming chemical carcinogens that can bind to DNA. The N-acetylation reaction can occur on a compound after a P450 has inserted an oxygen, thus increasing the water solubility of the compound so it may be excreted. Due to this activity, the NAT genes are often considered as both Phase I and Phase II type enzymes. The literature describing a cancer link focuses on the activation activity of the enzymes, so they will be listed in the Phase I section only. There are 3 separate N-acetyltransferase genes in humans, two are active genes: NAT1 and NAT2, and a pseudogene, NATP. Pseudogenes have the same sequence, but lack apparent function and promoter elements and are not expressed in cells (i.e. the gene is not transcribed into RNA then translated into amino acids to make a protein/enzyme) (Perera, 2000). NAT1 and NAT2 genes are located on chromosome 8 at 8p21.3–21.1, both genes are 870 bp long and both code for a protein 290 amino acids in length. The genes are highly polymorphic and epidemiological studies have sometimes given conflicting information regarding links with cancer. The genes show geographical and ethnic variation and the enzyme activity varies considerably within different tissues or organs. There are approximately 20 polymorphisms for NAT1 known to date, but the list below only includes the polymorphisms that have shown a link to cancer (Hein, 2000a). The current list of nomenclature and polymorphisms is kept at a web site: louisville.edu/medschool/pharmacology/NAT.html. Many of the epidemiological studies of both NAT1 and NAT2 used phenotyping assays, which measured enzyme activity, and found fast and slow acetylator types, with the fast phenotype carrying an increased risk for cancer in the colon (Perera, 2000). However, later analysis of the results found that the fast/slow phenotype could vary considerably depending on the substrate chosen for acetylation (Hein, 2000a). Recent studies have used genetic sequence data to more precisely match acetylator activity and cancer risk with polymorphism (Hein, 2000b). Although the genes are the same size, they do act on different substrates. For example, caffeine is a substrate for NAT2 but not for NAT1.

NAT1 is expressed to a higher degree than NAT2 in the colon, so NAT1 may be associated with localised activity of activated HAA or PAH in the colon (Brockton, 2000; Perera, 2000). The polymorphism NAT1*10, which comprises T1088A and C1095A substitutions, and which has a fast phenotype, has been consistently linked with an increased risk of colon cancer and higher DNA adduct levels (i.e. DNA damage that can lead to cancer) in colon tissue (Perera, 2000; Ilett, 1987). The NAT1*11 polymorphism has been linked to risk of breast cancer in women who smoke or consume well-done red meat (Zheng, 1999). However, the phenotype is not well understood, so this marker cannot be categorized as a fast or slow acetylator (Doll, 1997). Two alleles of the NAT1*11 polymorphism are known: the NAT1*11A polymorphism, which comprises C(-344)T, A(-40)T, G445A, G459A, T640G, C1095A substitutions and a Δ9:1065–1090 deletion; and the NAT1*11B polymorphism, which comprises C(-344)T, A(-40)T, G445A, G459A, T640G substitutions and a Δ9:1065–1090 deletion. References to NAT1*11 polymorphisms should be understood to include reference to NAT1*11A or NAT1*11B polymorphisms.

NAT1*14 on the other hand has little or no enzyme activity (Brockton, 2000) and has been associated with increased lung cancer risk (Bouchardy, C., 1998). Two alleles of the NAT1*14 polymorphism are known: the NAT1*14A polymorphism, which comprises G560A, T1088A and C1095A substitutions; and the NAT1*14B polymorphism, which comprises a G560A substitution. References to NAT1*14 polymorphisms should, except where the context dictates otherwise, be understood to include reference to NAT1*14A or NAT1*14B polymorphisms. The NAT1*14 polymorphism shares a restriction enzyme site with the NAT1*11polymorphism, and some of the conflicting results reported in the literature are believed to be due to the inability of the assay used (restriction fragment length polymorphism assay (RFLP)) to distinguish the polymorphisms (Hein, 2000a). The oligonucleotide array suitable for use in the present invention can distinguish all polymorphisms and therefore will be more precise than the RFLP procedure. NAT2 is expressed primarily in the liver, but has been linked with cancer incidence in other organs (Hein, 2000b).

NAT2*5A, which comprises T481C and T341C substitutions, NAT2*6A, which comprises C282T and G590A substitutions, NAT2*7A, which comprises a G857A substitution, have reduced acetylation activity (Hein, 2000b) and have been linked to risk of bladder cancer (Taningher, 1999; Lee, 1998). NAT2*4, is considered the normal, or wild type, sequence. NAT2*4 has fast acetylator activity and has been linked to increased cancer risk in several studies (reviewed in Hein, 2000b; Gil, 1998), but especially in conjunction with the NAT1*10 polymorphism (Bell, 1995). NAT2 rapid/intermediate acetylators with at least one NAT2*4 allele have been linked to breast cancer in women who consumed well-done red meat (Dietz, 1999). Approximately 55% of the Caucasian population carry NAT1 polymorphisms linked to cancer. (Shields, 2000).

Polymorphisms in genes encoding epoxide hydrolase are associated with cancer and chronic obstructive pulmonary disease (Pluth, 200; Miki,1999). Polymorphisms in genes encoding NADPH-quinone reductase are associated with altered susceptibility to cancer (Nakajima, 2000). Polymorphisms in genes encoding paraxonoase are associated with altered susceptibility to cancer and to CAD (MacKness, 2000). Polymorphisms in genes encoding myeloperoxidase are associated with altered susceptibility to CAD (Schabath, 2000).

Specific examples of genes of category b for which information relating to polymorphisms may be used in the present invention include genes encoding glutathione-S-transferase e.g GSTM1, GSTP1, GSTT1.

Glutathione-S-transferases catalyse the reaction of electrophilic compounds with glutathione so the compounds may be excreted from the body. The enzymes belong to a super-family with broad and overlapping substrate specificities. Glutatione-S-transferases provide a major pathway of protection against chemical toxins and carcinogens and are thought to have evolved as an adaptive response to environmental insult, thus accounting for their wide substrate specificity (Hirvonen, 1999). There are 4 family members: alpha, mu, theta, and pi, also designated as A, M, T and P. Polymorphisms have been identified in each family (Perera, 2000). Individuals with low glutathione-S-transferase activity should avoid meats cooked at higher temperatures as above, and increase fruit and vegetable consumption. Cruciferous vegetables such as broccoli and members of the allium family such as garlic and onion have been shown to be potent inducers of these enzymes, which would be expected to increase clearance of toxic substances from the body (Cotton, 2000; Giovannucci, 1999).

GSTmu, has 3 alleles: null, a, which is considered to be the wild type, and b, which comprises a C534G substitution, with no functional difference between the a and b alleles. The GSTmu sub-type has the highest activity of the 4 types and is predominately located in the liver (Hirvonen, 1999). Approximately half of the population has a complete deletion of this gene with a corresponding risk of lung, bladder, breast, liver, and oral cavity cancer (Shields, 2000; Perera, 2000). It has been estimated that 17% of all lung and bladder cancers may be attributable to GSTM1 null genotypes (Hirvonen, 1999). GSTM1 null genotype together with a highly active CYP1A1 polymorphism has been linked to a very high cancer risk in several studies (Rojas, 2000; Shields, 2000). The GSTM1 gene is located on chromosome 1p13.3 (Cotton, 2000).

GSTpi gene is located on chromosome 11q13. This sub-type is known to metabolise many carcinogenic compounds and is the most abundant sub-type in the lungs (Hirvonen, 1999). Two single nucleotide polymorphisms have been linked to cancer to date GSTP1*B, which comprises an A313G substitution, and GSTP1*C, which comprises a C341T substitution. The enzymes of these polymorphic genes have decreased activity compared to the wild type and a corresponding increased risk of bladder, testicular, larynx and lung cancer (Harries, 1997; Matthias, 1998; Ryberg, 1997).

GSTtheta gene is on chromosome 22q11.2 and is deleted in approximately 20% of the Caucasian population. The enzyme is found in a variety of tissues, including red blood cells, liver, and lung (Potter, 1999). The deletion is associated with an increased risk of lung, larynx and bladder cancers (Hirvonen, 1999). Links with GSTM1 null genotypes are currently being searched, as it is believed that individuals that have both GSTM1 and GSTT1 alleles deleted will have a greatly increased risk of developing cancer (Potter, 1999).

Genes that Code for Enzymes that Help Cells to Combat Oxidative Stress

Specific examples of genes of category c for which information relating to polymorphisms may be used in the present invention include genes encoding manganese superoxide dismutase (MnSOD or SOD2 gene).

Manganese superoxide dismutase is an enzyme that destroys free radicals or a free-radical scavenger. The gene is located on chromosome 6q25.3, but the enzyme is found within the mitochondria of cells. There are 2 polymorphisms linked to cancer to date, an Ile 58Thr allele, which comprises an T175C substitution, and a Val(-9)Ala allele, which comprises a T(-28)C substitution,. A study of premenopausal women found a four-fold increased risk of breast cancer in individuals with the Val(-9)Ala polymorphism and the highest risk within this group is found in women who consumed low amounts of fruits and vegetables (Ambrosone, 1999). This polymorphism occurs in the signal sequence of the amino acid chain. The signal sequence ensures transport of the enzyme into the mitochondria of the cell, and so the polymorphism is believed to reduce the amount of enzyme delivered to the mitochondria (Ambrosone, 1999). The mitochondria is commonly referred to as the workhorse of the cell, where the energy-yielding reactions take place. This is the site of many oxidative reactions, so many free radicals are generated here. Individuals with low activity of this enzyme should be advised to take antioxidant supplements and increase consumption of fruits and vegetables (Giovannucci, 1999; Perera, 2000).

Genes Associated with Micronutrient Deficiency e.g. of Folate, Vitamin B12 or Vitamin B6

Specific examples of genes of category d for which information relating to polymorphisms may be used in the present invention include the gene encoding 5,10-methylenetetrahydrofolatereductase (MTHFR) activity.

5,10-methylenetetrahydrofolate reductase is active in the folate-dependent methylation of DNA precursors. Low activity of this enzyme leads to an increase of uracil incorporation into DNA (instead of thymine) (Ames, 1999). The MTHFR gene is polymorphic and has been linked to colon cancer, adult acute lymphocytic leukaemia and infant leukaemia (Ames, 1999; Perera, 2000; Potter, 2000). Both the wt and polymorphic alleles have been linked to disease, each being dependent on levels of folate in the diet. Approximately 35% of the Caucasian population has genetic polymorphisms at this locus with corresponding risk of colon cancer (Shields, 2000). Polymorphisms at this locus include those with a C677T or A1298C substitution. Dietary recommendations for individuals lacking in MTHFR activity include taking supplements with folate and increasing consumption of fruit and vegetables (Ames, 1999). Low levels of vitamins B12 and B6 have been associated with low MTHFR activity and increased cancer risk, so individuals should increase intake of these vitamins; B12 is found primarily in meat and B6 is found in whole grains, cereals, bananas, and liver (Ames, 1999). Alcohol has a deleterious effect on folate metabolism, affecting individuals with the A1298C polymorphism most severely (Ulrich, 1999). These individuals should be advised to avoid alcohol.

Genes that Code for Enzymes Responsible for Metabolism of Alcohol

Specific examples of genes of category e for which information relating to polymorphisms may be used in the present invention include genes encoding alcohol dehydrogenase e.g. the ALDH2 gene, ALDHL gene and ALDH3 gene.

Alcohol dehydrogenase 2 (ALDH2) is involved in the second step of ethanol utilisation. Reduced activity of this enzyme leads to accumulation of acetaldehyde, a potent DNA adduct former (Bosron, 1986). There has been one polymorphism identified to date, the ALDH2*2 polymorphism, which comprises a G1156A substitution, and which has links with oesophageal/throat cancer, stomach, lung, and colon cancer (IARC, 1998; Yokoyama, 1998). The advice to individuals with the polymorphism would be to avoid alcohol. Polymorphisms in ALDH1 and 3 are associated with increased susceptibility to cancers and Parkinson's disease.

Genes that Encode Enzymes Involved in Lipid and/or Cholesterol Metabolism

Specific examples of genes of category f for which information relating to polymorphisms may be used in the present invention include genes encoding cholesteryl ester transfer protein e.g. the CETP gene, polymorphisms of which genes are associated with altered susceptibility to coronary artery disease (CAD) ((Raknew, 2000; Ordovas, 2000); genes encoding apolipoprotein A, IV (ApoA-IV), polymorphisms of which genes are associated with altered susceptibility to coronary artery disease (CAD) (Wallace, 2000; Heilbronn, 2000); apolipoprotein E(ApoE), polymorphisms of which genes are associated with altered susceptibility to CAD and Alzheimer's disease (Corbo,1999; Bullido, 2000); or apolipoprotein C, III (ApoC-III), polymorphisms of which genes are associated with altered susceptibility to CAD, hypertension and insulin resistance (Salas, 1998).

Genes that Encode Enzymes Involved in Clotting Mechanisms

Specific examples of genes of category g for which information relating to polymorphisms may be used in the present invention include genes encoding angiotensin (AGT-1) and angiotensin converting enzyme (ACE), polymorphisms of which genes are associated with altered susceptibility to hypertension (Brand 2000; de Padua Mansur, 2000), factor VII, polymorphisms of which genes are associated with altered susceptibility to CAD (Donati, 2000; Di Castelnuovo, 2000); prothrombin 20210, polymorphisms of which genes are associated with altered susceptibility to venous thrombosis (Vicente, 1999); β-fibrinogen, polymorphisms of which genes are associated with altered susceptibility to CAD (Humphries, 1999); or heme-oxygenase-1, polymorphisms of which genes are associated with altered susceptibility to emphysema (Yamada, 2000).

Genes that Encode Trypsin Inhibitors

Specific examples of genes of category h for which information relating to polymorphisms may be used in the present invention include genes encoding α-antitrypsin, polymorphisms of which genes are associated with altered susceptibility to chronic obstructive pulmonary disease (COPD) (Miki, 1999); or serine protease inhibitor, Kazal type 1(SPINK), polymorphisms of which genes are associated with altered susceptibility to pancreatitis (Pfutzer, 2000).

Genes that Encode Enzymes Related to Susceptibility to Metal Toxicity

Specific examples of genes of category i for which information relating to polymorphisms may be used in the present invention include genes encoding Δ-aminolevulinacid dehydratase, polymorphisms of which genes are associated with altered susceptibility to lead toxicity (Costa, 2000).

Genes which Encode Proteins Required for Normal Cellular Metabolism and Growth

Specific examples of genes of category j for which information relating to polymorphisms may be used in the present invention include genes encoding the vitamin D receptor, polymorphisms of which genes are associated with altered susceptibility to osteoporosis, tuberculosis, Graves disease, COPD, and early periodontal disease (Ban, 2000; Wilkinson, 2000; Gelder, 2000; Miki, 1999; Hennig, 1999); the B1 kinin receptor (B1R), polymorphisms of which genes are associated with altered susceptibility to kidney disease (Zychma, 1999); cystathionine-beta-synthase, polymorphisms of which genes are associated with altered susceptibility to CAD (Tsai, 1999); methionine synthase (B12 MS), polymorphisms of which genes are associated with altered susceptibility to CAD (Tsai, 1999); the 5-HT transporter, polymorphisms of which genes are associated with altered susceptibility to neurological disorders, Alzheimer's disease, schizophrenia, other disorders of the serotonin pathway (Oliveira, 1999); tumour necrosis factor receptor 2 (TNFR2), polymorphisms of which genes are associated with altered susceptibility to CAD (Fernandez-Real, 2000); galactose metabolism gene GALT, polymorphisms of which genes are associated with altered susceptibility to ovarian cancer (Cramer, 2000); transforming growth factor beta 1 (TGFβ1), polymorphisms of which genes are associated with altered susceptibility to CAD and cancers (Yokota, 2000); and L-myc, polymorphisms of which genes are associated with altered susceptibility to CAD (especially in relation to tolerance to smoking) and cancers (Togo, 2000).

Genes which Encoded Proteins Associate with Immunological Susceptibility

Specific examples of genes of category k for which information relating to polymorphisms may be used in the present invention include genes encoding HLA Class 2 molecules, polymorphisms of which genes are associated with altered susceptibility to cervical cancer and human papilloma virus (HPV) infection (Maciag, 2000); T-lymphocyte associated antigen 4 (CTLA-4), polymorphisms of which genes are associated with altered susceptibility to liver disease (Argawal, 2000); interleukin 1 (IL-1), polymorphisms of which are associated with cardiovascular disease and periodontal disease (macaiag, 2000; Nakajima, 2000); IL-4, polymorphisms of which genes are associated with altered susceptibility to atopy and asthma (Rosa-Rosa, 1999); IL-3, polymorphisms of which genes are associated with altered susceptibility to atopy and asthma (Rosa-Rosa, 1999); IL-6, polymorphisms of which genes are associated with altered susceptibility to osteoporosis; and IgA, polymorphisms of which genes are associated with altered susceptibility to COPD (Miki, 1999).

Detection of Polymorphisms

As described above, the method of the invention may include the step of analysing a DNA sample of a human subject in order to construct the dataset to be used in the method of the invention.

Testing of Samples

Collection of Tissue Samples

DNA for analysis using the method or arrays of the invention can be isolated from any suitable client or patient cell sample. For convenience, it is preferred that the DNA is isolated from cheek (buccal) cells. This enables easy and painless collection of cells by the client, with the convenience of being able to post the sample to the provider of the genetic test without the problems associated with posting a liquid sample.

Cells may be isolated from the inside of the mouth using a disposable scraping device with a plastic or paper matrix "brush", for example, the C.E.P. Swab™ (Life Technologies Ltd., UK). Cells are deposited onto the matrix upon gentle abrasion of the inner cheek, resulting in the collection of approximately 2000 cells (Aron, 1994). The paper brush can then be left to dry completely, ejected from the handle placed into a microcentrifuge tube and posted by the client or patient to the provider of the genetic test.

Isolation of DNA from Samples

DNA from the cell samples can be isolated using conventional procedures. For example DNA may be immobilised onto filters, column matrices, or magnetic beads. Numerous commercial kits, such as the Qiagen QIAamp kit (Quiagen, Crawley, UK) may be used. Briefly, the cell sample may be placed in a microcentrifuge tube and combined with Proteinase K, mixed, and allowed to incubate to lyse the cells. Ethanol is then added and the lysate is transferred to a QIAamp spin column from which DNA is eluted after several washings.

The amount of DNA isolated by the particular method used may be quantified to ensure that sufficient DNA is available for the assay and to determine the dilution required to achieve the desired concentration of DNA for PCR amplification. For example, the desired target DNA concentration may be in the range 10 ng and 50 ng. DNA concentrations outside this range may impact the PCR amplification of the individual alleles and thus impact the sensitivity and selectivity of the polymorphism determination step.

The quantity of DNA obtained from a sample may be determined using any suitable technique. Such techniques are well known to persons skilled in the art and include UV (Maniatis, 1982) or fluorescence based methods. As UV methods may suffer from the interfering absorbance caused by contaminating molecules such as nucleotides, RNA, EDTA and phenol and the dynamic range and sensitivity of this technique is not as great as that of fluorescent methods, fluorescence methods are preferred. Commercially available fluorescence based kits such as the PicoGreen dsDNA Quantification (Molecular Probes, Eugene, Oreg., USA).

Primers

Prior to the testing of a sample, the nucleic acids in the sample may be selectively amplified, for example using Polymerase Chain Reaction (PCR) amplification, as described in U.S. Pat. Nos. 4,683,202 AND 4,683,195.

Preferred primers for use in the present invention are from 18 to 23 nucleotides in length, without internal homology or primer-primer homology.

Furthermore, to ensure amplification of the region of interest and specificity, the two primers of a pair are preferably selected to hybridise to either side of the region of interest so that about 150 bases in length are amplified, although amplification of shorter and longer fragments may also be used. Ideally, the site of polymorphism should be at or near the centre of the region amplified.

Table 1 provides preferred examples of primer pairs which may be used in the invention, particularly when the Taqman® assay is used in the method of the invention. The primers are shown together with the gene targets and preferred examples of the wt probes and polymorphism probes used in the Taqman® assay for each gene target.

Table 2 provides preferred examples of the primer pairs which may be used in the invention together with the gene targets and the size of the fragment isolated using the primers, which they amplify.

The primers and primer pairs form a further aspect of the invention. Therefore the invention provides a primer having a sequence selected from SEQ ID NO: 86–99, 104–163. In another aspect, there is provided a primer pair comprising primers having SEQ ID NO:n, where n is an even number from 86–98 or 104–162 in conjunction with a primer having SEQ ID NO: (n+1).

In a preferred embodiment of the invention, multiplexed amplification of a number of sequences are envisioned in order to allow determination of the presence of a plurality of polymorphisms using, for example the DNA array method. Therefore, primer pairs to be used in the same reaction are preferably selected by position, similarity of melting temperature, internal stability, absence of internal homology or homology to each other to prevent self-hybridisation or hybridisation with other primers and lack of propensity of each primer to form a stable hairpin loop structure. Thus, the sets of primer pairs to be coamplified together preferably have approximately the same thermal profile, so that they can be effectively coamplified together. This may be achieved by having groups of primer pairs with approximately the same length and the same G/C content.

Therefore in a further aspect of the invention, there is provided a primer set comprising at least 5, more preferably 10, 15 primer pairs selected from SEQ ID NO: 86–121.

TABLE 1

| Gene | Forward primer | Reverse primer | WT Probe | Polymorphism probe |
|---|---|---|---|---|
| 1. CYP1A1 | | | | |
| A4889G | CATGGGC (SEQ ID NO:122) AAGCGGAAGTG | CAGGAT (SEQ ID NO:123) AGCCAGGAAGAGAAAGAC | CGGTGA (SEQ ID NO:164) GACCaTTC | CGGTGA (SEQ ID NO:165) GACCgTTC |
| T6235C | AGACAGG (SEQ ID NO:124) GTCCCCAGGTCAT | CAGAGG (SEQ ID NO:125) CTGAGGTGGAGAA | CTCCAC (SEQ ID NO:166) CTCCtGGG | CTCCAC (SEQ ID NO:167) CTCCcGGG |
| 2. NAT1 | | | | |
| G445A | GGAGTTA (SEQ ID NO:126) ATTTCTGGGAAGGATCAG | TGGTCT (SEQ ID NO:127) AGATACCAGAATCCATTCTCTT | GCCTTG (SEQ ID NO:168) TgTCTTC | TGCCTT (SEQ ID NO:169) CTaTCTTC |
| G459A | GCCAGCC (SEQ ID NO:128) TCTGGAGTTAATTTCT | TTCCCT (SEQ ID NO:129) TCTGATTTGGTCTAGATACC | CGTTTG (SEQ ID NO:170) ACgGAAGAG | CGTTTG (SEQ ID NO:171) ACaGAAGAG |
| G560A | GGGAACA (SEQ ID NO:130) GTACATTCCAAATGAAGA | TGTTCG (SEQ ID NO:131) AGGCTTAAGAGTAAAGGAGT | AATACC (SEQ ID NO:172) gAAAAATC | CAAATA (SEQ ID NO:173) CCaAAAAAT |
| T640G | AACAATT (SEQ ID NO:132) GAAGATTTTGAGTCTATGAATACA | TCTGCA (SEQ ID NO:133) AGGAACAAAATGATTTACTAGT | CATCTC (SEQ ID NO:174) CADCATCTG | ACATCT (SEQ ID NO:175) CCAgCATCT |
| T1088A | GAAACAT (SEQ ID NO:134) AACCACAAACCTTTTCAAA | AAATCA (SEQ ID NO:135) CCAATTTCCAAGATAACCA | CCATCT (SEQ ID NO:203) TTAAAATACATTTaTTA | CATCTT (SEQ ID NO:204) TAAAATACATTTtTTA |
| C1095A | AAACATA (SEQ ID NO:136) ACCACAAACCTTTTCAAATAAT | AAATCA (SEQ ID NO:137) CCAATTTCCAAGATAACCA | GCCATC (SEQ ID NO:176) TTTAAAAgACAT | GCCATC (SEQ ID NO:177) TTTAAAAtACATT |
| 3. NAT2 | | | | |
| C>T | AATCAAC (SEQ ID NO:138) TTCTGTACTGGGCTCTGA | CCATGC (SEQ ID NO:139) CAGTGCTGTATTTGTT | AGGGTA (SEQ ID NO:178) TTTTTAcATCCCT | AGGGTA (SEQ ID NO:179) TTTTTAtATCCCTC |
| C>T2 | TGCATTT (SEQ ID NO:140) TCTGCTTGACAGAAGA | TTTGTT (SEQ ID NO:141) TGTAATATACTGCTCTCTCCT GAT | TCTGGT (SEQ ID NO:180) ACCTGGACCAA | AATCTG (SEQ ID NO:181) GTACtTGGACCAA |
| G>A | GCCAAAG (SEQ ID NO:142) AAGAAACACCAAAAAAT | AATGA (SEQ ID NO:143) TGTGGTTATAAATGAAGATGT TG | TGAACC (SEQ ID NO:182) TCgAACAAT | TTGAAC (SEQ ID NO:183) CTCaAACAATT |
| G>A2 | AAGAGGT (SEQ ID NO:144) TGAAGAAGTGCTGAAAAATAT | ATACAT (SEQ ID NO:145) ACACAAGGGTTTATTTTGTTC CT | CTGGTG (SEQ ID NO:184) ATGgATCC | CTGGTG (SEQ ID NO:185) ATGaATCC |
| 4. GSTM1 | | | | |
| C534G | GTTCCAG (SEQ ID NO:146) CCCACACATTCTTG | CGGGAG (SEQ ID NO:147) ATGAAGTCCTTCAGATT | CAAGCA (SEQ ID NO:186) gTTGGGC | CAAGCA (SEQ ID NO:187) cTTGGGC |
| 5. GSTP1 | | | | |
| A313G | CCTGGTG (SEQ ID NO:148) GACATGGTGAATG | GCAGAT (SEQ ID NO:149) GCTCACATAGTTGGTGTAG | GCAAAT (SEQ ID NO:188) ACaTCTCCCT | GCAAAT (SEQ ID NO:189) ACgTCPCCCT |
| C341T | GGGATGA (SEQ ID NO:150) GAGTAGGATGATACATGGT | GGGTCT (SEQ ID NO:151) CAAAAGGCTTCAGTTG | CCTTGC (SEQ ID NO:190) CCgCCTC | CTTGCC (SEQ ID NO:191) CaCCTCC |
| 6. GSTT1 | TCATTCT (SEQ ID NO:152) GAAGGCCAAGGACTT | CAGGGC (SEQ ID NO:153) ATCAGCTTCTGCTT | CCTGCA (SEQ ID NO:192) GACCCC | N/A |
| 7. MnSOD | | | | |
| T-28C | GGCTGTG (SEQ ID NO:154) CTTTCTCGTCTTCA | TTCTGC (SEQ ID NO:155) CTGGAGCCCAGAT | ACCCCA (SEQ ID NO:193) AAaCCGGA | ACCCCA (SEQ ID NO:194) AAgCCGGA |
| T175C | GTGTTGC (SEQ ID NO:156) ATTTACTTCAGGAGATGTT | TCCAGA (SEQ ID NO:157) AAATGCTATGATTGATATGAC | AGCCCA (SEQ ID NO:195) GAtAGCT | AGCCCA (SEQ ID NO:196) GAcAGCT |
| 8. MTHFR | | | | |
| C677T | GACCTGA (SEQ ID NO:158) AGCACTTGAAGGAGAA | TCAAAG (SEQ ID NO:159) AAAAGCTGCGTGATGA | AAATCG (SEQ ID NO:197) gCTCCCGC | AAATCG (SEQ ID NO:198) aCTCCCGCAGA |
| A1298C | AAGAGCA (SEQ ID NO:160) AGTCCCCCAAGGA | CTTTGT (SEQ ID NO:161) GACCATTCCGGTTTG | CAGTGA (SEQ ID NO:199) AGaAAGTGTC | AGTGAA (SEQ ID NO:200) GcAAGTGTC |
| 9. ALDH2 | | | | |
| G1156A | CCCTTTG (SEQ ID NO:162) GTGGCTACAAGATGT | AGACCC (SEQ ID NO:163) TCAAGCCCCAACA | TCACAG (SEQ ID NO:201) TTTTCACTTcAGTGT | TCACAG (SEQ ID NO:202) TTTTCACTTtAGTGT |

TABLE 2

Examples of Primer pairs

| Gene | Primer Set | | Reverse | Size |
|---|---|---|---|---|
| NAT1 | 1 | N/A same genotype as set 3 | | |
| | 2 | N/A same genotype as set 3 | | |
| | 3 | 5'ggg ttt gga cgc tca tac c (SEQ ID NO:86) | 5'aat gta ctg ttc cct tct gat ttg g (SEQ ID NO:87) | 141 bp |
| | 4b | 5'tcc gtt tga cgg aag aga at (SEQ ID NO:88) | 5'ggg tct gca gga aac aaa at (SEQ ID NO:89) | 234 bp |
| | 5 | 5'gaa aca taa cca caa acc (SEQ ID NO:90) | 5'caa caa taa acc aac att aaa agc (SEQ ID NO:91) | 241 bp |

TABLE 2-continued

Examples of Primer pairs

| Gene | Primer Set | | Reverse | Size |
|---|---|---|---|---|
| NAT2 | 1 | 5'act tct gta ctg ggc tcc gac c (SEQ ID NO:92) | 5'gca tcg aca atg taa ttc ctg c (SEQ ID NO:93) | 150 bp |
| | 2 | 5'aat aca gca ctg gca tgg (SEQ ID NO:94) | 5'caa gga aca aaa tga tgt gg (SEQ ID NO:95) | 380 bp |
| | 3 | 5'gtg ggc ttc atc ctc acc ta (SEQ ID NO:96) | 5'ggg tga cac ata cac aag ggt ct (SEQ ID NO:97) | 209 bp |
| GSTM1 | 1 | 5'cag ccc aca cat tct tgg (SEQ ID NO:98) | 5'aag cgg gag atg aag tcc (SEQ ID NO:99) | 196 bp |
| MTHFR | 1 | 5'agg tta ccc caa agg cca cc (SEQ ID NO:100) | 5'gca agt gat gcc cat gtc g (SEQ ID NO:101) | 166 bp |
| | 2 | 5'tct tct acc tga aga gca agt cc (SEQ ID NO:102) | 5'caa gtc act ttg tga cca ttc c (SEQ ID NO:103) | 142 bp |
| CYP1A1 | 1b | 5'cct gaa ctg cca ctt cag c (SEQ ID NO:104) | 5'cca gga aga gaa aga cct cc (SEQ ID NO:105) | 199 bp |
| | 2 | 5'ccc att ctg tgt ttg ggt ttt t (SEQ ID NO:106) | 5'aga ggc tga ggt ggg aga at (SEQ ID NO:107) | 213 bp |
| GSTT1 | 1 | 5'gag gtc att ctg aag gcc aag g (SEQ ID NO:108) | 5'ttt gtg gac tgc tga gga cg (SEQ ID NO:109) | 133 bp |
| β-actin | 1b | 5'tcc tca gac cat tgc tc (SEQ ID NO:110) | 5'taa cgc aac taa gtc ata gtc c (SEQ ID NO:111) | 175 bp |
| MuSOD | 1 | 5'ggc tgt gct ttc tcg tct tc (SEQ ID NO:112) | 5'ggt gac gtt cag gtt gtt ca (SEQ ID NO:113) | 194 bp |
| | 2 | 5'aca gtg gtt gaa aaa gta gg (SEQ ID NO:114) | 5'caa aat gta gat aag ggt gc (SEQ ID NO:115) | 205 bp |
| ALDH2 | 1 | 5'ttg gtg gct aca aga tgt cg (SEQ ID NO:116) | 5'agg tcc tga act tcc agc ag (SEQ ID NO:117) | 345 bp |
| GSTP1 | 1 | 5'gct cta tgg gaa gga cca gc (SEQ ID NO:118) | 5'aag cca cct gag ggg taa gg (SEQ ID NO:119) | 192 bp |
| | 2 | 5'cag cag ggt ctc aaa agg (SEQ ID NO:120) | 5'gat gga cag gca gaa tgg (SEQ ID NO:121) | 250 bp |

Having obtained a sample of DNA, preferably with amplified regions of interest, individual polymorphisms may be identified. Identification of the markers for the polymorphisms involves the discriminative detection of allelic forms of the same gene that differ by nucleotide substitution, or in the case of some genes, for example the GSTM1 and GSTT1 genes, deletion of the entire gene. Methods for the detection of known nucleotide differences are well known to the skilled person. These may include, but are not limited to:

a. Hybridization with allele-specific oligonucleotides (ASO), (Wallace, 1981; Ikuta, 1987; Nickerson, 1990, Varlaan, 1986, Saiki, 1989 and Zhang, 1991).
b. Allele specific PCR, (Newton 1989, Gibbs, 1989).
c. Solid-phase minisequencing (Syvanen, 1993).
d. Oligonucleotide ligation assay (OLA) (Wu, 1989, Barany, 1991; Abravaya, 1995).
e. The 5' fluorogenic nuclease assay (Holland, 1991 & 1992, Lee, 1998, U.S. Pat. Nos. 4,683,202, 4,683,195, 5,723,591 and 5,801,155).
f. Restriction fragment length polymorphism (RFLP), (Donis-Keller, 1987).

In a preferred embodiment, the genetic loci are assessed via a specialised type of PCR used to detect polymorphisms, commonly referred to as the Taqman® assay and performed using an AB7700 instrument (Applied Biosystems, Warrington, UK). In this method, a probe is synthesised which hybridises to a region of interest containing the polymorphism. The probe contains three modifications: a fluorescent reporter molecule, a fluorescent quencher molecule and a minor groove binding chemical to enhance binding to the genomic DNA strand. The probe may be bound to either strand of DNA. For example, in the case of binding to the coding strand, when the Taq polymerase enzyme begins to synthesise DNA from the 5' upstream primer, the polymerase will encounter the probe and begin to remove bases from the probe one at a time using a 5'-3' exonuclease activity. When the base bound to the fluorescent reporter molecule is removed, the fluorescent molecule is no longer quenched by the quencher molecule and the molecule will begin to fluoresce. This type of reaction can only take place if the probe has hybridised perfectly to the matched genomic sequence. As successive cycles of amplification take place, i.e. more probes and primers are bound to the DNA present in the reaction mixture, the amount of fluorescence will increase and a positive result will be detected. If the genomic DNA does not have a sequence that matches the probe perfectly, no fluorescent signal is detected.

Examples of oligonucleotide probes which may be used in the invention, particularly when the Taqman® assay is used in the method of the invention together with primers which may be used. These oligonucleotide probes form another aspect of the present invention.

Therefore in a further aspect of the invention, there is provided an oligonucleotide having a sequence selected from SEQ ID NO: 164–202. The invention further provides a set of oligonucleotides comprising at least 5, 10, 20, 30, 40, 50, 60 or 70 oligonucleotides selected from the group comprising SEQ ID NO:164–202.

Arrays

In a preferred embodiment of the invention, hybridisation with allele specific oligonucleotides is conveniently carried out using oligonucleotide arrays, preferably microarrays, to determine the presence of particular polymorphisms.

Such microarrays allow miniaturisation of assays, e.g. making use of binding agents (such as nucleic acid sequences) immobilised in small, discrete locations (microspots) and/or as arrays on solid supports or on diagnostic chips. These approaches can be particularly valuable as they can provide great sensitivity (particularly through the use of fluorescent labelled reagents), require only very small amounts of biological sample from individuals being tested and allow a variety of separate assays to be carried out simultaneously. This latter advantage can be useful as it provides an assay for different a number of polymorphisms of one or more genes to be carried out using a single sample. Examples of techniques enabling this miniaturised technology are provided in WO84/01031, WO88/1058, WO89/01157, WO93/8472, WO95/18376/WO95/18377, WO95/24649 and EP-A-0373203, the subject matter of which are herein incorporated by reference.

DNA microarrays have been shown to provide appropriate discrimination for polymorphism detection. Yershov, 1996; Cheung, 1999 and Schena 1999 have described the principles of the technique. In brief, the DNA microarray may be generated using oligonucleotides that have been selected to hybridise with the specific target polymorphism. These oligonucleotides may be applied by a robot onto a predetermined location of a glass slide, e.g. at predetermined X, Y Cartesian coordinates, and immobilised. The PCR product (e.g. fluorescently labelled RNA or DNA) is introduced on to the DNA microarray and a hybridisation reaction conducted so that sample RNA or DNA binds to complementary sequences of oligonucleotides in a sequence-specific manner, and allow unbound material to be washed away. Gene target polymorphisms can thus be detected by their ability to bind to complementary oligonucleotides on the array and produce a signal. The absence of a fluorescent signal for a specific oligonucleotide probe indicates that the client does not have the corresponding polymorphism. Of course, the method is not limited to the use of fluorescence labelling but may use other suitable labels known in the art. the fluorescence at each coordinate can be read using a suitable automated detector in order to correlate each fluorescence signal with a particular oligonucleotide.

Oligonucleotides for use in the array may be selected to span the site of the polymorphism, each oligonucleotide comprising one of the following at a central location within the sequence:

a. wild-type or normal base at the position of interest in the leading strand
b. wild-type or normal base at the position of interest in the lag (non-coding) strand
c. altered base at the position of interest in the leading strand
d. altered complementary base at the position of interest in the lag strand The arrays used in the present method form another independent aspect of the present invention. Arrays of the invention comprise a set of two or more oligonucleotides, each oligonucleotide being specific to a sequence comprising one or more polymorphisms of a gene selected from the group comprising categories a–k as defined above.

Preferably, the array will comprise oligonucleotides each being specific to a sequence comprising one or more polymorphisms of an individual gene of at least two different categories a–k as defined above, for example a+b (i.e. at least one oligonucleotide specific for a sequence comprising one or more polymorphisms of a first gene, the first gene being of category a and at least one oligonucleotide specific for a sequence comprising one or more polymorphisms of a second gene, the second gene being of category b), a+c, a+d, a+e, a+f, a+g, a+h, a+i, a+j, a+k, b+c, b+d, b+e etc., c+d, c+e etc., d+e, d+f etc., e+f, e+g etc., f+g, f+h etc., g+h, g+i, g+k, h+i, h+k. Where the array comprises two or more oligonucleotides, it is preferred that at least one of the oligonucleotides is an oligonucleotide specific for a sequence of a polymorphism of a gene of category d, due to the central role of micronutrients in the maintenance of proper cellular growth and DNA repair, and due to the association of micronutrient metabolism or utilisation disorders with several different types of diseases (Ames 1999; Perera, 2000; Potter, 2000). More preferably, the array will comprise oligonucleotides each being specific to a sequence comprising one or more polymorphisms of an individual gene of at least three different categories a–k as defined above, for example, a+b+c, a+b+d, a+b+e, a+b+f, a+b+g, a+b+h, a+b+i, a+b+j, a+b+k a+c+d, a+c+e etc, a+d+e, etc, b+c+d, etc, c+d+e etc, d+e+f etc, and all other combinations of three categories. Where the array comprises three or more oligonucleotides, it is preferred that at least two of the oligonucleotides are oligonucleotides specific for a sequence of a polymorphism of a gene of categories d and e. Information relating to polymorphisms present in both of these categories is particularly useful due to the effects of alcohol consumption and metabolism on the efficiency of enzymes related to micronutrient metabolism and utilisation.(Ulrich, 1999). In a further preferred embodiment where the array comprises three or more oligonucleotides, it is preferred that at least two of the oligonucleotides are oligonucleotides specific for a sequence of a polymorphism of a gene of c categories a and b due to the close interaction of Phase I and Phase II enzymes in the metabolism of xenobiotics. Even more preferably, the array will comprise oligonucleotides each being specific to a sequence comprising one or more polymorphisms of an individual gene of at least four different categories a–k as defined above, for example, a+b+c+d, a+b+c+e, a+b+d+e, a+c+d+e, b+c+d+e etc. Where the array comprises four or more oligonucleotides, it is preferred that at least three of the oligonucleotides are oligonucleotides specific for a sequence of a polymorphism of a gene of categories d and e and f Information relating to polymorphisms present in these three categories is particularly useful due to the strong correlation of polymorphisms of these alleles with coronary artery disease due to the combined effects of altered micronutrient utilisation, affected adversely by alcohol metabolism, together with imbalances in fat and cholesterol metabolism. Where the array comprises five or more oligonucleotides, it is preferred that at least four of the oligonucleotides are oligonucleotides specific for a sequence of a polymorphism of a gene of categories a, b, d and e. Information relating to polymorphisms present in these four categories is particularly useful due to the combined effects of micronutrients utilisation, alcohol metabolism, Phase 1 metabolism of xenobiotics and Phase II metabolism on the further metabolism and excretion of potentially harmful metabolites produced in the body (Taningher, 1999; Ulrich, 1999). Similarly, the array may comprise oligonucleotides each being specific to a sequence comprising one or more polymorphisms of an individual gene of at least five, for example a, b, d, e and f, six, seven, eight, nine or ten different categories a–k as defined above.

Most preferably, the array will comprise oligonucleotides each being specific to a sequence comprising one or more polymorphisms of an individual gene of each of categories a–k as defined above.

In one preferred embodiment, the array comprises oligonucleotides each being specific to a sequence comprising one or more polymorphisms of individual genes, the individual genes comprising each member of the group comprising genes encoding cytochrome P450 monooxygenase, N-acetyltransferase 1, N-acetyltransferase 2, glutathione-S-transferase, manganese superoxide dismutase, 5,10-methylenetetrahydrofolatereductase and alcohol dehydrogenase 2 enzymes. genetic loci of genes encoding each of the cytochrome P450 monooxygenase, N-acetyltransferase 1, N-acetyltransferase 2, glutathione-S-transferase, manganese superoxide dismutase, 5,10-methylenetetrahydrofolatereductase and alcohol dehydrogenase 2 enzymes. In a more preferred embodiment the array further comprises oligonucleotides specific for one or more alleles of the genetic loci of genes encoding one or more, preferably each of epoxide hydrolase (EH), NADPH-quinone reductase (NQ01), paraxonaoase (PON1), myeloperoxidase (MPO), alcohol dehydrogenase 1, alcohol dehydrogenase 3, cholesteryl ester transfer protein, apolipoprotein A IV, apolipoprotein E, apolipoprotein C III, angiotensin, factor VII, prothrombin 20210, β-fibrinogen, heme -oxygenase-1, α-antitrypsin, SPINK1, Δ-aminolevulinacid dehydratase, interleukin 1, interleukin 1, vitamin D receptor, B1 kinin receptor, cystathionine-beta-synthase, methionine synthase (B12 MS), 5-HT transporter, transforming growth factor beta 1 (TGFβ1), L-myc, HLA Class 2 molecules, T-lymphocyte associated antigen 4 (CTLA-4), interleukin 4, interleukin 3, interleukin 6, IgA, and/or galactose metabolism gene GALT.

In preferred arrays, the oligonucleotides in the array comprise at least 5, 10, 20, 30, 40, 50, 60 or 70 oligonucleotides selected from the group comprising SEQ ID NO:1–SEQ ID NO: 85 illustrated in TABLE 3 which shows preferred oligonucleotides listed in the right column with the primer set used to amplify the appropriate fragments of sample DNA listed in the left column.

In a preferred embodiment the array will comprise all of the oligonucleotides SEQ ID NO:1–85.

TABLE 3

| Gene Target | 25 nt sequence |
|---|---|
| 1. CYP1A1 | |
| Primer set1 A4889G wt-lead | 5' atc ggt gag acc Att gcc cgc tgg g (SEQ ID NO:1) |
| Primer set1 A4889G wt-lag | 5' ccc agc ggg caa Tgg tct cac cga t (SEQ ID NO:2) |
| Primer set1 A4889G polymorph-lead | 5' atc ggt gag acc Gtt gcc cgc tgg g (SEQ ID NO:3) |
| Primer set1 A4889G polymorph-lag | 5' ccc agc ggg caa Cgg tct cac cga t (SEQ ID NO:4) |
| Primer set2 T6235C wt-lead | 5' acc tcc acc tcc Tgg gct cac acg a (SEQ ID NO:5) |
| Primer set2 T6235C wt-lag | 5' tcg tgt gag ccc Agg agg tgg agg t (SEQ ID NO:6) |
| Primer set2 T6235C polymorph-lead | 5' acc tcc acc tcc Cgg gct cac acg a (SEQ ID NO:7) |
| Primer set2 T6235C polymorph-lag | 5' tcg tgt gag ccc Ggg agg tgg agg t (SEQ ID NO:8) |
| 2. NAT1 | |
| Primer set1 | N/A |
| Primer set2 | N/A |
| Primer set 3 G445A wt-lead | 5'cag gtg cct tgt Gtc ttc cgt ttg a (SEQ ID NO:9) |
| Primer set3 G445A wt-lag | 5' tca aac gga aga Cac aag gca cct g (SEQ ID NO:10) |
| Primer set3 G445A polymorph-lead | 5' cag gtg cct tgt Atc tcc cgt ttg a (SEQ ID NO:11) |
| Primer set3 G445A polymorph-lag | 5' tca aac gga aga Tac aag gca cct g (SEQ ID NO:12) |
| Primer set3 G459A wt-lead | 5' cct ccg tct gac Gga aga gaa tgg a (SEQ ID NO:13) |
| Primer set3 G459A wt-lag | 5' tcc att ctc ttc Cgt caa acg gaa g (SEQ ID NO:14) |
| Primer set3 G459A polymorph-lead 5' | 5' ctt ccg ttt gac Aga aga gaa tgg a (SEQ ID NO:15) |
| Primer set3 G459A polymorph-lag | 5' tcc att ctc ttc Tgt caa acg gaa g (SEQ ID NO:16) |
| Primer set4 G560A wt-lead | 5' aca gca aat acc Gaa aaa tct act c (SEQ ID NO:17) |
| Primer set4 G560A wt-lag | 5' gag tag att ttt Cgg tat ttg ctg t (SEQ ID NO:18) |
| Primer set4 G560A polymorph-lead | 5' aca gca aat acc Aaa aaa tct act c (SEQ ID NO:19) |
| Primer set4 G560A polymorph-lag | 5' gag tag att ttt Tcc tat ttg ctg t (SEQ ID NO:20) |
| Primer set5T1088A wt-lead*a | 5' taa taa taa taa Taa atg tct ttt a (SEQ ID NO:21) |
| Primer set5 T1088A wt-lag*a | 5' taa aag aca ttt Att att att att a (SEQ ID NO:22) |
| Primer set5T1088A wt-lead*b | 5' taa taa taa taa Taa atg tat ttt a (SEQ ID NO:23) |
| Primer set5 T1088A wt-lag*b | 5' taa aat aca ttt Att att tta att a (SEQ ID NO:24) |
| Primer set5 T1088Apolymorph-lead*a | 5' taa taa taa taa Aaa atg tct ttt a (SEQ ID NO:25) |
| Primer set5 T1088A polymorph-lag*a | 5' taa aag aca ttt Ttt att tta att a (SEQ ID NO:26) |
| Primer set5 T1088Apolymorph-lead*b | 5' taa taa taa taa Aaa atg tat ttt a |
| Primer set5 T1088A polymorph-lag*a | 5' taa aat aca ttt Ttt att tta att a (SEQ ID NO:27) |
| *redundancy due to adjacent polymorphisms | |
| Primer set5 C1095A wt-lead*a | 5' aat aat aaa tgt Ctt tta aag atg g (SEQ ID NO:28) |
| Primer set5 C1095A wt-lag*a | 5' cca cct tta aaa Gac att tat tat t (SEQ ID NO:29) |
| Primer set5 C1095A wt-lead*b | 5' aat aaa aaa tgt Ctt tta aag atg g (SEQ ID NO:30) |
| Primer set5 C1095A wt-lag*b | 5' cca tct tta aaa Gac att ttt tat t (SEQ ID NO:31) |
| Primer set5 C1095Apolymorph-lead*a | 5' aat aat aaa tgt Att tta aag atg g (SEQ ID NO:32) |
| Primer set5 C1095A polymorph-lag*a | 5' cca tct tta aaa Tac att tat tat t (SEQ ID NO:33) |
| Primerset5 C1095Apolymorph-lead*b | 5' aat aaa aaa tgt Att tta aag atg g (SEQ ID NO:34) |
| Primer set5 C1095A polymorph-lag*b | 5' cca tct tta aaa Tac att ttt tat t (SEQ ID NO:35) |
| *redundancy due to adjacent polymorphisms | |
| 3. NAT2 | |

TABLE 3-continued

| Gene Target | 25 nt sequence |
|---|---|
| Primer set1 C282T wt-lead | 5' agg gcc ttt tta Cat ccc tcc agt t (SEQ ID NO:36) |
| Primer set1 C282T wt-lag | 5' aac tgg agg gat Gta aaa atc ccc t (SEQ ID NO:37) |
| Primer set1 C282T polymorph-lead | 5' agg gta ttt tta Tat ccc tcc cgt c (SEQ ID NO:38) |
| Primer set1 C282T polymorph-lag | 5' aac tgg agg gat Atc aaa ata ccc t (SEQ ID NO:39) |
| Primer set2 C481T wt-lead | 5' gga atc tgg tac Ctg gac caa atc a (SEQ ID NO:40) |
| Primer set2 C481T wt-lag | 5' tga ttt ggt cca Ggt acc aga ttc c (SEQ ID NO:41) |
| Primer set2 C481T polymorph-lead | 5' gga atc tgg tac Ttg gac caa atc a (SEQ ID NO:42) |
| Primer set2 C481T polymorph-lag | 5' tga ttt ggt cca Agt acc aga ttc c (SEQ ID NO:43) |
| Primer set2 GS90A wt-lead | 5' cgc ttg acc ctc Gaa caa ttg aag a (SEQ ID NO:44) |
| Primer set2 GS90A wt-lag | 5' tct tca att gtt Cga ggt tca agc g (SEQ ID NO:45) |
| Primer set2 G590A polymorph-lead | 5' cgc ttg aac ctc Aaa caa ttg aag a (SEQ ID NO:46) |
| Primer set2 G590A polymorph-lag | 5' tct tca att gtt Tga ggt tca agc g (SEQ ID NO:47) |
| Primer set3 G857A wt-lead | 5' aac ctg gtg atg Gat ccc tta cta t (SEQ ID NO:48) |
| Primer set3 G857A wt-lag | 5' ata gta agg gat Cca tca cca ggt t (SEQ ID NO:49) |
| Primer set3 G857A polymorph-lead | 5' aac ctg gtg atg Aat ccc tta cta t (SEQ ID NO:50) |
| Primer set3 G857A polymorph-lead | 5' ata gta agg gat Tca tca cca ggt t (SEQ ID NO:51) |
| 4. GSTM1 | |
| Primer set1 wt-lead | 5'gct aca ttg ccc gca agc aca acc t (SEQ ID NO:52) |
| Primer set1 wt-lag | 5' agg ttg tgc ttg cgg gca atg tag c (SEQ ID NO:53) |
| 5. GSTP1 | |
| Primer set1 A313G wt-lead | 5' cgc tgc aaa tac Atc tcc ctc atc t (SEQ ID NO:54) |
| Primer set1 A313G wt-lag | 5' aga tga ggg aga Tgt att tgc agc g (SEQ ID NO:55) |
| Primer set1 A313G polymorph-lead | 5' cgc tgc aaa tac Gtc tcc ctc atc t (SEQ ID NO:56) |
| Primer set1 A313G polymorph-lag | 5' aga tgc ggg agc Cgt att tgc agc g (SEQ ID NO:57) |
| Primer set2 C341T wt-lead | 5' tct ggc agg agg Cgg gca agg atg a (SEQ ID NO:58) |
| Primer set2 C341T wt-lag | 5' tca tcc ttg ccc Gcc tcc tgc cag a (SEQ ID NO:59) |
| Primer set2 C341T polymorph-lead | 5' tct ggc cgg agg Tgg gca agg atg a (SEQ ID NO:60) |
| Primer set2 C341T polymorph-lag | 5' tca tcc ttg ccc Acc tcc tgc cag a (SEQ ID NO:61) |
| 6. GSTT1 | |
| Primer set1 wt-lead | 5' acc ata aag cag aag ctg atg ccc t (SEQ ID NO:62) |
| Primer set2 wt-lag | 5' agg gca tca gct tct gct tta tgg t (SEQ ID NO:63) |
| 7. MnSOD | |
| Primer set1 T-26C wt-lead | 5' agc tgg ctc cgg Ttt tgg ggc atc t (SEQ ID NO:64) |
| Primer set1 T-26Cwt lag | 5' aga tac ccc aaa Acc gga gcc agc t (SEQ ID NO:65) |
| Primer set1 T-26C polymorph-lead | 5' agc tgg ctc ccg Ctt tgg ggt atc t (SEQ ID NO:66) |
| Primer set1 T-26C polymorph-lag | 5' aga tac ccc aaa Gcc gga gcc agc t (SEQ ID NO:67) |
| Primer set2 T175C wt-lead | 5' tta cag ccc aga Tag ctc ttc agc c (SEQ ID NO:68) |
| Primer set2 T175C wt-lag | 5' ggc cga aga gct Atc tgg gct gta a (SEQ ID NO:69) |
| Primer set2 T175C polymorph-lead | 5' tta cag ccc aga Cag ctc ttc agc c (SEQ ID NO:70) |
| Primer set2 T175O polymorph-lag | 5' ggc tga aga gct Gtc tgg gct gta a (SEQ ID NO:71) |
| 8. MTHFR | |
| Primer set1 C677T wt-lead | 5' tgt ctg cgg gag Ccg att tca cca t (SEQ ID NO:72) |
| Primer set1 C677T wt-lag | 5' atg atg aaa tcg Gct ccc gca gac a (SEQ ID NO:73) |
| Primer set1 C677T polymorph-lead | 5' tgt ctg cgg gag Tcg att tca tca t (SEQ ID NO:74) |
| Primer set1 C677T polymorph-lag | 5' atg atg aaa tcg Act ccc gca gac a (SEQ ID NO:75) |
| Primer set2 A1298C wt-lead | 5' tga cca gtg aag Aaa gtg tct ttg a (SEQ ID NO:76) |
| Primer set2 A1298C wt-lag | 5' tca aag aca ctt Tct tca ctg gtc a (SEQ ID NO:77) |
| Primer set2 A1298C polymorph-lead | 5' tga cca gtg aag Caa gtg tct ttg a (SEQ ID NO:78) |
| Primer set2 A1298C polymorph-lag | 5' tca aag aca ctt Gct Tca ctg gtc a (SEQ ID NO:79) |
| 9. ALDH2 | |
| Primer set1 wt-lead | 5' cag gca tac act Gaa gtg aaa act g (SEQ ID NO:80) |
| Primer set 1 wt-lag | 5' cag ttt tca ctt Cag tgt atg cct g (SEQ ID NO:81) |
| Primer set1 polymorph-lead | 5' cag gca tac act Aaa gtg aaa act g (SEQ ID NO:82) |
| Primer set 1 polymorph-lag | 5' cag ttt tca ctt Tag tgt atg cct g (SEQ ID NO:83) |
| 10. beta-Actin | |
| Primer set 1-lead | 5' tgc atc tct gcc tta cag atc atg t (SEQ ID NO:84) |
| Primer set1-lag | 5' aga tga tct gta agg cag aga tgc a (SEQ ID NO:85) |

Advice Decision Tree

Figure 1:
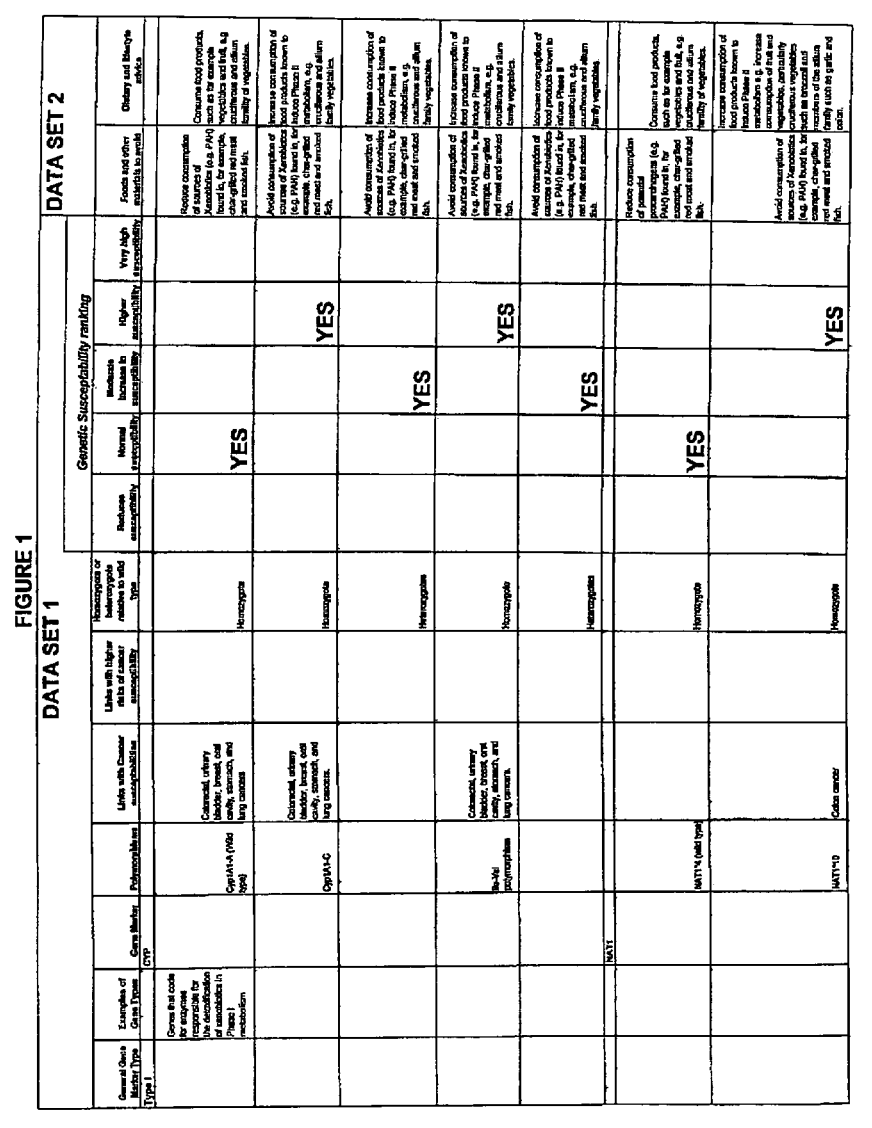

The results of genetic polymorphism analysis may be used to correlate the genetic profile of the donor of the sample with disease susceptibility using the first dataset, which provides details of the relative disease susceptibility associated with particular polymorphisms and their interactions. The risk factors identified using dataset 1 can then be matched with dietary and other lifestyle recommendations from dataset 2 to produce a lifestyle advice plan individualised to the genetic profile of the donor of the sample. Examples of datasets 1 and 2 which may be used to generate such advice is illustrated in FIG. 1.

To enable appropriate advice to be tailored to particular susceptibilities, a ranking system is preferably used to provide an indication of the degree of susceptibility of a specific polymorph to risk of cancer(s) and/or other conditions. The ranking system may be designed to take into account of homozygous or heterozygous alleles in the client's sample, i.e. the same or different alleles being present in diploid nucleus. Five categories which may be used are summarised below:

(i) Reduced susceptibility: where an allele has been shown to reduce susceptibility.

(ii) Normal susceptibility: where allele has been shown to have a normal susceptibility of risk to cancer(s) or disease. This is generally the homozygous wild type allele or a polymorphism that has been shown to have similar function.

(iii) Moderate susceptibility: where a heterozygous genotype is present that contains the wild type of the allele (i.e. normal susceptibility) and an allele of the polymorphism known to give rise to higher susceptibility to specific cancer(s) or disease.

(iv) High susceptibility: where a homozygous genotype that contains the polymorphism is present with a higher risk of cancer susceptibility.

(v) Higher susceptibility: where a higher susceptibility has been observed for specific cancer(s) or disease due to the combined effects of two or more different gene targets.

Using dataset 1, a susceptibility may be assigned to each polymorphism identified and, from dataset 2, a lifestyle recommendation corresponding to each susceptibility identified may be assigned. For example, if an individual is found to have the NAT1*10 polymorphism, the decision tree may indicate that the there is an enhanced susceptibility of colonic cancer. Recommendations appropriate to minimising the risk of colonic cancer are then generated. For example, the recommendations may be to avoid particular foods associated with increased risk and to increase consumption of other foods associated with a protective effect against such cancers. The totality of recommendations may be combined to generate a lifestyle advice plan individualised to the donor of the sample. The decision tree is preferably arranged to recognise particular combinations of polymorphisms and/or susceptibilities which interact either positively to produce a susceptibility greater than would be expected from the risk factors associated with each individually, and/or, which interact negatively to reduce the susceptibility associated with each individually. Where such combinations are identified, the advice generated can be tailored accordingly. For example, the combination of NAT2*4 and NAT1*10 polymorphisms have been linked to increased cancer risk (Bell, 1995). Therefore, when such a combination of polymorphisms is identified from a subject's DNA, the associated very high susceptibility to cancer is assigned and the advice tailored to emphasise the need to reduce consumption of xenobiotics, e.g. by reducing or eliminating consumption of char-grilled foodstuffs.

In generating the advice, other factors such as information concerning the sex and health of the individual and/or of the individual's family, age, alcohol consumption, and existing diet may be used in the determination of appropriate lifestyle recommendations.

Experimental

EXAMPLE 1

Preparation of DNA Sample

DNA is prepared from a buccal cell sample on a brush using a Qiagen QIAamp kit according to the manufacturer's instructions (Qiagen, Crawley, UK). Briefly, the brush is cut in half and one half stored at room temperature in a sealed tube in case retesting is required. The other half of the brush is placed in a microcentrifuge tube. 400 µl PBS is added and the brush allowed to rehydrate for 45 minutes at room temperature. Quiagen lysis buffer and Proteinase K is then added, the contents are mixed, and allowed to incubate at 56 C for 15 minutes to lyse the cells. Ethanol is added and the lysate transferred to a QIAamp spin column from which DNA is eluted after several washings.

EXAMPLE 2

Quantification of DNA

In order to check that sufficient DNA has been isolated, a quantification step is carried out using the PicoGreen dsDNA Quantification kit (Molecular Probes, Eugene, Oreg., USA).

Briefly, client DNA samples are prepared by transferring a 10 µl aliquot into a microcentrifuge tube with 90 µl TE. 100 µl of the working PicoGreen dsDNA quantification reagent is added, mixed well, and transferred into a black 96 well plate with flat well bottoms. The plate is then incubated for 5 minutes in the dark before a fluorescent reading is taken. The quantity of DNA present in the clients' samples is determined by extrapolating from a calibration plot prepared using DNA standards.

A quantity of DNA in the range of 5–50 ng total is used in the subsequent PCR step. Remaining client DNA sample is stored at −20° C. for retesting if required.

EXAMPLE 3

Taqman® Assay to Identify the MTHFR A1298C Polymorphism

The modified reaction mixture contains Taq polymerase (1.25 units/µl), optimised PCR buffer, dNTP (200 µM each), 2 mM $MgCl_2$ and primer pairs SEQ ID NO: 160 and 161 and polymorphism probe SEQ ID NO: 200.

The reaction mixture is initially incubated for 10 minutes at 50° C., then 5 minutes at 95° C., followed by 40 cycles of 1 minute of annealing at between 55° C. and 60° C. and 30 seconds of denaturation at 95° C. Both during the cycles and at the end of the run, fluorescence of the released reporter molecules of the probe is measured by an integral CCD detection system of the AB7700 thermocycler. The presence of a fluorescent signal which increases in magnitude through the course of the run indicates a positive result.

The assay is then repeated with the same primer pair and wt probe SEQ ID NO: 199. If the sample is homozygous for the polymorphism, no fluorescence signal is seen with the wt probe. However, if the sample is heterozygous for the polymorphism, a fluorescence signal is also seen with the wt probe. If single reporter results from homozygous wt, homozygous polymorphic and heterozygous polymorphic samples are plotted are plotted on an X/Y axis, the homozygous alleles will cluster at opposite ends of the axes relative to each reporter, and the heterozygous alleles will cluster at a midway region.

EXAMPLE 4

DNA Array Method for Identifying Polymorphisms for Identifying Multiple Polymorphisms a) PCR Amplification The PCR reaction mix contains Taq polymerase (1.25 units/reaction), optimised PCR buffer, dNTP's (200 µM each) and $MgCl_2$ at an appropriate concentration of between 1 and 4 mM, and 40 pmol of each primer(SEQ ID NOS: 1–8, 17–63) for amplification of seven fragments and the sample DNA.

The reaction mixture is initially incubated at 95° C. for 1 minute, and then subjected to 45 cycles of PCR in a MWG TC9600 thermocycler (MWG-Biotech-AG Ltd., Milton Keynes, UK) as follows:

annealing 50° C., 1 minute
polymerisation 73° C., 1 minute
denaturation 95° C., 30 seconds.

After a further annealing step at 50° C., 1 minute, there is a final polymerisation step at 73° C. for 7 minutes.

(Instead of the MWG TC9600 thermocycler, other thermocyclers, such as the Applied Biosystems 9700 thermocycler (Applied Biosystems, Warrington, UK), may be used.

After amplification of the target genes, generation of product is checked by electrophoresis separation using 2% agarose gel, or a 3.5% NuSieve agarose gel.

The PCR mplification products are then purified using the Qiagen QIAquick PCR Purification Kit (Qiagen, Crawley, UK) to remove dNTPs, primers, and enzyme from the PCR product. The PCR product is layered onto a QIAquick spin column, a vacuum applied to separate the PCR product from the other reaction products and the DNA eluted in buffer.

b) RNA Transcription and Fluorescent Labelling of PCR Products

The DNA is then transcribed into RNA using T3 and T7 RNA polymerases together with fluorescently labelled UTP for incorporation into the growing chain of RNA. The reaction mixture comprises:

20 µl 5× reaction buffer; 500 µM ATP, CTP, GTP, fluorescent UTP (Amersham Ltd, UK); DEPC treated $dH_2O$; 1 unit T3 RNA polymerase or 1 unit T7 RNA polymerase (Promega Ltd., Southampton, UK); 1 unit Rnasin ribonuclaese inhibitor and DNA from PCR (⅓ of total, 10 µl in $dH_2O$).

The mixture is incubated at 37° C. for 1 hour. The mixture is then treated with DNAse to remove DNA so that only newly synthesised fluorescent RNA is left. The RNA is then precipitated, microcentrifuged and resuspended in buffer for hybridisation on the array.

c) Polymorphism Analysis

The sample amplified fragments are then tested using a DNA microarray

The DNA microarray used comprises oligonucleotides SEQ ID NOs: 1–85. These oligonucleotides are applied by a robot onto a glass slide and immobilised. The fluorescently labelled amplified DNA is introduced onto the DNA microarray and a hybridisation reaction conducted to bind any complementary sequences in the sample, allowing unbound material to be washed away. The presence of bound samples is detected using a scanner. The absence of a fluorescent signal for a specific oligonucleotide probe indicates that the client does not have the corresponding polymorphism.

EXAMPLE 5

DNA Array Method for Identifying G560A Polymorphism

The PCR reaction mix contains Taq polymerase (1.25 units/reaction), optimised PCR buffer, dNTP's (200 µM each) and $MgCl_2$ at an appropriate concentration of between 1 and 4 mM, and 40 pmol of each primer (SEQ ID NOs: 88,89) for amplification of the fragment. The methods used is the same as detailed in Example 4, with the array comprising oligonucleotides SEQ ID NO: 17, 18, 19 and 20.

The presence of bound samples is detected using a scanner as described above. A highly fluorescent spot is detected at the positions corresponding to the oligonucleotides SEQ ID NO: 19 and 20. No signal is seen at the spots corresponding to SEQ ID NO: 17 and 18, demonstrating that the sample is not heterozygous for the wt allele.

EXAMPLE 6

Generation of Report

The results of the microarray or Taqman® analysis are input into a computer comprising a first dataset correlating the presence of individual alleles with a risk factor and a second dataset correlating risk factors with lifestyle advice. A report is generated identifying the presence of particular polymorphisms and providing lifestyle recommendations based on the identified polymorphisms. An example of such a decision process is shown in FIG. 2.

A sample of DNA is screened and the alleles identified input to a dataprocessor as Dataset 3. Each allele is matched to lifestyle risk factor from dataset 1, e.g. high susceptibility to colon cancer due to the presence of the NAT1*10 allele and the absence of the GSTM1 allele. The identified risk factor is then matched with one or more lifestyle recommendations from dataset 2, for example "avoid red meat, chargrilled food, smoked meats and fish; stop smoking immediately" (in order to avoid production of potentially toxic byproducts by Phase 1 enzymes with increased activity) and "increase consumption of vegetables of the allium family e.g. onions and garlic, and the brassaicae family e.g. broccoli" (in order to increase the activity of Phase 11 enzymes present, such as GSTP1 and GSTT1 and others, in order to increase the excretion of toxic byproducts of Phase 1 metabolism). This is then checked against other factors input into the dataprocessor, e.g. age, sex and existing diet to modify the recommendation accordingly before generating the final recommendation appropriate to the allele. The lifestyle recommendations are then assembled to generate a comprehensive personalised lifestyle advice plan.

REFERENCES

Abravaya, K., Carrino, J. J., Muldoon, S., and Lee, H. H. 1995. Detection of point mutation with a modified ligase chain reaction (Gap-LCR). Nucleic Acids Research. 23:675–682.

Agarwal, K., Jones, D. E., Daly, A. K., James, O. F., Vaidya, B., Pearce, S. & Bassendine, M. P., 2000, CTLA-4 gene polymorphism confers susceptibility to primary biliary cirrhosis, J Hepatol, 32, 4, p. 538–541.

Alexandrie, A.-K., Warholm, M., Carstensen, U., Axmon, A., Hagmar, L., Levin, J. O., Ostman, C., and Rannug, A. CYP1A1 and GSTM1 polymorphisms affect urinary 1-hydroyprene levels after PAH exposure. Carcinogenesis 21(4)669–676, 2000.

Ambrosone, C. B., Freudenheim, J. L., Thompson, P. A., Bowman, E., Vena, J. E., Marshall, J. R., Graham, S., Laughlin, R., Nemoto, T., and Shields P. G. Manganese Superoxide Dismutase (MnSOD) Genetic Polymorphisms, Dietary Antioxidants, and Risk of Breast Cancer. Cancer Research 59:602–606, 1999.

Ames, B. N. Cancer prevention and diet: Help from single nucleotide polymorphisms. Proceedings of the National Academy of Science USA 96(22):12216–12218, 1999.

Aron, Y., Swierczewski, E., Lockhart, A., 1994. A simple and rapid micromethod for genomic DNA extraction from jugal epithelial cells. Application to human lymphocyte antigen typing in one large family of atopic/asthmatic probands. Allergy 49 (9): 788–90.

Ban, Y. & Taniyama, M., 2000, Vitamin D Receptor Gene Polymorphism Is Associated with Graves' Disease in the Japanese Population, J Clin Endocrinol Metab, 85, 12, p. 4639–4643.

Barany, F. 1991. Genetic disease detection and DNA amplification and DNA amplification using cloned thermostable ligase. Proceedings of the National Academy of Science. USA 88:189–193.

Bell, D. A, Stephens, E., Castranio, T., Umback, D. M., Watson, M., Deakin, M., Elder, J., Duncan, H., Hendrickse, C., Strange, R. C. Polyadenylation polymorphism in the N-acetyltransferase gene 1 (NAT1) increases risk of colorectal cancer. Cancer Research 55: 3537–3542, 1995.

Bosron, W. F. and Li, T. K. Genetic polymorphism of human liver alcohol and aldehyde dehydrogenases and their relationship to alcohol metabolism and alcoholism. Hepatology 6: 502–510, 1986.

Brand, E., Ringel, J. & Sharma, A. M., 2000, Role of the angiotensinogen gene for essential hypertension, Herz, 25, 1, p. 15–25.

Breslauer, et al., "Predicting DNA duplex stability from base sequence", Proc. Nat'l Acad. Sci. USA, 83: 3746–3750 (1986)

Brockton, N., Little, J., Sharp, L, and Cotton, S. C. N-Acetyltransferase Polymorphisms and Colorectal Cancer: A HuGE Review. American Journal of Epidemiology 151(9): 846–861, 2000.

Bryant, M. S., Skipper, P. L., Tannenbaum, S. R., and Niure, M. Haemoglobin adducts of 4-aminobiphenyl in smokers and non-smokers. Cancer Research 47: 612–618, 1987.

Buervenich, S., Sydow, O., Carmine, A., Zhang, Z., Anvret, M. & Olson, L., 2000, Alcohol dehydrogenase alleles in Parkinson's disease, Mov Disord, 15, 5, p. 813–818.

Bullido, M. J. & Valdivieso, F., 2000, Apolipoprotein E gene promoter polymorphisms in Alzheimer's disease, Microsc Res Tech, 50, 4, p. 261–267.

Cheung, V. G., et. al., 1999, Nature, Genetics, vol. 21, 15–19.

Corbo, R. M. & Scacchi, R., 1999, Apolipoprotein E (APOE) allele distribution in the world. Is APOE*4 a 'thrifty' allele?, Ann Hum Genet, 63, PT4, p. 301–310.

Costa, L. G., 2000, The emerging field of ecogenetics, Neurotoxicology, 21, 1–2, p. 85–89.

Cotton, S. C., Sharp, L., Little, J., and Brockton, N. Glutathione S-Transferase Polymorphisms and Colorectal Cancer (A HuGE review). American Journal of Epidemiology 151(1)7–32, 2000.

Cramer, D. W., Greenberg, E. R., Titus-Ernstoff, L., Liberman, R. F., Welch, W. R., Li, E. & Ng, W. G., 2000, A case-control study of galactose consumption and metabolism in relation to ovarian cancer, Cancer Epidemiol Biomarkers Prev, 9, 1, p. 95–101.

Cramer, D. W., Greenberg, E. R., Titus-Ernstoff, L., Liberman, R. F., Welch, W. R., Li, E. & Ng, W. G., 2000, A case-control study of galactose consumption and metabolism in relation to ovarian cancer, Cancer Epidemiol Biomarkers Prev, 9, 1, p. 95–101.

de Padua Mansur, A.; Annicchino-Bizzacchi, J.; Favarato, D.; Avakian, S. D.; Machado Cesar, L. A.; Franchini Ramires, J. A., 2000. Angiotensin-converting enzyme and apolipoprotein B polymorphisms in coronary artery disease. Am J Cardiol 85 (9): 1089–93.

Di Castelnuovo, A., D'Orazio, A., Amore, C., Falanga, A., Donati, M. B. & Iacoviello, L., 2000, The decanucleotide insertion/deletion polymorphism in the promoter region of the coagulation factor VII gene and the risk of familial myocardial infarction, Thromb Res, 98, 1, p. 9–17.

Dickey, C., Snatella, R., Hattis, D., Tang, D., Hsu, Y., Cooper, T., Young, T. and Perera F., Variability in PAH-DNA adduct measurements in peripheral mononuclear cells: implications for quantitative cancer risk assessment. Risk Analysis 17: 649–655, 1997.

Dietz, A. C., Zheng, W., Leff, M. A., Gross, M., Xiao, G.-F., Doll, M. A., Wen, W.-Q., Folsom, A. R., Hein, D. W. N-acetyltransferase-2 (NAT2) acetylation polymorphism, well-done meat intake and breast cancer risk among post-menopausal women. Proceedings of the American Association for Cancer Research, 40: 148, 1999.

Doll, M. A., Jiang, W., Deitz, A. C., Rustan, T. D., and Hein, D. W. Identification of a novel allele at the human NAT1 acetyltransferase locus. Biochem. Duiophys. Res. Commun. 233: 584–591, 1997.

Donati, M. B., Zito, F., Castelnuovo, A. D. & Iacoviello, L., 2000, Genes, coagulation and cardiovascular risk, J Hum Hypertens, 14, 6, p. 369–372.

Donis-Keller H., Green P, Helms C., et. al. (1987), A genetic map of the human genome. Cell, 51, 319–337

Eberhart, M. V., Lee, C. Y., Liu, R. H. Antioxidant activity of fresh apples. Nature 405: 903–904, 2000. Fernandez-Real, J. M., Vendrell, J., Ricart, W., Broch, M., Gutierrez, C., Casamitjana, R., Oriola, J. & Richart, C., 2000, Polymorphism of the tumor necrosis factor-alpha receptor 2 gene is associated with obesity, leptin levels, and insulin resistance in young subjects and diet-treated type 2 diabetic patients, Diabetes Care, 23, 6, p. 831–837.

Garte, S. The role of ethnicity in cancer susceptibility gene polymorphisms: the example of CYP1A1. Carcinogenesis 19(8) 1329–1332, 1998.

Gelder, C. M., Hart, K. W., Williams, O. M., Lyons, E., Welsh, K. I., Campbell, I. A., Marshall, S. E., 2000, Vitamin D receptor gene polymorphisms and susceptibility to Mycobacterium malmoense pulmonary disease, J Infect Dis, 181, 6, p. 2099–2102.

Gibbs, R. A., Nguyen, P. N., and Caskey, C. T. 1989. Detection of single DNA base differences by competitive oligonucleotides priming. Nucleic Acids Research. 17:2437–2448.

Gil, J. P., Lechner, M. C. Increased frequency of wild type arylamine-N-actyltransferase allel NAT2*4 homozygotes in Portuguese patients with colorectal cancer. Carcinogenesis 19(1) 37–41, 1998.

Giovannucci, E. Nutritional factors in human cancers. Advances in Experimental Medicine and Biology 472: 29–42, 1999.

Grossman, P. D., Bloch, W., Brinson, E., Chang, C. C., Eggerding, F. A., Fung, S., Iovannisci, D. A., Woo, S., and Winn-Deen, E. S. 1994. High-density multiplex detection of nucleic acid sequences: oligonucleotides ligation assay and sequence-coded separation. Nucleic Acid Research. 22:4527–4534.

Harries, L. W., Stubbins, M. J., Forman, D., Howard, G. c. W, Wolf R. Identification of genetic polymorphisms at the glutathione S-transferase pi locus and association with susceptibility to bladder, testicular, and prostate cancer. Carcinogenesis 18:641–644, 1997.

Hattis D., Erdreich, L, and DiMauro, T. Human Variability in Parameters that are Potentially Related to Susceptibility to Carcinogenesis-I.

Preliminary Observations. Center for Technology, Policy and Industrial Development, MIT, Cambridge, Mass., 1986.

Heilbronn, L. K., Noakes, M., Morris, A. M., Kind, K. L., Clifton, P. M., 2000, 360His polymorphism of the apolipoproteinA-IV gene and plasma lipid response to energy restricted diets in overweight subjects, Atherosclerosis, 150, 1, p. 187–192.

Hein, D., Doll, M. A., Fretland, A. J., Leff, M. A., Webb, S. J., Xiao, U.-S. D., Nangju, N., Feng, Y., Molecular Genetics and Epidemiology of the NAT1 and NAT2 Acetylation Polymorphisms. Cancer Epidemiology, Biomarkers & Prevention 9: 29–42, 2000 (a).

Hein, D., N-Acetyltransferase genetics and their role in predisposition to aromatic and heterocyclic amine-induced carcinogenesis. Toxicology Letters 112–113: 349–356, 2000 (b).

Hennig, B. J., Parkhill, J. M., Chapple, I. L., Heasman, P. A. & Taylor, J. J., 1999, Association of a vitamin D receptor gene polymorphism with localized early-onset periodontal diseases, J Periodontol, 70, 9, p. 1032–1038.

Hirvonen, A. Polymorphisms of Xeno-biotic-Metaboilzing Enzymes and Susceptibility to Cancer. Environ Health Perspect 107 Supplement 1: 37–47, 1999.

Humphries, S. E., Henry, J. A. & Montgomery, H. E., 1999, Gene-environment interaction in the determination of levels of haemostatic variables involved in thrombosis and fibrinolysis, Blood Coagul Fibrinolysis, 10 Suppl 1, p. S17–S21.

Ikuta, S., Takagi K., Wallace, R. B., and Itakura, K. 1987. Dissociation Kinetics of 19 base paired oligonucleotides-DNA Duplexes containing different single mismatched base pairs. Nucleic Acids Research. 15:797–811.

Ilett, K. F., David, B. M., Dethon, P., Castlden, W. M, and Kwa, R. Acetylation phenotype in colorectoal carcinoma. Cancer Research 47:1466–1469, 1987.

International Agency for Research on Cancer (IARC). Alcohol Drinking. IARC monographs on the evaluation of the carcinogenic risks to humans, IARC, Lyon. 44:153–246, 1998.

Kato, S., Bowman, E. D., Harrington, A. M., et al Human lung carcinogen DNA adduct levels mediated by genetic polymorphisms in vivo. Journal of the National Cancer Institute 87:902–907, 1995.

Kawajiri, K., Eguchi, H., Nakachi, K., Seklya., T., Yamamoto, M. Association of CYP1A1 germ line polymorphisms with mutations of the p53 gene in lung cancer. Cancer Research 56:72–76, 1996.

Landegren, U., Kaiser, R., Sanders, J., and Hood, L, 1988. A ligand-mediated gene detection technique. Science. 241:1077–1080.

Laplaud, P. M., Dantoine, T. & Chapman, M. J., 1998, Paraoxonase as a risk marker for cardiovascular disease: facts and hypotheses, Clin Chem Lab Med, 36, 7, p. 431–441.

Layton, D. W., Bogen, K. T., Knize, M. G., Hatch, F. T., Johnson, V. M., and Felton, J. S. Cancer risk of heterocyclic amines in cooked foods: an analysis and implications for research. Carcinogenesis 16: 39–52, 1995.

Lee, E., Huang, Y., Zhao, B. et al Genetic polymorphism of conjugating enzymes and cancer risk: GSTM1, GSTT1, NAT1 and NAT2. Journal of the Toxicological Society 23: 140–142, 1998.

Maciag, P. C., Schlecht, N. F., Souza, P. S., Franco, E. L., Villa, L. L. & Petzl-Erler, M. L., 2000, Major histocompatibility complex class II polymorphisms and risk of cervical cancer and human papillomavirus infection in Brazilian women, Cancer Epidemiol Biomarkers Prev, 9, 11, p. 1183–1191.

MacKness, B., Mackness, M. I., Durrington, P. N., Arrol, S., Evans, A. E., McMaster, D., Ferrieres, J., Ruidavets, J. B., Williams, N. R. & Howard, A. N., 2000, Paraoxonase activity in two healthy populations with differing rates of coronary heart disease, Eur J Clin Invest, 30, 1, p. 4–10.

MacLeod, S., Sinha, R., Kadlubar, F. F., Lang, N. P. Polymorphisms of CYP1A1 and GSTM1 influence the in vivo function of CYP1A2. Mutation Research 376(1–2): 135–142, 1997.

Maniatis T., Fritsch E. F., and Sambrook J., (1982) Molecular Cloning A Laboratory Manual, Cold Spring Harbor Laboratory, Cold Springs Harbor, NY.

Marchand, L. L., Wilkinson, G. R. & WilKens, L. R., 1999, Genetic and dietary predictors of CYP2E1 activity: a phenotyping study in Hawaii Japanese using chlorzoxazone, Cancer Epidemiol Biomarkers Prev, 8, 6, p. 495–500.

Matthias, C., Bockmuhl, U., Jahnke, V., Harries, L., Wolf, C. R., Jones, P. W., Alidersea, J. Worrall, S. F., Hand, P., Fryer, A. A. et al, The glutathione-S-transferase GSTP1 polymorphism: effects on susceptibility to oral/phryngeal and laryngeal carcinomas. Pharmacogenetics 8: 1–6, 1997.

Miki, M. & Satoh, K., 1999, Genetic risk factors for chronic obstructive pulmonary disease (COPD), Nippon Rinsho, 57, 9, p. 1954–1958.

Mooney, L. A., Perera, F. P. Application of molecular epidemiology to lung cancer chemoprevention. Journal of Cellular Biochemistry Supplement 25:63–8, 1996.

Mooney, L. A., Santella, R. M., Covey, L., Jeffrey, A. M., Bigbee, W., Randall, M. C., Cooper, T. B., Ottman, R., Tsai, W.-Y., Wazneh, L. et al. Decline in DNA damage and other biomarkers in peripheral blood following smoking cessation. Cancer Epidemiological Biomarkers Prevention 4:627–634, 1995.

Nakajima, T. & Aoyama, T., 2000, Polymorphism of drug-metabolizing enzymes in relation to individual susceptibility to industrial chemicals, Ind Health, 38, 2, p. 143–152.

Newton, C. R., Graham, A., Heptinstall, L. E., Powell, S. J., Summers, C., Kalsheker, N., Smith, J. C., and Markham, A. F. 1989. Analysis of any point mutation in DNA. The amplification refractory mutation system (ARMS). Nucleic Acids Research. 17:2503–2516.

Nickerson, D. A., Kaiser, R., Lappin, S., Stewart, J., Hood, L., and Landegren, U. 1990. Automated DNA diagnostics using an ELISA-based oligonucleotides ligation assay. Proceedings of the National Academy of Science. USA 87:8923–8927.

Oliveira, J. R. & Zatz, M., 1999, The study of genetic polymorphisms related to serotonin in Alzheimer's disease: a new perspective in a heterogenic disorder, Braz J Med Biol Res, 32, 4, p. 463–467.

Ordovas, J. M., Cupples, L. A., Corella, D., Otvos, J. D., Osgood, D., Martinez, A., Lahoz, C., Coltell, O., Wilson, P. W., Schaefer, E. J., 2000, Association of cholesteryl ester transfer protein-TaqIB polymorphism with variations in lipoprotein subclasses and coronary heart disease risk: the Framingham study, Arterioscler Thromb Vasc Biol, 20, 5, p. 1323–1329.

Ota, N., Hunt, S. C., Nakajima, T., Suzuki, T., Hosoi, T., Orimo, H., Shirai, Y. & Emi, M., 1999, Linkage of interleukin 6 locus to human osteopenia by sibling pair analysis, Hum Genet, 105, 3, p. 253–257. p Perera, F. P. Molecular epidemiology and prevention of cancer. Environmental Health Perspectives 103 Suppl 8: 233–6, 1995.

Perera, P. P. Biomarkers and Molecular Epidemiology of Cancer. Proceedings of the 9th International Symposium in Epidemiology in Occupational Health. National Institute for Occupational Safety and Health, Cincinnati, Ohio. PP 54–66, 1992.

Perera, F. P. Environment and cancer: Who are susceptible? Science 278:1068–1073, 1997.

Perera, F. P. and Weinstein I. B. Molecular epidemiology: recent advances and future directions. Carcinogenesis 21 (3):517–524, 2000.

Pfutzer, R. H., Barmada, M. M., Brunskill, A. P., Finch, R., Hart, P. S., Neoptolemos, J., Furey, W. F. & Whitcomb, D. C., 2000, SPINK1/PSTI polymorphisms act as disease modifiers in familial and idiopathic chronic pancreatitis, Gastroenterology, 119, 3, p. 615–623.

PicoGreen dsDNA Quantitation Reagent and Kit Instruction, (1996) Molecular Probes, Eugene, Oreg.

Pluth, J. M., Nelson, D. O., Ramsey, M. J. & Tucker, J. D., 2000, The relationship between genotype and chromosome aberration frequencies in a normal adult population, Pharmacogenetics, 10, 4, p. 311–319.

Poolsup, N., Li Wan Po, A. & Knight, T. L., 2000, Pharmacogenetics and psychopharmacotherapy, J Clin Pharm Ther, 25, 3, p. 197–220.

Potter, J. D. Colorectal cancer: Molecules and Populations. Journal of the National Cancer Institute 91(11): 916–932, 1999.

Raknes, G., Fernandes Filho, J. A., Pandey, J. P., Myhr, K. M., Ulvestad, E., Nyland, H., Vedeler, C. A., 2000, IgG allotypes and subclasses in Norwegian patients with multiple sclerosis, J Neurol Sci, 175, 2, p. 111–115.

Rojas, M., Cascorbi, I., Alexandrov, K., Kried, E., Auburtin, G., Mayer, L., Kopp-Schnieder, A., Roots, I., and Bartsch, H. Modulation of benzo[a]pyrene diolepoxide-DNA adduct levels in human white blood cells by CYP1A1 GSTM1 and GSTT1 polymorphism, Carcinogenesis 21(1): 35–41, 2000.

Rosa-Rosa, L., Zimmermann, N., Bernstein, J. A., Rothenberg, M. E. & Khurana Hershey, G. K., 1999, The R576 IL-4 receptor alpha allele correlates with asthma severity, J Allergy Clin Immunol, 104, 5, p. 1008–1014.

Ryberg, D., Skaug, V., Hewer, A., Phillips, D. H., Harries, L. W., Wolf, C. R., Ogreid, D., Ulvik, A., Vu, P. Haugen, A. Genotypes of glutathione transferase M1 and P1 and their significance for lung DNA adduct levels and cancer risk. Carcinogenesis 18:1285–1289, 1997.

Rylchik, W., "Selection of Primers for Polymerase Chain Reaction", Methods in Molecular Biology, Vol. 15: PCR Protocols: Current Methods and Applications, pp 31–40 (1993) Humana Press.

Saiki, R. K., Walsh, P. S., Levenson, C. H., and Erlich, H. A. 1989. Genetic analysis of amplified DNA with immobilized sequence-specific oligonucleotides probes. Proceedings of the National Academy of Science. USA 86:6230–6234.

Salas, J., Jansen, S., Lopez-Miranda, J., Ordovas, J. M., Castro, P., Marin, C., Ostos, M. A., Bravo, M. D., Jimenez-Pereperez, J., Blanco, A., Lopez-Segura, F., Perez-Jimenez, F., 1998, The SstI polymorphism of the apolipoprotein C-III gene determines the insulin response to an oral-glucose-tolerance test after consumption of a diet rich in saturated fats, Am J Clin Nutr, 68, 2, p. 396–401.

Schabath, M. B., Spitz, M. R., Zhang, X., Delclos, G. L. & Wu, X., 2000, Genetic variants of myeloperoxidase and lung cancer risk, Carcinogenesis, 21, 6, p. 1163–1166.

Schena, M., 1999, DNA Nicroarrays "a practical approach", ISBN, 0-19-963777-6, Oxford press, editor B. D. Hames Shields, P. G., Harris, C.C. Cancer Risk and low-Penetrance Susceptibility Genes in Gene-Environment Interactions. Journal of Clinical Oncology 18(11) 2309–2315, 2000.

Sinha, R. & Caporaso, N., 1997, Heterocyclic amines, cytochrome P4501A2, and N-acetyltransferase: issues involved in incorporating putative genetic susceptibility markers into epidemiological studies, Ann Epidemiol, 7, 5, p. 350–356.

Sinha, R., Chow, W. H., Kulldorff, M., Denobile, J., Butler, J., Garcia-Closas, M., Weil, R., Hoover, R. N., and Rothman, N. Well-done, Grilled Red Meat Increases the Risk of Colorectal Adenomas. Cancer Research 59:4320–4324, 1999.

Smith, G., Stanley, L. A., Sim, E., Strange, R., and Wolf, C. R. Metabolic Polymorphisms and Cancer Susceptibility. Cancer Surveys 25: 27–65, 1995.

Syvanen, A. C., Sayantile, A., and Lukka, M. 1993. Identification of individuals by analysis of biallelic DNA markers, Using PCR and solid-phase minisequencing. American Journal of Human Genetics. 52:46–59.

Taningher, M., Malacarne, D., Izzotti, A., Ugolini, D. Parodi, S. Drug metabolism polymorphisms as modulators of cancer susceptibility. Mutation Research 436: 227–261, 1999.

Togo, A. V., Suspitsin, E. N., Grigoriev, M. Y., Ilyushik, E. S., Karpova, M. B., Hanson, K. P. & Imyanitov, E. N., 2000, L-myc polymorphism in cancer patients, healthy blood donors and elderly, tumor-free individuals in Russia, Int J Cancer, 85, 6, p. 747–750.

Tsai, M. Y., Welge, B. G., Hanson, N. Q., Bignell, M. K., Vessey, J., Schwichtenberg, K., Yang, F., Bullemer, F. E., Rasmussen, R. & Graham, K. J., 1999, Genetic causes of mild hyperhomocysteinemia in patients with premature occlusive coronary artery diseases, Atherosclerosis, 143, 1, p. 163–170.

Ulrich, C. M., Kampman, E., Bigler, J., Schwartz, S. M., Chen, C., Bostick, R., Fosdick, L., Bereford, S. A. A., Yasui, Y., and Potter, J. D. Colorectal adenomas and the C677T MTHFR polymorphism: evidence for gene-environment interaction? Cancer Epidemiological Biomarkers Prevention 8: 659–668, 1999.

Verlaan-de Vries, M., Bogaard, M. E., van den Elst, H., van Boom, J. H., van der Eb, A. J., and Bos, J. L. 1986. A dot-blot screening procedure for mutated ras oncogenes using synthetic oligodeoxynucleotides. Gene. 50:313–320.

Vicente, V., Gonzalez-Conejero, R., Rivera, J. & Corral, J., 1999, The prothrombin gene variant 20210A in venous and arterial thromboembolism, Haematologica, 84, 4, p 356–362.

Vineis, P. Molecular Epidemiology: Low-dose Carcinogens and genetic susceptibility. International Journal of Cancer 71: 1–3, 1997.

Wallace, A. J., Humphries, S. E., Fisher, R. M., Mann, J. I., Chisholm, A., Sutherland, W. H., 2000, Genetic factors associated with response of LDL subfractions to change in the nature of dietary fat, Atherosclerosis, 149, 2, p 387–394.

Wallace, R. B., Johnson, M. J., Hirose, T., Miyake, T., Kawashima, F. H. and Itakura, K., 1981. The use of synthetic oligonucleotides as hybridisation probes. II.

Hybridization of oligonucleotides of mixed sequence to rabbit beta-globin DNA. Nucleic Acids Research. 9:879–894.

Wilkinson, R. J., Llewelyn, M., Toossi, Z., Patel, P., Pasvol, G., Lalvani, A., Wright, D., Latif, M. & Davidson, R. N., 2000, Influence of vitamin D deficiency and vitamin D receptor polymorphisms on tuberculosis among Gujarati Asians in west London: a case-control study, Lancet, 355, 9204, p. 618–621.

World Cancer Research Fund (WCRF) Panel. (Potter, J. D. Chair) Diet, nutrition, and the prevention of cancer: a global perspective. Washington, D.C.: WCRF/American Institute of Cancer Research, 1997.

Wu, D. Y., and Wallace, R. B. 1989. The ligation amplification reaction (LAR)-amplification of specific DNA sequences using sequential rounds of template-dependent ligation. Genomics. 4:560–569.

Yamada, N., Yamaya, M., Okinaga, S., Nakayama, K., Sekizawa, K., Shibahara, S. & Sasaki, H., 2000, Microsatellite polymorphism in the heme oxygenase-1 gene promoter is associated with susceptibility to emphysema, Am J Hum Genet, 66, 1, p. 187–195.

Yershov, G., Barsky, V., et. al., 1996, Proc. Natl. Acad. Sci. USA, Genetics, Vol. 93, 4913–4918.

Yokota, M., Ichihara, S., Lin, T. L., Nakashima, N. & Yamada, Y., 2000, Association of a T29->C polymorphism of the transforming growth factor-beta1 gene with genetic susceptibility to myocardial infarction in Japanese, Circulation, 101, 24, p. 2783–2787.

Yokoyama, A., Muramatsu, T., Ohmori, T., Yokoyama, T., Okuyama, K., Takahashi, H., Hasegawa, Y., Higuchi, S., Maruyama, K., Shirakura, K., Ishii, H. Alcohol-related cancers and aldehyde dehydrogenase-2 in Japanese alcoholics. Carcinogenesis 19(8)1383–1387, 1998.

Zhang, Y., Coyne, M. Y., Will, S. G., Levenson, C. H., and Kawasaki, E. S. 1991. Single-base mutational analysis of cancer and genetic disease using membrane bound modified oligonucleotides. Nucleic Acids Research. 19:3929–3933.

Zheng, W., Deitz, A. C., Campbell, D. R., Wen, W-Q., Cerhan, J. R., Sellers, T. A., Folsom, A. R., and Hein, D. W. N-acetyltransferase I genetic polymorphism, cigarette smoking, well-done meat intake, and breast cancer risk. Cancer Epidemiological Biomarkers Prevention 8: 233–239, 1999.

Zychma, M. J., Gumprecht, J., Zukowska-Szczechowska, E. & Grzeszczak, W., 1999, Polymorphisms in the genes encoding for human kinin receptors and the risk of end-stage renal failure: results of transmission/disequilibrium test. The End-Stage Renal Disease Study Group, J Am Soc Nephrol, 10, 10, p. 2120–2124.

---

The invention claimed is:

1. A computer assisted method of providing a personalized lifestyle advice plan for a human subject comprising:

(i) providing a first dataset on a data processing device, said first dataset comprising information correlating the presence of individual alleles known to be associated with increased or decreased disease susceptibility, with a lifestyle risk factor;

(ii) providing a second dataset on a data processing device, said second dataset comprising information matching each said risk factor with at least one lifestyle recommendation;

(iii) inputting a third dataset identifying alleles present in said subject, wherein said alleles are one or more of the alleles of said first dataset;

(iv) determining the risk factors associated with said alleles present in said human subject by correlating said alleles with risk factors provided by said first dataset;

(v) determining at least one lifestyle recommendation based on each identified risk factor from step (iv) by matching said risk factor with a lifestyle recommendation from said second dataset; and (vi) generating a personalized lifestyle advice plan based comprising at least one lifestyle recommendation determined in step (v), wherein said personalized lifestyle advice plan includes recommended minimum and/or maximum amounts of food subtypes.

2. The method according to claim 1 wherein the method comprises the step of delivering the plan to the client.

3. The method according to claim 2 wherein the plan is delivered via the Internet and accessible via a unique identifier code.

4. The method according to claim 3 wherein the plan comprises hyperlinks to one or more Web pages.

5. The method according to claim 1 wherein said first dataset comprises information relating to two or more alleles of a gene selected from the group comprising:
  (a) a gene that encodes an enzyme responsible for detoxification of xenobiotics in Phase I metabolism;
  (b) a gene that encodes an enzyme responsible for conjugation reactions in Phase II metabolism;
  (c) a gene that encodes an enzyme that helps cells to combat oxidative stress;
  (d) a gene associated with micronutrient deficiency; and
  (e) a gene that encodes an enzyme responsible for metabolism of alcohol.
  (f) a gene that encodes an enzyme involved in lipid and/or cholesterol metabolism;
  (g) a gene that encodes an enzyme involved in clotting;
  (h) a gene that encodes a trypsin inhibitor;
  (i) a gene that encodes an enzyme related to susceptibility to metal toxicity;
  (j) a gene which encodes a protein required for normal cellular metabolism and growth;
  (k) a gene which encodes a HLA Class 2 molecule.

6. The method according to claim 5 wherein said first dataset comprises information relating to two or more alleles of a gene selected from each member of the group comprising:
  (a) a gene that encodes an enzyme responsible for detoxification of xenobiotics in Phase I metabolism;
  (b) a gene that encodes an enzyme responsible for conjugation reactions in Phase II metabolism;
  (c) a gene that encodes an enzyme that helps cells to combat oxidative stress;
  (d) a gene associated with micronutrient deficiency; and
  (e) a gene that encodes an enzyme responsible for metabolism of alcohol.
  (f) a gene that encodes an enzyme involved in lipid and/or cholesterol metabolism;
  (g) a gene that encodes an enzyme involved in clotting;
  (h) a gene that encodes a trypsin inhibitor;
  (i) a gene that encodes an enzyme related to susceptibility to metal toxicity;
  (j) a gene which encodes a protein required for normal cellular metabolism and growth;
  (k) a gene which encodes a HLA Class 2 molecule.

7. The method according to claim 5 wherein said first dataset comprises information relating to two or more alleles of a gene encoding an enzyme selected from the group comprising: cytochrome P450 monooxygenase, N-acetyltransferase 1, N-acetyltransferase 2, glutathione-S-transferase, manganese superoxide dismutase, 5,10-methylene-tetrahydrofolatereductase and alcohol dehydrogenase 2.

8. The method according to claim 7 wherein said first dataset comprises information relating to two or more alleles of each of the genes encoding cytochrome P450 monooxygenase, N-acetyltransferase 1, N-acetyltransferase 2, glutathione-S-transferase, manganese superoxide dismutase, 5,10-methylene-tetrahydrofolatereductase and alcohol dehydrogenase 2.

9. The method of claim 8 wherein said alleles are alleles of genes selected from the group consisting of the MTHFR gene, the MnSOD gene, the CYP1A1 gene, the GSTµ gene, GSTπ gene, the GSTΘθgene and the ALDH2 gene.

10. The method according to claim 1 including the step determining the presence of individual alleles in a DNA sample of said human subject, and constructing the dataset used in step (iii) using results of said determination.

11. The method according to claim 10 wherein said presence of said individual alleles is determined by hybridisation with allele-specific oligonucleotides.

12. The method according to claim 11 wherein said allele specific oligonucleotides are selected from oligonucleotides each specific for one of the genes selected from the group comprising the CYP1A1 gene, the GSTµ gene, the GSTπ gene, the GSTΘθgene, the NAT1 gene, the NAT2 gene, the MnSOD gene, the MTHFR gene and the ALDH2 gene.

13. The method of claim 1 wherein said first dataset and said second dataset are provided on the same data processing device.

14. A computer assisted method of providing a personalized lifestyle advice plan for a human subject comprising:
  (i) providing a first dataset on a data processing device, said first dataset comprising information correlating the presence of individual alleles known to be associated with increased or decreased disease susceptibility, with a lifestyle risk factor;
  (ii) providing a second dataset on a data processing device, said second dataset comprising information matching each said risk factor with at least one lifestyle recommendation;
  (iii) inputting a third dataset identifying alleles present in said subject, wherein said alleles are two or more of the alleles of said first;
  (iv) determining the risk factors associated with said alleles present in said human subject by correlating said alleles with risk factors provided by said first dataset;
  (v) determining at least one lifestyle recommendation based on each identified risk factor from step (iv) by matching said risk factor with a lifestyle recommendation from said second dataset; and
  (vi) generating a personalized lifestyle advice plan based comprising at least one lifestyle recommendation determined in step (v), wherein said personalized lifestyle advice plan includes recommended minimum and/or maximum amounts of food subtypes.

15. The method according to claim 14 wherein the method comprises the step of delivering the plan to the client.

16. The method according to claim 15 wherein the plan is delivered via the Internet and accessible via a unique identifier code.

17. The method according to claim 16 wherein the plan comprises hyperlinks to one or more Web pages.

18. The method according to claim 14 wherein said first dataset comprises information relating to two or more alleles of two or more genes selected from the group comprising:
  (a) a gene that encodes an enzyme responsible for detoxification of xenobiotics in Phase I metabolism;
  (b) a gene that encodes an enzyme responsible for conjugation reactions in Phase II metabolism;
  (c) a gene that encodes an enzyme that help cells to combat oxidative stress;
  (d) a gene associated with micronutrient deficiency; and
  (e) a gene that encodes an enzyme responsible for metabolism of alcohol.
  (f) a gene that encodes an enzyme involved in lipid and/or cholesterol metabolism;
  (g) a gene that encodes an enzyme involved in clotting;
  (h) a gene that encodes a trypsin inhibitor;
  (i) a gene that encodes an enzyme related to susceptibility to metal toxicity;
  (j) a gene which encodes a protein required for normal cellular metabolism and growth;
  (k) a gene which encodes a HLA Class 2 molecule.

19. The method according to claim 18 wherein said first dataset comprises information relating to two or more alleles of a gene selected from each member of the group comprising:
   (a) a gene that encodes an enzyme responsible for detoxification of xenobiotics in Phase I metabolism;
   (b) a gene that encodes an enzyme responsible for conjugation reactions in Phase II metabolism;
   (c) a gene that encodes an enzyme that help cells to combat oxidative stress;
   (d) a gene associated with micronutrient deficiency; and
   (e) a gene that encodes an enzyme responsible for metabolism of alcohol.
   (f) a gene that encodes an enzyme involved in lipid and/or cholesterol metabolism;
   (g) a gene that encodes an enzyme involved in clotting;
   (h) a gene that encodes a trypsin inhibitor;
   (i) a gene that encodes an enzyme related to susceptibility to metal toxicity;
   (j) a gene which encodes a protein required for normal cellular metabolism and growth;
   (k) a gene which encodes a HLA Class 2 molecule.

20. The method according to claim 18 wherein said first dataset comprises information relating to two or more alleles of of a gene encoding an enzyme selected from the group comprising: cytochrome P450 monooxygenase, N-acetyltransferase 1, N-acetyltransferase 2, glutathione-S-transferase, manganese superoxide dismutase, 5,10-methylenetetrahydrofolatereductase and alcohol dehydrogenase 2.

21. The method according to claim 20 wherein said first dataset comprises information relating to two or more alleles of each of the genes encoding cytochrome P450 monooxygenase, N-acetyltransferase 1, N-acetyltransferase 2, glutathione-S-transferase, manganese superoxide dismutase, 5,10-methylenetetrahydrofolatereductase and alcohol dehydrogenase 2.

22. The method of claim 21 wherein said alleles are alleles of genes selected from the group consisting of the MTHFR gene, the MnSOD gene, the CYP1A1 gene, the GSTµ gene, GSTTπ gene, the GSTΘθgene and the ALDH2 gene.

23. The method according to claim 14 including the step determining the presence of individual alleles in a DNA sample of said human subject, and constructing the dataset used in step (iii) using results of said determination.

24. The method according to claim 23 wherein said presence of said individual alleles is determined by hybridisation with allele-specific oligonucleotides.

25. The method according to claim 24 wherein said allele specific oligonucleotides are selected from oligonucleotides each specific for two of the genes selected from the group comprising the CYP1A1 gene, the GSTµ gene, the GSTπ gene, the GSTΘθgene, the NAT1 gene, the NAT2 gene, the MnSOD gene, the MTHFR gene and the ALDH2 gene.

26. The method of claim 14 wherein said first dataset and said second dataset and provided on the same data processing device.

* * * * *